(12) United States Patent
Tamarkin et al.

(10) Patent No.: US 8,795,635 B2
(45) Date of Patent: *Aug. 5, 2014

(54) SUBSTANTIALLY NON-AQUEOUS FOAMABLE PETROLATUM BASED PHARMACEUTICAL AND COSMETIC COMPOSITIONS AND THEIR USES

(75) Inventors: Dov Tamarkin, Maccabim (IL); Doron Friedman, Karmei Yosef (IL); Enbal Ziv, Gedera (IL); Meir Eini, Ness Ziona (IL); Tal Berman, Rishom Lezion (IL); Jorge Danziger, Rishom Lezion (IL); Rita Keynan, Rehovot (IL); David Schuz, Moshav Gimzu (IL)

(73) Assignee: Foamix Ltd., Rehovot (IL)

( * ) Notice: Subject to any disclaimer, the term of this patent is extended or adjusted under 35 U.S.C. 154(b) by 632 days.

This patent is subject to a terminal disclaimer.

(21) Appl. No.: 12/778,591

(22) Filed: May 12, 2010

(65) Prior Publication Data

US 2010/0221195 A1  Sep. 2, 2010

Related U.S. Application Data

(63) Continuation of application No. 12/025,547, filed on Feb. 4, 2008, which is a continuation-in-part of application No. 11/940,290, filed on Nov. 14, 2007.

(60) Provisional application No. 60/899,176, filed on Feb. 2, 2007, provisional application No. 60/915,859, filed on May 3, 2007, provisional application No. 60/858,747, filed on Nov. 14, 2006.

(51) Int. Cl.
*A61Q 19/00* (2006.01)
*A61K 9/12* (2006.01)
*A61K 9/00* (2006.01)
*A61K 47/06* (2006.01)
*A61K 8/04* (2006.01)
*A61K 8/31* (2006.01)
*A61K 9/107* (2006.01)

(52) U.S. Cl.
CPC ............... *A61K 8/046* (2013.01); *A61K 9/122* (2013.01); *A61K 2800/31* (2013.01); *A61K 9/107* (2013.01); *A61K 9/0014* (2013.01); *A61K 47/06* (2013.01); *A61Q 19/00* (2013.01); *A61K 8/31* (2013.01); *Y10S 514/859* (2013.01)
USPC ................. 424/45; 424/43; 514/859

(58) Field of Classification Search
USPC ......................................... 424/45
See application file for complete search history.

(56) References Cited

U.S. PATENT DOCUMENTS 1,159,250 A  11/1915  Moulton
1,666,684 A   4/1928  Carstens (Continued)

FOREIGN PATENT DOCUMENTS

AU  198780257  9/1986
AU       782515  12/2005

(Continued)

OTHER PUBLICATIONS

Sheer—dictionary meaning (vocaburary.com, last visit Aug. 23, 2013).*

(Continued)

*Primary Examiner* — Ernst Arnold
*Assistant Examiner* — Kyung Sook Chang
(74) *Attorney, Agent, or Firm* — Fish & Richardson P.C.

(57) ABSTRACT

The present invention relates to stable substantially non-aqueous, non-alcoholic, non-silicone, foamable carrier compositions comprising petrolatum or mixtures thereof, at least one foam agent, at least one propellant, and with and without the addition of an active agent. The formulations may contain a solvent substantially miscible therein. The present invention further provides a method of treating, alleviating or preventing a disorder of mammalian subject in need thereof, comprising administering the above-mentioned compositions to an afflicted target site of said mammalian subject.

26 Claims, 3 Drawing Sheets

(56) References Cited

U.S. PATENT DOCUMENTS

| | | |
|---|---|---|
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brighttenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienciewicz |
| 3,263,867 A | 8/1966 | Lehmann |
| 3,263,869 A | 8/1966 | Corsette |
| 3,298,919 A | 1/1967 | Charles et al. |
| 3,301,444 A | 1/1967 | Wittke |
| 3,303,970 A | 2/1967 | Breslau et al. |
| 3,330,730 A | 7/1967 | Emil Hernaadez |
| 3,333,333 A | 8/1967 | Noack |
| 3,334,147 A | 8/1967 | Brunelle et al. |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,384,541 A | 5/1968 | Clark et al. |
| 3,395,214 A | 7/1968 | Mummert |
| 3,395,215 A | 7/1968 | Warren |
| 3,401,849 A | 9/1968 | Weber, III |
| 3,419,658 A | 12/1968 | Amsdon |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borocki |
| 3,563,098 A | 2/1971 | Weber, III |
| 3,574,821 A | 4/1971 | Pfirrmann et al. |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackes |
| 3,787,566 A | 1/1974 | Gauvreau |
| 3,819,524 A | 6/1974 | Schubert et al. |
| 3,841,525 A | 10/1974 | Siegel |
| 3,849,580 A | 11/1974 | Weinstein et al. |
| 3,865,275 A | 2/1975 | De Nunzio |
| 3,866,800 A | 2/1975 | Schmitt |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom et al. |
| 4,001,391 A | 1/1977 | Feinstone et al. |
| 4,001,442 A | 1/1977 | Stahlberger et al. |
| 4,018,396 A | 4/1977 | Showmaker et al. |
| 4,019,657 A | 4/1977 | Spitzer et al. |
| 4,052,513 A | 10/1977 | Kaplan |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,178,373 A | 12/1979 | Klein et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,352,808 A | 10/1982 | Rane et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,627,973 A | 12/1986 | Moran et al. |
| 4,628,063 A | 12/1986 | Haines et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |

(56) References Cited

U.S. PATENT DOCUMENTS

| | | |
|---|---|---|
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A * | 1/1991 | Thau .................................. 424/45 |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A * | 10/1993 | Ramirez et al. ............ 424/70.24 |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo Anna Z. et al. |
| 5,384,308 A | 1/1995 | Henkin |
| 5,385,943 A | 1/1995 | Nazzaro-Porro |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A * | 3/1997 | Bloom et al. ................... 424/60 |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |

(56) References Cited

U.S. PATENT DOCUMENTS

| | | | |
|---|---|---|---|
| 5,695,551 A | 12/1997 | Buckingham et al. | |
| 5,700,396 A | 12/1997 | Suzuki et al. | |
| 5,716,611 A | 2/1998 | Oshlack et al. | |
| 5,716,621 A | 2/1998 | Bello | |
| 5,719,122 A | 2/1998 | Chiodini et al. | |
| 5,719,197 A | 2/1998 | Kanios et al. | |
| 5,725,872 A | 3/1998 | Stamm et al. | |
| 5,725,874 A | 3/1998 | Oda | |
| 5,730,964 A | 3/1998 | Waldstreicher | |
| 5,733,558 A | 3/1998 | Breton et al. | |
| 5,733,572 A | 3/1998 | Unger et al. | |
| 5,747,049 A | 5/1998 | Tominaga | |
| 5,753,241 A | 5/1998 | Ribier et al. | |
| 5,753,245 A * | 5/1998 | Fowler et al. | 424/401 |
| 5,759,520 A | 6/1998 | Sachetto | |
| 5,759,579 A | 6/1998 | Singh et al. | |
| 5,767,104 A | 6/1998 | Bar-Shalom et al. | |
| 5,773,410 A | 6/1998 | Yamamoto | |
| 5,783,202 A | 7/1998 | Tomlinson et al. | |
| 5,788,664 A | 8/1998 | Scalise | |
| 5,792,448 A | 8/1998 | Dubief et al. | |
| 5,792,922 A | 8/1998 | Moloney et al. | |
| 5,797,955 A | 8/1998 | Walters | |
| 5,804,546 A | 9/1998 | Hall et al. | |
| 5,807,571 A | 9/1998 | List | |
| 5,817,322 A | 10/1998 | Xu et al. | |
| 5,824,650 A | 10/1998 | De Lacharriere et al. | |
| 5,833,960 A | 11/1998 | Gers-Barlag et al. | |
| 5,833,961 A | 11/1998 | Siegfried et al. | |
| 5,837,270 A | 11/1998 | Burgess | |
| 5,840,744 A | 11/1998 | Borgman | |
| 5,840,771 A | 11/1998 | Oldham et al. | |
| 5,843,411 A | 12/1998 | Hernandez et al. | |
| 5,846,983 A | 12/1998 | Sandborn et al. | |
| 5,849,042 A | 12/1998 | Lim et al. | |
| 5,856,452 A | 1/1999 | Moloney et al. | |
| 5,858,371 A | 1/1999 | Singh et al. | |
| 5,865,347 A | 2/1999 | Welschoff | |
| 5,866,040 A | 2/1999 | Nakama et al. | |
| 5,869,529 A | 2/1999 | Sintov et al. | |
| 5,871,720 A | 2/1999 | Gutierrez et al. | |
| 5,877,216 A | 3/1999 | Place et al. | |
| 5,879,469 A | 3/1999 | Avram et al. | |
| 5,881,493 A | 3/1999 | Restive | |
| 5,885,581 A | 3/1999 | Massand | |
| 5,889,028 A | 3/1999 | Sandborn et al. | |
| 5,889,054 A | 3/1999 | Yu et al. | |
| 5,891,458 A | 4/1999 | Britton et al. | |
| 5,902,574 A | 5/1999 | Stoner et al. | |
| 5,902,789 A | 5/1999 | Stoltz | |
| 5,905,092 A | 5/1999 | Osborne et al. | |
| 5,910,382 A | 6/1999 | Goodenough et al. | |
| 5,911,981 A | 6/1999 | Dahms et al. | |
| 5,912,007 A | 6/1999 | Pan et al. | |
| 5,914,122 A | 6/1999 | Otterbeck et al. | |
| 5,914,310 A | 6/1999 | Li et al. | |
| 5,919,830 A | 7/1999 | Gopalkrishnan et al. | |
| 5,922,331 A | 7/1999 | Mausner | |
| 5,925,669 A | 7/1999 | Katz et al. | |
| 5,948,682 A | 9/1999 | Moloney | |
| 5,951,544 A | 9/1999 | Konwitz | |
| 5,951,989 A | 9/1999 | Heymann | |
| 5,951,993 A | 9/1999 | Scholz et al. | |
| 5,952,373 A | 9/1999 | Lanzendorfer et al. | |
| 5,952,392 A | 9/1999 | Katz et al. | |
| 5,955,414 A | 9/1999 | Brown et al. | |
| 5,959,161 A | 9/1999 | Kenmochi et al. | |
| 5,961,957 A | 10/1999 | McAnalley | |
| 5,961,998 A | 10/1999 | Arnaud et al. | |
| 5,972,310 A | 10/1999 | Sachetto | |
| 5,976,555 A | 11/1999 | Liu et al. | |
| 5,980,904 A | 11/1999 | Leverett et al. | |
| 5,990,100 A | 11/1999 | Rosenberg et al. | |
| 5,993,846 A | 11/1999 | Friedman et al. | |
| 6,001,341 A | 12/1999 | Genova et al. | |
| 6,006,948 A | 12/1999 | Auer | |
| 6,019,967 A | 2/2000 | Breton et al. | |
| 6,024,942 A | 2/2000 | Tanner et al. | |
| 6,030,630 A | 2/2000 | Fleury et al. | |
| 6,033,647 A | 3/2000 | Touzan et al. | |
| 6,039,936 A | 3/2000 | Restle et al. | |
| 6,042,848 A | 3/2000 | Lawyer et al. | |
| 6,045,779 A | 4/2000 | Mueller et al. | |
| 6,071,536 A | 6/2000 | Suzuki et al. | |
| 6,071,541 A | 6/2000 | Murad | |
| 6,075,056 A | 6/2000 | Quigley, Jr. et al. | |
| 6,080,394 A | 6/2000 | Lin et al. | |
| 6,087,317 A | 7/2000 | Gee | |
| 6,090,772 A | 7/2000 | Kaiser et al. | |
| 6,093,408 A | 7/2000 | Hasenoehrl et al. | |
| 6,096,756 A | 8/2000 | Crain et al. | |
| 6,110,477 A | 8/2000 | Hernandez et al. | |
| 6,110,966 A | 8/2000 | Pollock | |
| 6,113,888 A | 9/2000 | Castro et al. | |
| 6,116,466 A | 9/2000 | Gueret | |
| 6,121,210 A | 9/2000 | Taylor | |
| 6,126,920 A | 10/2000 | Jones et al. | |
| 6,140,355 A | 10/2000 | Egidio et al. | |
| 6,146,645 A | 11/2000 | Deckers et al. | |
| 6,146,664 A | 11/2000 | Siddiqui | |
| 6,162,834 A | 12/2000 | Sebillotte-Arnaud et al. | |
| 6,165,455 A | 12/2000 | Torgerson et al. | |
| 6,168,576 B1 | 1/2001 | Reynolds | |
| 6,171,347 B1 | 1/2001 | Kunz et al. | |
| 6,180,669 B1 | 1/2001 | Tamarkin | |
| 6,183,762 B1 | 2/2001 | Deckers et al. | |
| 6,186,367 B1 | 2/2001 | Harrold | |
| 6,187,290 B1 | 2/2001 | Gilchrist et al. | |
| 6,189,810 B1 | 2/2001 | Nerushai et al. | |
| 6,190,365 B1 | 2/2001 | Abbott et al. | |
| 6,204,285 B1 | 3/2001 | Fabiano et al. | |
| 6,210,656 B1 | 4/2001 | Touzan et al. | |
| 6,210,742 B1 | 4/2001 | Deckers et al. | |
| 6,214,318 B1 | 4/2001 | Osipow et al. | |
| 6,214,788 B1 | 4/2001 | Velazco et al. | |
| 6,217,887 B1 | 4/2001 | Beerse et al. | |
| 6,221,381 B1 | 4/2001 | Shelford et al. | |
| 6,221,823 B1 | 4/2001 | Crisanti et al. | |
| 6,224,888 B1 | 5/2001 | Vatter et al. | |
| 6,231,837 B1 | 5/2001 | Stroud et al. | |
| 6,232,315 B1 | 5/2001 | Shafer et al. | |
| 6,251,369 B1 | 6/2001 | Stoltz | |
| 6,258,374 B1 | 7/2001 | Friess et al. | |
| 6,261,544 B1 | 7/2001 | Coury et al. | |
| 6,270,781 B1 | 8/2001 | Gehlsen | |
| 6,271,295 B1 | 8/2001 | Powell et al. | |
| 6,274,150 B1 | 8/2001 | Simonnet et al. | |
| 6,287,546 B1 | 9/2001 | Reich et al. | |
| 6,294,550 B1 | 9/2001 | Place et al. | |
| 6,299,023 B1 | 10/2001 | Arnone | |
| 6,299,032 B1 | 10/2001 | Hamilton | |
| 6,299,900 B1 | 10/2001 | Reed et al. | |
| 6,305,578 B1 | 10/2001 | Hildebrandt et al. | |
| 6,306,841 B1 | 10/2001 | Place et al. | |
| 6,308,863 B1 | 10/2001 | Harman | |
| 6,319,913 B1 | 11/2001 | Mak et al. | |
| 6,328,950 B1 | 12/2001 | Franzke et al. | |
| 6,328,982 B1 | 12/2001 | Shiroyama et al. | |
| 6,333,362 B1 | 12/2001 | Lorant | |
| 6,335,022 B1 | 1/2002 | Simonnet et al. | |
| 6,341,717 B2 | 1/2002 | Auer | |
| 6,344,218 B1 | 2/2002 | Dodd et al. | |
| 6,348,229 B1 | 2/2002 | Eini et al. | |
| 6,355,230 B2 | 3/2002 | Gers-Barlag et al. | |
| 6,358,541 B1 | 3/2002 | Goodman | |
| 6,358,924 B1 | 3/2002 | Hoffmann | |
| 6,364,854 B1 | 4/2002 | Ferrer et al. | |
| 6,372,234 B1 | 4/2002 | Deckers et al. | |
| 6,375,960 B1 | 4/2002 | Simonnet et al. | |
| 6,383,471 B1 | 5/2002 | Chen et al. | |
| 6,395,258 B1 | 5/2002 | Steer | |
| 6,395,300 B1 | 5/2002 | Straub et al. | |
| 6,403,061 B1 | 6/2002 | Candau et al. | |
| 6,403,069 B1 | 6/2002 | Chopra et al. | |

(56) References Cited

U.S. PATENT DOCUMENTS

| | | |
|---|---|---|
| 6,410,036 B1 | 6/2002 | De Rosa et al. |
| 6,423,323 B2 | 7/2002 | Neubourg |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,451,777 B1 | 9/2002 | Bradbury et al. |
| 6,455,076 B1 | 9/2002 | Hahn et al. |
| 6,468,989 B1 | 10/2002 | Chang et al. |
| 6,479,058 B1 | 11/2002 | McCadden |
| 6,479,532 B1 | 11/2002 | Kamimura et al. |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,682,750 B2 | 1/2004 | Loeffler et al. |
| 6,691,898 B2 | 2/2004 | Hurray et al. |
| 6,709,663 B2 | 3/2004 | Espinoza |
| 6,723,309 B1 | 4/2004 | Deane |
| 6,730,288 B1 | 5/2004 | Abram |
| 6,753,000 B2 | 6/2004 | Breton et al. |
| 6,753,013 B1 | 6/2004 | Didriksen et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,897,195 B2 | 5/2005 | Su et al. |
| 6,902,737 B2 | 6/2005 | Quemin et al. |
| 6,911,211 B2 | 6/2005 | Eini et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Mekata |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,758,888 B2 | 7/2010 | Lapidot et al. |
| 7,793,807 B2 | 9/2010 | Goujon et al. |
| 7,820,145 B2 | 10/2010 | Tamarkin et al. |
| 7,960,416 B2 | 6/2011 | Sato et al. |
| 8,158,109 B2 | 4/2012 | Abram et al. |
| 8,343,945 B2 | 1/2013 | Tamarkin et al. |
| 8,362,091 B2 | 1/2013 | Tamarkin et al. |
| 8,435,498 B2 | 5/2013 | Tamarkin et al. |
| 8,486,375 B2 | 7/2013 | Tamarkin et al. |
| 8,518,376 B2 | 8/2013 | Tamarkin et al. |
| 8,618,081 B2 | 12/2013 | Tamarkin et al. |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0036450 A1 | 11/2001 | Verite et al. |
| 2001/0054574 A1 | 12/2001 | Navarro |
| 2002/0002151 A1 | 1/2002 | Ono et al. |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Haslwanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0122811 A1 | 9/2002 | Stein et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0187181 A1 | 12/2002 | Godbey et al. |
| 2002/0198136 A1 | 12/2002 | Mak et al. |
| 2003/0006654 A1 | 1/2003 | Ikeda et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0078172 A1 | 4/2003 | Guiramand et al. |
| 2003/0108502 A1 | 6/2003 | Uchida et al. |
| 2003/0114520 A1 | 6/2003 | Pereira et al. |
| 2003/0118515 A1 | 6/2003 | Jew et al. |
| 2003/0130247 A1 | 7/2003 | Gans et al. |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |

(56) References Cited

U.S. PATENT DOCUMENTS

| | | |
|---|---|---|
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215472 A1 | 11/2003 | Bonda et al. |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1* | 9/2004 | Abram ............ 424/45 |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0219122 A1 | 11/2004 | Masuda et al. |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0253275 A1 | 12/2004 | Eini et al. |
| 2004/0258627 A1 | 12/2004 | Riedel et al. |
| 2004/0258628 A1 | 12/2004 | Riedel et al. |
| 2004/0265240 A1 | 12/2004 | Tamarkin et al. |
| 2005/0002976 A1 | 1/2005 | Wu |
| 2005/0013853 A1 | 1/2005 | Gil-Ad et al. |
| 2005/0031547 A1 | 2/2005 | Tamarkin et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0084551 A1 | 4/2005 | Jensen et al. |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281749 A1* | 12/2005 | Willcox et al. ............ 424/45 |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Meketa |
| 2006/0057168 A1 | 3/2006 | Larm et al. |
| 2006/0088561 A1 | 4/2006 | Eini et al. |
| 2006/0099151 A1 | 5/2006 | Neubourg |
| 2006/0108377 A1 | 5/2006 | Glynn et al. |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0010580 A1 | 1/2007 | De Paoli Ambrosi |
| 2007/0017696 A1 | 1/2007 | Lin et al. |
| 2007/0020213 A1 | 1/2007 | Tamarkin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0134174 A1 | 6/2007 | Irwin et al. |
| 2007/0140999 A1 | 6/2007 | Puglia et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0224143 A1 | 9/2007 | Konis |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0271235 A1 | 11/2007 | Frank et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |

(56) References Cited

U.S. PATENT DOCUMENTS

| | | | |
|---|---|---|---|
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0041680 A1 | 2/2009 | Tamarkin et al. |
| 2009/0053290 A1 | 2/2009 | Sand et al. |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0180970 A1 | 7/2009 | Tamarkin et al. |
| 2009/0291917 A1 | 11/2009 | Akama et al. |
| 2009/0317338 A1 | 12/2009 | Tamarkin et al. |
| 2010/0111879 A1 | 5/2010 | Tamarkin et al. |
| 2010/0137198 A1 | 6/2010 | Eini et al. |
| 2010/0221194 A1 | 9/2010 | Loupenok |
| 2010/0221195 A1 | 9/2010 | Tamarkin et al. |
| 2010/0266510 A1 | 10/2010 | Tamarkin et al. |
| 2011/0002857 A1 | 1/2011 | Tamarkin et al. |
| 2011/0002969 A1 | 1/2011 | Serraima et al. |
| 2011/0008266 A1 | 1/2011 | Tamarkin et al. |
| 2011/0045037 A1 | 2/2011 | Tamarkin et al. |
| 2011/0097279 A1 | 4/2011 | Tamarkin et al. |
| 2011/0212033 A1 | 9/2011 | Tamarkin et al. |
| 2011/0268665 A1 | 11/2011 | Tamarkin et al. |
| 2012/0064136 A1 | 3/2012 | Baker, Jr. et al. |
| 2012/0087872 A1 | 4/2012 | Tamarkin et al. |
| 2012/0128598 A1 | 5/2012 | Trumbore et al. |
| 2012/0148503 A1 | 6/2012 | Tamarkin et al. |
| 2012/0156144 A1 | 6/2012 | Tamarkin et al. |
| 2012/0195836 A1 | 8/2012 | Tamarkin et al. |
| 2012/0213709 A1 | 8/2012 | Tamarkin et al. |
| 2012/0213710 A1 | 8/2012 | Tamarkin et al. |
| 2012/0237453 A1 | 9/2012 | Tamarkin et al. |
| 2013/0011342 A1 | 1/2013 | Tamarkin et al. |
| 2013/0028850 A1 | 1/2013 | Tamarkin et al. |
| 2013/0053353 A1 | 2/2013 | Tamarkin et al. |
| 2013/0064777 A1 | 3/2013 | Tamarkin et al. |
| 2013/0161351 A1 | 6/2013 | Eini et al. |
| 2013/0164225 A1 | 6/2013 | Tamarkin et al. |
| 2013/0183250 A1 | 7/2013 | Friedman et al. |
| 2013/0183251 A1 | 7/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0189196 A1 | 7/2013 | Tamarkin et al. |
| 2013/0195769 A1 | 8/2013 | Tamarkin et al. |
| 2013/0225536 A1 | 8/2013 | Tamarkin et al. |
| 2013/0295022 A1 | 11/2013 | Friedman et al. |
| 2014/0050673 A1 | 2/2014 | Tamarkin et al. |

FOREIGN PATENT DOCUMENTS

| | | | |
|---|---|---|---|
| AU | 2010219295 | | 9/2012 |
| CA | 2154438 | | 1/1996 |
| CA | 2422244 | | 9/2003 |
| CA | 2502986 | | 8/2011 |
| CA | 2534372 | | 1/2012 |
| CA | 2536482 | | 7/2012 |
| CH | 639913 | | 12/1983 |
| DE | 933486 | C | 9/1955 |
| DE | 1 882 100 | | 11/1963 |
| DE | 1926796 | | 11/1965 |
| DE | 4140474 | | 6/1993 |
| DE | 10009233 | | 8/2000 |
| DE | 10138495 | A1 | 2/2003 |
| DE | 102004016710 | | 10/2005 |
| DE | 2 608 226 | | 9/2007 |
| EP | 0156507 | A1 | 10/1985 |
| EP | 0 186 453 | | 7/1986 |
| EP | 0186453 | | 7/1986 |
| EP | 211550 | | 2/1987 |
| EP | 0214865 | A2 | 3/1987 |
| EP | 0 216 856 | | 4/1987 |
| EP | 0270316 | | 6/1988 |
| EP | 270316 | A2 | 6/1988 |
| EP | 297436 | | 1/1989 |
| EP | 0 326 196 | | 8/1989 |
| EP | 0 336 812 | | 10/1989 |
| EP | 0 391 124 | | 10/1990 |
| EP | 0404376 | | 12/1990 |
| EP | 414920 | | 3/1991 |
| EP | 0 485 299 | | 5/1992 |
| EP | 0484530 | A1 | 5/1992 |
| EP | 0488089 | A1 | 6/1992 |
| EP | 0 504 301 | | 9/1992 |
| EP | 0 528 190 | | 2/1993 |
| EP | 0535327 | A1 | 4/1993 |
| EP | 0 552 612 | | 7/1993 |
| EP | 0569773 | A2 | 11/1993 |
| EP | 0598412 | A2 | 5/1994 |
| EP | 0 662 431 | | 7/1995 |
| EP | 0676198 | | 10/1995 |
| EP | 0738516 | A1 | 10/1996 |
| EP | 0 757 959 | | 2/1997 |
| EP | 0824911 | | 2/1998 |
| EP | 0 829 259 | | 3/1998 |
| EP | 0 928 608 | | 7/1999 |
| EP | 0979654 | A1 | 2/2000 |
| EP | 0993827 | A1 | 4/2000 |
| EP | 1 025 836 | | 8/2000 |
| EP | 1055425 | A2 | 11/2000 |
| EP | 0 506 197 | | 7/2001 |
| EP | 1215258 | | 6/2002 |
| EP | 1287813 | | 3/2003 |
| EP | 1 308 169 | | 5/2003 |
| EP | 1 375 386 | | 1/2004 |
| EP | 1428521 | | 6/2004 |
| EP | 1438946 | | 7/2004 |
| EP | 1189579 | | 9/2004 |
| EP | 1475381 | | 11/2004 |
| EP | 1 483 001 | | 12/2004 |
| EP | 1500385 | | 1/2005 |
| EP | 1 537 916 | | 6/2005 |
| EP | 1 600 185 | | 11/2005 |
| EP | 1 734 927 | | 12/2006 |
| EP | 1758547 | | 3/2007 |
| EP | 1584324 | | 11/2007 |
| EP | 1 889 609 | | 2/2008 |
| EP | 2422768 | | 2/2012 |
| EP | 2494959 | | 9/2012 |
| FR | 2 591 331 | | 6/1987 |
| FR | 2 640 942 | | 6/1990 |
| FR | 2 736 824 | | 1/1997 |
| FR | 2774595 | A | 8/1999 |
| FR | 2 789 371 | | 8/2000 |
| FR | 2 793 479 | | 11/2000 |
| FR | 2 814 959 | | 4/2002 |
| FR | 2 833 246 | | 6/2003 |
| FR | 2 840 903 | | 12/2003 |
| FR | 2 843 373 | | 2/2004 |
| FR | 2 845 672 | | 4/2004 |
| FR | 2 848 998 | | 6/2004 |
| FR | 2 860 976 | | 4/2005 |
| FR | 2 915 891 | | 11/2008 |
| FR | 2915891 | | 11/2008 |
| GB | 808104 | | 1/1959 |

(56) References Cited

FOREIGN PATENT DOCUMENTS

| | | |
|---|---|---|
| GB | 808105 A | 1/1959 |
| GB | 922930 | 4/1963 |
| GB | 933 486 | 8/1963 |
| GB | 998 490 | 7/1965 |
| GB | 1026831 | 4/1966 |
| GB | 1 033 299 | 6/1966 |
| GB | 1 081 949 | 9/1967 |
| GB | 1121358 | 7/1968 |
| GB | 1 162 684 | 8/1969 |
| GB | 1 170 152 | 11/1969 |
| GB | 1 201 918 | 8/1970 |
| GB | 1 347 950 | 2/1974 |
| GB | 1 351 761 | 5/1974 |
| GB | 1 351 762 | 5/1974 |
| GB | 1 353 381 | 5/1974 |
| GB | 1376649 | 12/1974 |
| GB | 1397285 | 6/1975 |
| GB | 1 408 036 | 10/1975 |
| GB | 1 457 671 | 12/1976 |
| GB | 1 489 672 | 10/1977 |
| GB | 2 004 746 | 4/1979 |
| GB | 1 561 423 | 2/1980 |
| GB | 2114580 | 8/1983 |
| GB | 2 153 686 | 8/1985 |
| GB | 2 172 298 | 9/1986 |
| GB | 2 206 099 | 12/1988 |
| GB | 2166651 | 5/1996 |
| GB | 2337461 | 11/1999 |
| GB | 2 367 809 | 4/2002 |
| GB | 2 406 330 | 3/2005 |
| GB | 2 406 791 | 4/2005 |
| GB | 2474930 | 7/2012 |
| IL | 49491 | 9/1979 |
| IL | 0152486 | 5/2003 |
| JP | 60001113 | 4/1978 |
| JP | 55069682 | 5/1980 |
| JP | 57044429 | 3/1982 |
| JP | 56039815 | 4/1984 |
| JP | 61275395 | 12/1986 |
| JP | 62241701 | 10/1987 |
| JP | 63119420 | 5/1988 |
| JP | 01100111 | 4/1989 |
| JP | 01156906 | 6/1989 |
| JP | 2184614 | 7/1990 |
| JP | 02184614 A | 7/1990 |
| JP | 2255890 | 10/1990 |
| JP | 04282311 | 10/1992 |
| JP | 4312521 | 11/1992 |
| JP | 5070340 | 3/1993 |
| JP | 5213734 | 8/1993 |
| JP | 6100414 | 4/1994 |
| JP | H06-263630 | 6/1994 |
| JP | 6329532 | 11/1994 |
| JP | 2007/155667 | 6/1995 |
| JP | 7215835 | 8/1995 |
| JP | 8501529 | 2/1996 |
| JP | 2008040899 | 2/1996 |
| JP | 8119831 | 5/1996 |
| JP | 8165218 | 6/1996 |
| JP | 8277209 | 10/1996 |
| JP | 09 084855 | 3/1997 |
| JP | 9099553 | 4/1997 |
| JP | 9110636 | 4/1997 |
| JP | 10114619 | 5/1998 |
| JP | 3050289 | 9/1998 |
| JP | 2010/332456 | 12/1998 |
| JP | 11501045 | 1/1999 |
| JP | 11250543 | 9/1999 |
| JP | 2000017174 A | 1/2000 |
| JP | 2000080017 | 3/2000 |
| JP | 2000128734 | 5/2000 |
| JP | 2000191429 | 7/2000 |
| JP | 2000/239140 | 9/2000 |
| JP | 2000/354623 | 12/2000 |
| JP | 2000351726 | 12/2000 |
| JP | 2001/002526 | 1/2001 |
| JP | 2001019606 | 1/2001 |
| JP | 2001072963 | 3/2001 |
| JP | 2002012513 | 1/2002 |
| JP | 2002047136 | 2/2002 |
| JP | 2002/524490 | 8/2002 |
| JP | 2002/302419 | 10/2002 |
| JP | 2003/012511 | 1/2003 |
| JP | 2003055146 | 2/2003 |
| JP | 2004047136 A | 2/2004 |
| JP | 2004/250435 | 9/2004 |
| JP | 2004/348277 | 12/2004 |
| JP | 2005/314323 | 11/2005 |
| JP | 2005350378 | 12/2005 |
| JP | 2006008574 | 1/2006 |
| JP | 2006/036317 | 2/2006 |
| JP | 2006/103799 | 4/2006 |
| JP | 2006525145 | 11/2006 |
| JP | 2007131539 | 5/2007 |
| JP | 2007326996 | 12/2007 |
| KR | 143232 | 7/1998 |
| KR | 2001/003063 | 1/2001 |
| NZ | 520014 | 5/2005 |
| NZ | 540166 | 6/2007 |
| RU | 2277501 | 6/2006 |
| UA | 66796 | 6/2004 |
| WO | 82/01821 | 6/1982 |
| WO | WO-8605389 A1 | 9/1986 |
| WO | 88/01502 | 3/1988 |
| WO | WO-8801863 A1 | 3/1988 |
| WO | 88/08316 | 11/1988 |
| WO | WO-8906537 A1 | 7/1989 |
| WO | WO-9005774 A1 | 5/1990 |
| WO | WO-9111991 | 8/1991 |
| WO | WO-9200077 A1 | 1/1992 |
| WO | 92/05142 | 4/1992 |
| WO | 92/05763 | 4/1992 |
| WO | WO-9211839 A1 | 7/1992 |
| WO | 93/25189 | 12/1993 |
| WO | 94/06440 | 3/1994 |
| WO | WO-9603115 A1 | 2/1996 |
| WO | WO-9619921 A1 | 7/1996 |
| WO | WO-9624325 A1 | 8/1996 |
| WO | 96/26711 | 9/1996 |
| WO | WO-9627376 A1 | 9/1996 |
| WO | WO-9639119 A1 | 12/1996 |
| WO | 97/03638 | 2/1997 |
| WO | WO-9739745 A1 | 10/1997 |
| WO | 98/17282 | 4/1998 |
| WO | WO-9818472 A1 | 5/1998 |
| WO | WO-9819654 A1 | 5/1998 |
| WO | WO-9821955 A1 | 5/1998 |
| WO | WO-9823291 A1 | 6/1998 |
| WO | WO-9836733 A2 | 8/1998 |
| WO | 98/52536 | 11/1998 |
| WO | WO-9908649 A2 | 2/1999 |
| WO | WO-9920250 A1 | 4/1999 |
| WO | WO-9937282 A2 | 7/1999 |
| WO | 99/53923 | 10/1999 |
| WO | WO-0009082 A1 | 2/2000 |
| WO | WO-0015193 A1 | 3/2000 |
| WO | 00/23051 | 4/2000 |
| WO | WO 00/62776 | 4/2000 |
| WO | 00/33825 | 6/2000 |
| WO | 00/38731 | 7/2000 |
| WO | WO-0061076 A1 | 10/2000 |
| WO | WO 00/72805 | 12/2000 |
| WO | WO-0076461 A2 | 12/2000 |
| WO | 01/05366 | 1/2001 |
| WO | 01/10961 | 2/2001 |
| WO | WO-0108681 A1 | 2/2001 |
| WO | 01/53198 | 7/2001 |
| WO | 01/54212 | 7/2001 |
| WO | 01/62209 | 8/2001 |
| WO | WO-0154679 A2 | 8/2001 |
| WO | WO-0170242 A2 | 9/2001 |
| WO | 01/82890 | 11/2001 |
| WO | 01/85102 | 11/2001 |
| WO | 01/85128 | 11/2001 |

(56) References Cited

FOREIGN PATENT DOCUMENTS

| | | |
|---|---|---|
| WO | WO-0182880 A2 | 11/2001 |
| WO | 01/95728 | 12/2001 |
| WO | WO-0200820 A1 | 1/2002 |
| WO | 02/15860 | 2/2002 |
| WO | 02/15873 | 2/2002 |
| WO | WO-0228435 A1 | 4/2002 |
| WO | WO-0241847 A1 | 5/2002 |
| WO | WO-0243490 A1 | 6/2002 |
| WO | WO-02062324 A2 | 8/2002 |
| WO | 02/078667 | 10/2002 |
| WO | 02/087519 | 11/2002 |
| WO | 03/002082 | 1/2003 |
| WO | WO-03000223 A1 | 1/2003 |
| WO | 03/013984 | 2/2003 |
| WO | WO-03051294 | 6/2003 |
| WO | WO-03051294 A2 | 6/2003 |
| WO | 03/055454 | 7/2003 |
| WO | WO-03053292 A1 | 7/2003 |
| WO | WO-03055445 A2 | 7/2003 |
| WO | 03/070301 | 8/2003 |
| WO | 03/071995 | 9/2003 |
| WO | WO-03075851 | 9/2003 |
| WO | WO-03075851 A2 | 9/2003 |
| WO | 03/097002 | 11/2003 |
| WO | WO-03092641 A1 | 11/2003 |
| WO | 2004/017962 | 3/2004 |
| WO | 2004/037197 | 5/2004 |
| WO | WO-2004037225 A2 | 5/2004 |
| WO | 2004/003284 | 8/2004 |
| WO | 2004/064769 | 8/2004 |
| WO | WO-2004064833 A1 | 8/2004 |
| WO | WO-2004071479 A1 | 8/2004 |
| WO | 2004/078158 | 9/2004 |
| WO | WO-2004078896 A1 | 9/2004 |
| WO | 2004/093895 | 11/2004 |
| WO | WO-2004112780 A1 | 12/2004 |
| WO | WO-2005011567 A2 | 2/2005 |
| WO | WO-2005018530 A2 | 3/2005 |
| WO | WO-2005032522 A1 | 4/2005 |
| WO | WO-2005044219 A1 | 5/2005 |
| WO | 2005/063224 | 7/2005 |
| WO | WO-2005065652 A1 | 7/2005 |
| WO | WO-2005076697 | 8/2005 |
| WO | WO-2005076697 A2 | 8/2005 |
| WO | WO-2005/097068 A1 | 10/2005 |
| WO | WO-2005097068 A1 | 10/2005 |
| WO | 2005/102282 | 11/2005 |
| WO | WO-2005102539 A1 | 11/2005 |
| WO | WO-2005117813 A1 | 12/2005 |
| WO | WO-2006003481 A2 | 1/2006 |
| WO | 2006/011046 | 2/2006 |
| WO | WO-2006010589 A2 | 2/2006 |
| WO | WO-2006020682 A1 | 2/2006 |
| WO | 2006/028339 | 3/2006 |
| WO | WO-2006031271 A2 | 3/2006 |
| WO | 2006/045170 | 5/2006 |
| WO | 2006/079632 | 8/2006 |
| WO | 2006/081327 | 8/2006 |
| WO | WO-2006091229 A2 | 8/2006 |
| WO | WO-2006100485 A1 | 9/2006 |
| WO | 2006/121610 | 11/2006 |
| WO | 2006/122158 | 11/2006 |
| WO | WO-2006120682 A2 | 11/2006 |
| WO | WO-2006129161 A2 | 12/2006 |
| WO | WO-2006131784 A1 | 12/2006 |
| WO | WO 2007/010494 | 1/2007 |
| WO | WO-2007007208 A2 | 1/2007 |
| WO | WO-2007012977 A2 | 2/2007 |
| WO | WO-2007023396 A2 | 3/2007 |
| WO | WO-2007031621 A2 | 3/2007 |
| WO | WO-2007039825 A2 | 4/2007 |
| WO | WO-2007050543 A2 | 5/2007 |
| WO | WO-2007054818 A2 | 5/2007 |
| WO | WO-2007072216 A2 | 6/2007 |
| WO | WO 2007/082698 | 7/2007 |
| WO | WO-2007085899 A2 | 8/2007 |
| WO | WO-2007085902 A2 | 8/2007 |
| WO | WO-2007099396 A2 | 9/2007 |
| WO | 2007/111962 | 10/2007 |
| WO | 2008/010963 | 1/2008 |
| WO | WO-2008008397 A2 | 1/2008 |
| WO | 2008/041045 | 4/2008 |
| WO | WO-2008038147 A2 | 4/2008 |
| WO | WO-2008075207 A2 | 6/2008 |
| WO | WO-2008087148 A2 | 7/2008 |
| WO | WO-2008110872 A2 | 9/2008 |
| WO | 2008/152444 | 12/2008 |
| WO | WO-2009007785 A2 | 1/2009 |
| WO | WO-2009069006 A2 | 6/2009 |
| WO | WO-2009072007 A2 | 6/2009 |
| WO | WO-2009087578 A2 | 7/2009 |
| WO | WO-2009090495 A2 | 7/2009 |
| WO | WO-2009090558 A2 | 7/2009 |
| WO | WO-2009098595 A2 | 8/2009 |
| WO | 2011/039637 | 4/2011 |
| WO | 2011/039638 | 4/2011 |
| WO | WO 2011/138678 | 11/2011 |
| WO | WO 2013/136192 | 9/2013 |

OTHER PUBLICATIONS

Shear—dictionary meaning (vocaburary.com, last visit Aug. 23, 2013).*
*Sun Pharmaceutical Industries Ltd.* v. *Eli Lilly and Co.*, 611 F.3d 1381, 95 USPQ2d 1797 (Fed. Cir. 2010), 7 pages.*
*Molins PLC* v. *Textron Inc.*, 48 F.3d 1172, 33 USPQ2d 1823 (Fed. Cir. 1995), 19 pages.*
Vishnupad et al., CA 1,290,689 C (international class A61K-7/50; A61K-47/44), 13 pages, (1991).*
U.S. Appl. No. 60/789,186, filed Apr. 4, 2006, Tamarkin.
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
U.S. Appl. No. 61/322,148, filed Apr. 8, 2010, Tamarkin.
U.S. Appl. No. 61/363,577, filed Jul. 12, 2010, Eini.
"Burn patients need vitamin D supplements." *Decision News Media*, Jan. 23, 2004, http://www.nutraingredients.com/Research/Burn-patients-need-vitamin-D-supplements, Accessed: May 5, 2010.
"Minocycline" accessed on Ocotober 21, 2011 at en.wikipedia.org/wiki/Minocycline, 7 pages.
"Reaction Rate" Accessed at en.wikipedia.org/wiki/Reaction_rate on Dec. 18, 2011, 6 pages.
'Niram Chemicals' [online]. Niram Chemicals, [retrieved on Jul. 17, 2012]. Retrieved from the Internet: <URL: http://www.indiamart.com/niramchemicals/chemicals.html>, 7 pages.
'Surfactant' [online]. Wikipedia, 2010, [retrieved on Oct. 24, 2010]. Retrieved from the Internet: <URL: http://en.wikipedia.org/wiki/Surfactant>, 7 pages.
Adachi, Shuji. "Storage and Oxidative Stability of O/W/ Nano-emulsions." Foods Food Ingredients. J. Jpn. vol. 209, No. 11. 2004. 1 page.
Anton, N. et al. "Water-in-Oil Nano-Emulsion Formation by the phase inversion Method: A Novel and General Concept, a New Template for Nanoencapsulation," *Proceedings of the 33rd Annual Meeting and Exposition of the Controlled Release Society*, Jul. 2006, Vienna, Austria, 2 pages.
Arct et al., "Common Cosmetic Hydrophilic Ingredients as Penetration Modifiers of Flavonoids", International Journal of Cosmetic Science, 24(6):357-366 (2002)—Abstract, 1 page.
Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.
Austria, et al., "Stability of Vitamin C Derivatives in Solution and Topical Formulations", Journal of Pharmaceutical and Biomedical Analysis, 15:795-801 (1997).
Barry and Badal, "Stability of minocycline, doxycycline, and tetracycline stored in agar plates and microdilution trays," *Current Microbiology*, 1978, 1:33-36.

(56) References Cited

OTHER PUBLICATIONS

Bernstein, et al., Effects of the Immunomodulating Agent R837 on Acute and Latent Herpes Simplex Virus Type 2 Invections, Antimicrobial Agents and Chemotherapy, 33(9):1511-1515 (1989).

Blute, "Phase behavior of alkyl glycerol ether surfacants", Physical Chemistry Tenside Sur. Det., 35(3):207-212 (1998).

Brenes, et al., "Stability of Copigmented Anthocyanins and Asorbics Acid in a Grape Juice Model System", J. Agric Food Chem, 53(1):49-56 (2005)—Abstrace, 1 page.

Bronopol. Revtrieved online on Jun. 4, 2011. <URL:http://chemicalland21.com/specialtychem/perchem/BRONOPOL.html>. Jul. 17, 2006. 4 pages.

Buck, et al., "Treatment of Vaginal Intraephithelial Neoplasia (Primarily Low Grade) with Imiquimod 5% Cream", Journal of Lower Genetial Tract Disease, 7(3):290-293 (2003).

Bunker,et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).

Burton, et al., "Hypertrichosis Due to Minoxidil", British Journal of Dermatology, 101:593-595 (1979).

Campos, et al., "Ascorbic Acid and Its Derivatives in Cosmetic Formulations", Cosmetics and Toiletries, 115(6):59-62 (2000)—Abstract, 1 page.

Carelli, et al., "Effect of Vehicles on Yohimbine Permeation Across Excised Hairless Mouse Skin", Pharm Acta Helv, 73(3):127-134 (1998)—Abstract, 1 page.

Chevrant-Breton, et al., "Etude du Traitement Capillaire <<Bioscalin>> dans les Alopecies Diffuses de la Femme", Gazette Medicale, 93(17):75-79 (1986) [English abstract].

Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.

Chinnian, et al., "Photostability Profiles of Minoxidil Solutions", PDA J. Pharm Sci Technol., 50(2):94-98 (1996)—Abstract, 1 page.

Chollet, et al., "Development of a Topically Active Imiquimod Formulation", Pharmaceutical Development and Technology, 4(1):35-43 (1999).

Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.

Colloidal Silica. Retrieved online on Jun. 4, 2011. <URL:http://www.grace.com/engineeredmaterials/materialsciences/colloidalsilica/default.aspx>. Copyright 2011. 4 pages.

Croda 2. Croda Cetomacrogol 1000 Product Information Sheet. 2011 (no month given). 1 page.

Croda. Aracel 165 Product Summary. 2011 (no month given). 1 page.

Dawber, et al., "Hypertrichosis in Females Applying Minoxidil Topical Solution and in Normal Controls", JEADV, 17:271-275 (2003).

Dentinger, et al., "Stability of Nifedipine in an Extemporaneously Compounded Oral Solution", American Journal of Health-System Pharmacy, 60(10):1019-1022 (2003)—Abstract, 1 page.

Draelos, Z. D. "Antiperspirants and the Hyperhidrosis Patients." Dermatologic Therapy. 2001. vol. 14. pp. 220-224.

Edens, et al., "Storage Stability and Safey of Active Vitamin C in a New Dual-Chamber Dispenser", Journal of Applied Cosmetology, 17(4):136-143 (1999)—Abstract, 1 page.

Edwards, "Imiquimod in Clinical Practice", J. Am Acad Dermatol., 43(1, Pt 2):512-517 (2000)—Abstract, 1 page.

Esposito, E. et al. "Nanosystems for Skin Hydration: A Comparative Study." International Journal of Cosmetic Science. 29. 2007. pp. 39-47.

Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.

Farahmand, et al., "Formulation and Evaluation of a Vitamin C Multiple Emulsion", Pharmaceutical Development and Technology, 11(2):255-261 (2006)—Abstract, 1 page.

Chebil, et al., "Soulbility of Flavonoids in Organic Solvents", J. Chem. Eng. Data, 52(5):1552-1556 (2007)—Abstract, 1 page.

Gallarate, et al., "On the Stability of Ascorbic Acid in Emulsified Systems for Topical and Cosmetic Use", International Journal of Pharmaceutics, 188:233-241 (1999).

Gelbard et al. "Primary Pediatric Hyperhidrosis: A Review of Current Treatment Options." Pediatric Dermatology. 2008. 25 (6). pp. 591-598.

Gladkikh, "Ascorbic Acid and Methods of Increasing its Stability in Drugs", Translated from Khimiko-Farmatsevticheskii Zhurnal, 4(12):37-42 (1970)—1 page.

Graves, S. et al. "Structure of Concentrated Nanoemulsions." The Journal of Chemical Physics. Published Apr. 1, 2005. 6 pages.

Groveman, et al., "Lack of Efficacy of Polysorbate 60 in the Treatment of Male Pattern Baldness", Arch Intern Med, 145:1454-1458 (1985).

Hallstar. Retrieved online on Jun. 4, 2011. <URL:http://www.hallstar.com/pis.php?product=1H022>. 1 page.

Hargreaves, "Chemical Formulation, An Overview of Surfactant-Based Preparations Used in Everyday Life", *The Royal Society of Chemistry*, pp. 114-115 (2003).

Harrison, et al., "Effects of cytokines and R-837, a cytokine inducer, on UV-irradiation augmented recurrent genital herpes in guinea pigs", Antiviral Res., 15(4):315-322 (1991).

Harrison, et al., "Modification of Immunological Responses and Clinical Disease During Topical R-837 Treatment of Genital HSV-2 Infection", Antiviral Research, 10:209-224 (1988).

Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.

Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).

Hormones. Http://www.greenwillowtree.com/Page.bok?file=libido.html. Jan. 2001.

Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.

ICI Americas Inc. "The HLB System: A Time-Saving Guide to Emulsifier Selection." Mar. 1980. pp. 1-22.

Ikuta, et al., "Scanning Electron Microscopic Observation of Oil/Wax/Water/Surfacant System", Journal of SCCJ, 34(4):280-291 (2004)—Abstract, 1 page.

Indomethacin. Retrieved online on Jun. 3, 2011. <URL:http://it03.net/com/oxymatrine/down/1249534834.pdf>. Aug. 15, 2009. 3 pages.

Izquierdo, P. et al. "Formation and Stability of Nano-Emulsions Prepared Using the Phase Inversion Temperature Method." University of Barcelona. Sep. 17, 2001. 1 page.

Jan. "Troubled Times: Detergent Foam." http://zetatalk.com/health/theall7c.htm. Accessed Feb. 9, 2012. 2 pages.

Joseph, "Understanding foams & foaming," University of Minnesota (1997), at http://www.aem.umn.edu/people/faculty/joseph/archive/docs/understandingfoams.pdf, pp. 1-8.

Kang,et al., "Enhancement of the Stability and Skin Penetration of Vitamin C by Polyphenol", Immune Netw., 4(4):250-254 (2004)—Abstract, 1 page.

Kim, "Stability of Minoxidil in Aqueous Solution", Yakhak Hoechi, 30(5):228-231 (1986)—Abstract, 1 page.

Kwak et al. "Study of Complete Transparent Nano-Emulsions which Contain Oils." IFSCC Conference 2003, Seoul, Korea, Sep. 22-24, 2003. 3 pages.

Lautenschlager, Dr. Hans. "A Closer Look on Natural Agents: Facts and Future Aspects." Kosmetic Konzept. Kosmetische Praxis. 2006 (no month given). (5), 8-10. 3 pages.

Lebwohl et al. "Treatment of Psoriasis. Part 1. Topical Therapy and Phototherapy." *J. Am. Acad. Dermatol*. 45:487-498. Oct. 2001.

(56) References Cited

OTHER PUBLICATIONS

Lebwohl et al., "A randomized, double-blind, placebo-controlled study of clobestasol propionate 0.05% foam in the treatment of nonscalp psoriasis," *International Journal of Dermatology*, 2002, 41(5): 269-274.

Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).

Li, et al., "Solubility Behavior of Imiquimod in Alkanoic Acids", Abstract 3029, Pharmaceutical Research, vol. 14, No. 11 Supplemental (November), p. S475 (1997), 2 pages.

Lippacher, A. et al. "Liquid and Semisolid SLN Dispersions for Topical Application Rheological Characterization." European Journal of Pharmaceutics and Biopharmaceutics. 58. 2004. pp. 561-567.

Lupo, "Antioxidants and Vitamins in Cosmetics", Clinics in Dermatology, 19:467-473 (2001).

Martindale. 33 ed. London, Bath Press, 2002. pp. 1073 and 1473.

Merck index, 10th edition, Merck & Co., Inc.: Rahway, NJ, 1983, pp. 39 (entry 242 for allantoin).

Merck index, 14th edition, O'Neill, ed., 2006, entry for p-amino benzoic acid.

Merck index, 14th edition, O'Neill, ed., 2006, entry for zinc oxide.

Merck Index, An Encyclopedia of Chemicals, Drugs, and Biologicals. $13^{th}$ Edition. O'Neil et al eds. Entries 1058, 2350, 6143, and 8803. 2001. 7 pages.

Merck Manual Home Edition. "Excessive Sweating: Sweating Disorders." Accessed Apr. 14, 2011 at www.merckmanuals.com/home/print/sec18/ch206/ch206c.html. 2 pages.

Messenger, et al., "Minoxidil: Mechanisms of Action on Hair Growth", British Journal of Dermatology, 150:186-194 (2004).

Metz, et al., "A Phase I Study of Topical Tempol for the Prevention of Alopecia Induced by Whole Brain Radiotherapy", Clinical Cancer Research, 10:6411-6417 (2004).

Meucci, et al., "Ascorbic Acid Stability in Aqueous Solutions", Acta Vitaminol Enzymol, 7(3-4):147-153 (1985)—Abstract, 1 page.

Neutrogena. Http://www.cosmetoscope.com/2010/04/neutrogena-clinical-with-johnson-johnsons-cytomimic-techology/. Published Apr. 28, 2010. Accessed Sep. 11, 2010, 5 pages.

Nietz, "Molecular orientation at surfaces of solids," J. Phys. Chem., 1928, 32(2): 255-269.

No Author Listed. "Opitmization of Nano-Emulsions Production by Microfluidization." European Food Research and Technology. vol. 225, No. 5-6. Sep. 2007. Abstract. 1 page.

Oil. Dictionary of Chemistry. Editor: DWA Sharp. Copyright 1990.

Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).

Padhi et al., "Phospho-olicines as positive-electrode materials for rechargeable lithium batteries," *J. Electrochemical Soc.*, 1997, 144(4): 1188-1194.

Pakpayat, et al., "Formulation of Ascorbic Acid Microemulstions with Alkyl Polyglycosides", European Journal of Pharmaceutics and Biopharmaceutics, 72:444-452 (2009).

Paula. http://ww.cosmeticscop.com/cosmetic-ingredient-dictionary/definition/259/c12-15-alkyl-benzoate.aspx. Printed Oct. 24, 2010. 1 page.

Prescription Information for Aldara, Mar. 2007 (29 pages).

Purcell, Hal C. "Natural Jojoba Oil Versus Dryness and Free Radicals." Cosmetics and Toiletries Manufacture Worldwide. 1988. 4 pages.

Raschke, et al., "Topical Activity of Ascorbic Acid: From In Vitro Optimization to In Vivo Efficacy", Skin Pharmacology and Physiology, 17(4):200-206 (2004)—Abstract, 1 page.

Ravet et al., "Electroactivity of natural and synthetic triphylite," *J. of Power Sources*, 2001, 97-98: 503-507.

Receptacle. Merriam Webster. Http://www.merriam-webster.com/dictionary/receptacle. Accessed Jul. 12, 2011. 1 page.

Richwald, "Imiquimod", Drugs Today, 35(7):497 (1999)—Abstract, 1 page.

Rieger and Rhein. "Emulsifier Selection/HLB." Surfactants in Cosmetics. 1997 (no month given). 1 page.

Scientific Discussion for the approval of Aldara, EMEA 2005 (10 pages).

Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.

Shim, et al., "Transdermal Delivery of Mixnoxidil with Block Copolymer Nanoparticles", J. Control Release, 97(3):477-484 (2004)—Abstract, 1 page.

Shrestha et al., Forming properties of monoglycerol fatty acid esters in nonpolar oil systems, *Langmuir*, 2006, 22: 8337-8345.

Silicone. Definition. Retrieved Apr. 19, 2011 from http://www.oxforddictionaries.com/definition/silicone?view=uk. 1 page.

Skin Deep Cosmetics. PPG-40-PEG-60 Lanolin Oil http://www.cosmeticsdatabase.com/ingredient/722972/PPG-40-PEG-60_Lanolin_Oil/?ingred06=722972. 2010, 3 pages.

Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.

Sonneville-Aubrun, O. et al. "Nanoemulsions: A New Vehicle for Skincare Products." Advances in Colloid and Interface Science. 108-109.. 2004. pp. 145-149.

Sreenivasa, et al., "Preparation and Evaluation of Minoxidil Gels for Topical Application in Alopecia", Indian Journal of Pharmaceutical Sciences, 68(4):432-436 (2006), 11 pages.

Stehle et al., Uptake of minoxidil from a new foam formulation devoid of propylene glycol to hamster ear hair follicles, *J. Invest. Dermatol.*, 2005, 124(4), A101.

Sugisaka, et al., "The Physiochemical Properties of Imiquimod, The First Imidazoquinoline Immune Response Modifier", Abstract 3030, Pharmaceutical Research, vol. 14, No. 11 Supplemental (November), p. S475 (1997), 2 pages.

Surfactant. Chemistry Glossary. Http://chemistry.about.com/od/chemistryglossary/g/surfactant.htm, 2012, 1 page.

Sweetman, Sean C. Martindale: The Complete Drug Reference. 33rd Edition. London. Pharmaceutical Press. Jun. 21, 2002. pp. 1073 and 1473. 5 pages.

Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.

Tanhehco, "Potassium Channel Modulators as Anti-Inflammatory Agents", Expert Opinion on Therapeutic Patents, 11(7):1137-1145 (2001)—Abstract, 3 pages.

Tata, et al., "Penetration of Minoxidil from Ethanol Propylene Glycol Solutions: Effect of Application Volume on Occlusion", Journal of Pharmaceutical Sciences, 84(6):688-691 (1995).

Tata, et al., "Relative Influence of Ethanol and Propylene Glycol Cosolvents on Deposition of Minoxidil into the Skin", Journal of Pharmaceutical Sciences, 83(10):1508-1510 (1994).

Third Party Submission for U.S. Appl. No. 12/014,088, Feb. 4, 2009, 4 pages.

Trofatter, "imiquimod in clinical Practice", European Journal of Dermatology, 8(7 Supp.):17-19 (1998)—Abstract, 1 page.

Tsai, et al., "Effect of Minoxidil Concentration on the Deposition of Drug and Vehicle into the Skin", International Journal of Pharmaceutics, 96(1-3):111-117 (1993)—Abstract, 1 page.

Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).

Tyring, "Immune-Response Modifiers: A New Paradigm in the Treatment of Human Papillomavirus", Current Therapeutic Research, 61(9):584-596 (2000)—Abstract, 1 page.

Tzen, Jason T.C. et al. "Surface Structure and Properties of Plant Seed Oil Bodies." Department of Botany and Plant Sciences, University of California, Riverside, California 92521. Apr. 15, 1992. 9 pages.

Uner, M. et al. "Skin Moisturizing Effect and Skin Penetration of Ascorbyl Palmitate Entrapped in Solid Lipid Nanoparticles (SLN)

(56) References Cited

OTHER PUBLICATIONS and Nanostructured Lipid Carriers (NLC) Incorporated into Hydrogel." Pharmazie. 60. 2005. 5 pages.
Veron, et al., "Stability of Minoxidil Topical Formulations", Ciencia Pharmaceutica, 2(6):411-414 (1992), Abstract, 1 page.
Williams, "Scale up of an olive/water cream containing 40% diethylene glycol momoethyl ether", Dev. Ind. Pharm., 26(1):71-77 (2000).
Yamada and Chung, "Crystal Chemistry of the Olivine-Type Li(Mn$\gamma$Fe$_{1-\gamma}$)PO$_4$ and (Mn$\gamma$Fe$_{1-\gamma}$)PO$_4$ as Possible 4 V Cathode Materials for Lithium Batteries," *J. Electrochemical Soc.*, 2001, 148(8): A960-967.
"Coal tars and coal-tar pitches," *Report on Carcinogens, Twelfth Edition*, 2011, 3 pages.
Adisen et al. "Topical tetracycline in the treatment of acne vulgaris," *J Drugs Dermatol.*, 2008, 7:953-5.
Baskaran et al., "Poloxamer-188 improves capillary blood flow and tissue viability in a cutaneous burn wound," *J. Surg. Res.*, 2001, 101(1):56-61.
Bell-Syer et al. "A systematic review of oral treatments for fungal infections of the skin of the feet," *J. Dermatolog. Treat.*, 2001, 12:69-74.
Boehm et al. 1994, "Synthesis of high specific activity [.sup.3 H]-9-cis-retinoic acid and its application for identifying retinoids with unusual binding properties," *J. Med. Chem.*, 37:408-414.
Carapeti et al., "Topical diltiazem and bethanechol decrease anal sphincter pressure and heal anal fissures without side effects," *Dis Colon Rectum*, 2000, 43(10):1359-62.
Cook and Mortensen, "Nifedipine for treatment of anal fissures," *Dis Colon Rectum*, 2000, 43(3):430-1.
Dumortier et al., "A review of poloxamer 407 pharmaceutical and pharmacological characteristics," *Pharmaceutical Res.*, 2006, 23(12):2709-2728.
Ebadi et al., "Healing effect of topical nifedipine on skin wounds of diabetic rats," *DARU*, 2003, 11(1):19-22.
Effendy and Maibach. "Surfactants and Experimental Irritant Contact Dermatitis." *Contact Dermatol.*, 1995, 33:217-225.
Elias and Ghadially, "The aged epidermal permeability barrier," *Clinical Geriatric Medicine*, Feb. 2002, pp. 103-120.
Fantin et al., "Critical influence of resistance to streptogramin B-type antibiotics on activity of RP 59500 (Quinupristin-dalfopristin) in experimental endocarditis due to *Staphylococcus aureus*," *Antimicrob Agents and Chemothery*, 1999, 39:400-405.
Fluhr et al., "Glycerol accelerates recovery of barrier function in vivo," *Acta Derm. Venereol*,. 1999, 79:418-21.
Garti et al. "Sucrose Esters microemulsions," *J. Molec. Liquids*, 1999, 80:253-296.
Hammer et al. "Anti-Microbial Activity of Essential Oils and other Plant extracts," *J. Applied. Microbiology*, 1999, 86:985-990
Hwang et al. "Isolation and identification of mosquito repellents in *Artemisia vulgaris*," *J. Chem. Ecol.*, 11: 1297-1306, 1985
Knight et al., "Topical diltiazem ointment in the treatment of chronic anal fissure," *Br. J. Surg.*, 2001, 88(4):553-6.
Kucharekova et al., "Effect of a lipid-rich emollient containing ceramide 3 in experimentally induced skin barrier dysfunction," *Contact Dermatitis*, Jun. 2002, pp. 331-338.
Leive et al, "Tetracyclines of various hydrophobicities as a probe for permeability of *Escherichia coli* outer membrane," *Antimicrobial Agents and Chemotherapy*, 1984, 25:539-544.
Luepke and Kemper, "The HET-CAM Test: An Alternative to the Draize Eye Test," *FD Chem. Toxic*., 1986, 24:495-196.
Osborne and Henke, "Skin Penetration Enhancers Cited in the Technical Literature," *Pharm. Technology*, Nov. 1997, pp. 58-86
Padi. "Minocycline prevents the development of neuropathic pain, but not acute pain: possible anti-inflammatory and antioxidant mechanisms," *Eur J. Pharmacol*, 2008, 601:79-87.
Palamaras and Kyriakis, "Calcium antagonists in dermatology: a review of the evidence and research-based studies," *Derm. Online Journal*, 2005, 11(2):8.

Passi et al., Lipophilic antioxidants in human sebum and aging, *Free Radical Research*, 2002, pp. 471-477.
Perrotti et al., "Topical Nifedipine With Lidocaine Ointment vs. Active Control for Treatment of Chronic Anal Fissure," *Dis Colon Rectum*, 2002, 45(11):1468-1475.
Repa et al. "All-trans-retinol is a ligand for the retinoic acid receptors," *Proc. Natl. Acad Sci, USA*, 90: 7293-7297, 1993.
Ruledge, "Some corrections to the record on insect repellents and attractants," *J. Am. Mosquito Control Assoc*, 1988, 4(4): 414-425.
Sakai et al., "Characterization of the physical properties of the stratum corneum by a new tactile sensor," *Skin Research and Technology*, Aug. 2000, pp. 128-134.
Schaefer, "Silicone Surfactants," *Tenside, Surfactants, Deterg.*, 1990, 27(3): 154-158.
Simoni et al., "Retinoic acid and analogs as potent inducers of differentiation and apoptosis. New promising chemopreventive and chemotherapeutic agents in oncology," *Pure Appl Chem.*, 2001, 73(9):1437-1444.
Smith, "Hydroxy acids and skin again," *Soap Cosmetics Chemical Specialties*, 1993, pp. 54-59.
Solans et al. "Overview of basic aspects of microemulsions," Industrial Applications of Microemulsions, Solans et al Eds, New York, 1997, 66:1-17.
Squillante et al., "Codiffusion of propylene glycol and dimethyl isosorbide in hairless mouse skin," *European J. Pharm. Biopharm.*, 1998, 46(3):265-71.
Todd et al. "Volatile Silicone Fluids for Cosmetics," *91 Cosmetics and Toiletries*, 1976, 27-32.
Torma et al., "Biologic activities of retinoic acid and 3, 4-dehydroretinoic acid in human keratinoacytes are similar and correlate with receptor affinities and transactivation properties," *J. Invest. Dermatology*, 1994, 102: 49-54.
USP23/NF 18 The United States Pharmacopeia: The National Formulary, US Pharmacopoeia, 1995, p. 10-14.
Van Slyke, "On the measurement of buffer values and on the relationship of buffer value to the dissociation constant of the buffer and the concentration and reaction of the buffer solution," *J. Biol. Chem.*, 1922, 52:525-570.
Van Cutsem et al., "The antiinflammatory efects of ketoconazole," *J. Am. Acad. Dermatol*.,1991, 25(2 pt 1):257-261.
Wang and Chen, "Preparation and surface active properties of biodegradable dextrin derivative surfactants," *Colloids and Surfaces A: Physicochemical and Engineering Aspects*, 2006, 281(1-3):190-193.
Weindl et al., "Hyaluronic acid in the treatment and prevention of skin diseases: molecular biological, pharmaceutical and clinical aspects," *Skin Pharmacology and Physiology*, 2004, 17: 207-213.
Xynos et al., "Effect of nifedipine on rectoanal motility," *Dis Colon Rectum*, 1996, 39(2):212-216.
Yamada et al., "Candesartan, an angiotensin II receptor antagonist, suppresses pancreatic inflammation and fibrosis in rats," *J. Pharmacol. Exp. Ther.*, 2003, 307(1)17-23.
Paragraph E.3.1 of regulation (EC) No 2003 (See Directive 67/548/EEC OJ 196, 16.8, 1967, p. 1.
Tzen et al., Lipids, proteins and structure of seed oil bodies from diverse species; *Plant Physiol.*, 1993, 101:267-276.
Brown et al. "Structural dependence of flavonoid interactions with Cu2+ inos: implications for their antioxidant properties," *Biochem. J.*, 1998, 330:1173-1178.
Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol.*, 2003, 15:233-40.
"Mineral oil USP," Chemical Abstracts Service Registry No. 8012-95-1, 2011, 7 pages.
"Tea tree oil," Chemical Abstract No. 68647-73-4, 2012, 2 pages.
Lin et al., "Ferulic acid stabilizes a solution of vitamins c and e and doubles its protoprotection of skin," *J Invest Dermatol*, 2005, 125:826-32.
Official action from European Application No. 09707299.5, dated Apr. 7, 2011, 4 pages.
Official action from European Application No. 09707299.5, dated Jan. 19, 2012, 5 pages.

(56) References Cited

OTHER PUBLICATIONS

International Preliminary Examination Report from PCT/IB2009/005032, dated Aug. 10, 2010 and International Search Report dated Sep. 25, 2009, 13 pages.
"HLB Systems", http://pharmcal.tripod.com/ch17.htm, Accessed Sep. 17, 2010, pp. 1-3.
Alcohol SDA 40B.http://www.pharmco-prod.com/pages/MSDS/SDA.sub.--40B.sub.--200.pdf Accessed Dec. 9, 2008, 2 pages.
Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds,"Antimicrobial Agents and Chemotherapy, vol. 35, No. 9, pp. 1799-1803, 1991.
Arisan, http://www.arisankimya.com/kozmetik.htm Accessed Dec. 10, 2008, 8 pages.
Barry, B.W. et al, Comparative bio-availability and activity of proprietary topical corticosteroid preparations: vasoconstrictor assays on thirty-one ointments, British Journal of Dermatology, 93, 563-571, 1975.
Benet, et al., App-lication of NMR for the Determination of HLB Values of Nonionic Surfactants, Journal of the American Oil Chemists Society, vol. 49, 1972, 499-500.
Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.
Carbowax 1000MSDS; http://www.sciencelab.com/xMSDS-Polyethylene.sub.--glycol.sub.--1000-9926-622. Accessed Dec. 13, 2008, 6 pages.
Cheshire, et al., Disorders of Sweating, www.medscape.com, Semin Neurol 23(4):399-406, 2003.
Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.
D.W.A. Sharp Dictionary of Chemistry, Penguin Books, 1983, 3 pages.
Dalby, "Determination of Drug Solubility in Aerosol Propellants," Pharmaceutical Research, vol. 8, No. 9, 1991, pp. 1206-1209.
Denatonium Benzoate http://www.newdruginfo.com/pharmaceopeia/usp28/v28230/usp28nf23s0.sub.--m-22790.htm Accessed Dec. 9, 2008, 2 pages.
Disorder. (2007). In the American Heritage Dictionary of the English Language. Retrieved from http://www.credoreference.com/entry/hmdictenglang/disorder. 1 page.
Edirisinghe, et al., "Effect of fatty acids on endothelium-dependent relaxation in the rabbit aorta", Clin Sci (Lond). Aug. 2006; 111(2): 145-51.
Emulsifiers with HLB values. http://www.theherbarie.com/files/resources-center/formulating/Emulsifiers-.sub.--HLB.sub.--Values.pdf accessed Aug. 5, 2009 (3 pages).
Encyclopedia of Pharmaceutical Technology, Second Edition, vol. 3, Copyright 2002, 4 pages.
English machine translation of JP-08165218 (1996), 9 pages.
English translation of abstract for Japanese Patent Publication No. 4892282 (1992), 1 page.
Ethanol, Accessed http://www.sigmaaldrich.com/catalog/ProductDetail.do?N4=E7023SIAL&N5=SEAR-CH.sub.--CONCAT.sub.--PNOBRAND.sub.--KEY&F=SPEC Dec. 9, 2008, 2 pages.
European Official Action, European Patent Application No. 06831721.3, Feb. 3, 2009, 9 pages.
Final Office Action for U.S. Appl. No. 11/430,437, Tamarkin et al., Dec. 16, 2008, 18 pages.
Flick, Cosmetic and Toiletry Formulations, vol. 5, 2nd Edition, Copyright 1996, 63 pages.
Fonatana, Anthony J., "Water Activity: Why It is Important for Food Safety," International Conference on Food Safety, Nov. 16-18, 1998, pp. 177-185.
Galligan, John et al., "Adhesive Polyurethane Liners for Anterior Restorations," J. Dent. Res., Jul.-Aug. 1968, pp. 629-632.
Gill, A.M, et al., "Adverse Drug Reactions in a Paediatric Intensive Care Unit," Acta Paediatr 84:438-441, 1995.
Glaser, et al., Hyperhidrosis: A Comprehensive and Practical Approach to Patient Management, Expert Rev. Dermatol. 1(6), 773-775 (2006).
Gschnait, F., et al., "Topical Indomethacin Protects from UVB and UVA Irriadiation," Arch. Dermatol. Res. 276:131-132, 1984.
Hakan, et al., "The protective effect of fish oil enema in acetic acid and ethanol induced colitis," The Turkish Journal of Gasroenterology, 2000, vol. 11, No. 2, pp. 155-161.
Hall, Karla, "Diaper Area Hemangiomas: A Unique Set of Concerns," http://members.tripod.com/.about.Michelle.sub.--G/diaper.html, Dec. 1, 2008, 8 pages.
Hashim, et al. "Tinea versicolor and visceral leishmaniasis," Int J Dermatol., Apr. 1994; 33(4), pp. 258-259 (abstract only).
Heart Failure, The Merck Manual, 2008 <<http://www.merck.com/mmhe/sec03/ch025/ch025a.html>> 12 pages.
Hepburn, NC., "Cutaneous leishmaniasis," Clin Exp Dermatol, Jul. 2000; 25(5), pp. 363-370 (abstract only).
Hill, Randall M. (Ed.) Silicone Surfactants, Table of Contents and Chapter 7, "Silicone Surfactants: Applicants in the Personal Care Industry," by David T. Floyd, 1999 (30 pages).
http://ibabydoc.com/online/diseaseeczema.asp., Atopic Dermatitis, Copyright 2000, 6 pages.
http://web.archive.org/web/20000106225413/http://pharmacy.wilkes.edu/kibbeweb/lab7.html, Characteristics of Surfactants and Emulsions, Jan. 29, 2010, 5 pages.
http://www.agworkshop.com/p3.asp, AG&Co. Essential oil workshop, 1 page, (2011).
Hydroxyethylcelllulose. htt;://terpconnect.umd.edu/.about.choi/MSDS/Sigma-Aldrich/HYDROXYETHYL%20-CELLULOSE, 5 pages, (2011).
Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.
International Search Report and Written Opinion for International Application No. PCT/IB10/02241 mailed Feb. 10, 2011. 9 pages.
International Search Report and Written Opinion, International Application No. PCT/IB2006/003628, Foamix Ltd., Dec. 7, 2007, 15 pages.
International Search Report and Written Opinion, International Application No. PCT/US2007/004459, Foamix Ltd., Dec. 9, 2008, 15 pages.
International Search Report and Written Opinion, International Patent Application No. PCT/IB2006/004026, Foamix, Ltd., Jun. 20, 17 pages.
International Search Report for International Application No. PCT/IB2006/003974, Feb. 25, 2008 (3 pages).
International Search Report from PCT/IB2006/003519, Mailed Dec. 3, 2007. 1 page.
International Search Report, International Patent Application No. PCT/IB2007/003463, Foamix, Ltd., Jul. 18, 2008, 3 pages.
International Search Report, International Patent Application No. PCT/IB2007/003759, Foamix Ltd., Jul. 8, 2008 (3 pages).
Kalkan, et al., The Measurement of Sweat Intensity Using a New Technique, Tr. J. of Medical Sciences 28, 515-517 (1998).
Kanamoto, et al., "Pharmacokinetics of two rectal dosage forms of ketoprofen in patients after anal surgery," J Pharmacobiodyn., Mar. 1988; 11(3):141-5.
Karasu, T.B. et al., "Treatment of Patients with Major Depressive Disorder, Second Edition," pp. 1-78, 2000.
Kathon.TM. CG (product information sheet by Rohm and Haas, Jun. 2006), 9 pages.
Kinnunen, Contact Dermatitis Sep. 1989; 21(3): 154-8.
Kleber, M.D., H.D. et al., "Treatment of Patients with Substance Use Disorders, Second Edition," pp. 1-276, 2006.
Koerber, S., "Humectants and Water Activity," Water Activity News, 2000, ISSN No. 1083-3943, 8 pages.
Kreuter, J. "Nanoparticles and microparticles for drug and vaccine delivery," J. Anat. (1996) 189, pp. 503-505.

(56) References Cited

OTHER PUBLICATIONS

Kumar, J. et ak., "Application of Broad Spectrum Antiseptic Povidone Iodine as Powerful Action: A Review," Journal of Pharmaceutical Science and Technology vol. 1(2), 2009, 48-58.
Leung, et al., "Bioadhesive Drug Delivery in Water-Soluble Polymers," American Chemical Society, Chapter 23, 1991, pp. 350-366.
Licking Vaginal Dryness without a Prescription. Accessed http://www.estronaut.com/a/vag.sub.--dryness.htm on Dec. 14, 2008, 3 pages.
Martindale, The extra pharmacopoeia [28th] edition, Eds.: Reynolds, J.E.F. and Prasad, A.B., The Pharmaceutical Press, London, pp. 862-864, 1982.
Material Safety Data Sheet, Progesterone, Apr. 26, 2006, 5 pages.
Material Safety Data Sheet, Science Lab.com, Polyethylene Glycol 1000, MSDS, Nov. 6, 2008, 6 pages.
Merriam Webster Online Dictionary [online], "Derivative", retrieved from http://www.merriam-webster.com/cgi-bin/dictionary?book=dictionary&va=derivative on Jul. 5, 2008; 1 page.
Merriam-Webster Online Dictionaary, 2008, "Mousse," Merriam-Webster Online, Dec. 8, 2008 http://www.merriam-webster.com/dictionary/mousse, 1 page.
Metronidazole. www.usp.org/pdf/EN/veterinary/metronidazole.pdf. accessed Sep. 10, 2009, 4 pages.
MMP Inc. International Development and Manufacturing, "Formulating specialities," http://mmpinc.com, 3 pages, (2011).
Molan, Peter Clark, "World Wide Wounds," Dec. 2001, 13 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
Office Action for U.S. Appl. No. 11/430,437, Tamarkin et al., May 9, 2008, 27 pages.
Office Action received from the U.S. Patent Office, U.S. Appl. No. 11/430,599, Jul. 28, 2008 (59 pages).
OM Cinnamate. http://www.makingcosmetics.com/sunscreens/OM-Cinnamate-p102.html accessed Sep. 26, 2009, 1 page.
Pendergrass, Gynecol Obstet. Invest. 1996:42(3):178-82.
Prevent. (2007). In the American Heritage Dictionary of the English Language. Retrieved from http://www.credoreference.com/entry/hmdictenglang/prevent, 1 page.
Progesterone MSDS. http://www.usp.org.pdf.EN/referenceStandards/msds/1568007.pdf on Dec. 14, 2002, 5 pages.
Psoriasis, http://www.quickcare.org/skin/causes-of0psoriasis.html. Accessed Sep. 9, 2010. 3 pages.
Raymond, Iodine as an Aerial Disinfectant, Journal of Hygiene, vol. 44, No. 5 (May 1946), pp. 359-361.
Rosacea, http://clinuvel.com/skin-conditions/common-skin-conditions/rosacea#h0-6-prevention. Accessed Sep. 9, 2010. 5 pages.
Savin, et al., "Tinea versicolor treated with terbinafine 1% solution," Int J. Dermatol, Nov. 1999; 38(11), pp. 863-865.
Schmidt A., "Malassezia furfur: a fungus belonging to the physiological skin flora and its relevance in skin disorders," Curtis., Jan. 1997; 59(1), pp. 21-24 (abstract).
Schutze, M.D., Harry "Iodine and Sodium Hypochlorite as Wound Disinfectants," The British Medical Journal, pp. 921-922, 1915.
Scott as Published in Pharmaceutical Dosage Forms; Disperse Systems, vol. 3, Copyright 1998, 120 pages.
Seborrheic Dermatitis, http://www.cumc.columbia.edu/student/health/pdf/R-S/Seborrhea%20Dermatitis.pdf. Access Sep. 9, 2010—2 pages.
Shear, et al., "Pharmacoeconomic analysis of topical treatments for tinea infections," Pharmacoeconomics. Mar. 1995; 7(3); pp. 251-267 (abstract only).
Sigma Aldrich, "HLB-Numbers In Lithography Nanopatterning," http://www.sigmaaldrich.com/materials-science/micro-and-nanoelectronics/l-ithography-nanopatterning/hlb-numbers.html, accessed: Feb. 2, 2009, pp. 1-3.
Sigma-Aldrich, Material Safety Data Sheet, Hydroxyethyl Cellulose, Mar. 3, 2004, 5 pages.
Simovic, S. et al., "The influence of Processing Variables on Performance of O/W Emulsion Gels Based on Polymeric Emulsifier (Pemulen ® TR-2NF)," International Journal of Cosmetic Science, vol. 2(2): abstract only. 1999. 1 page.
Skin Biology, CP Serum—Copper-Peptide Serum for Skin Regeneration and Reducing Wrinkles, Skin Biology, http://web.archive.org/web/20030810230608/http://www.skinbio.com/cpserum.-html, Dec. 1, 2008, 21 pages.
Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment ofdandruff/seborrhoeic dermatitis," Dermatolog Treat. Jun. 2002;13(2):51-60 (abstract only).
Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.
Tarumoto, et al., Studies on toxicity of hydrocortisone 17-butyrate 21-propionate-1. Accute toxicity of hydrocortisone 17-butyrate 21-propionate and its analogues in mice, rats and dogs (author's trans), J Toxicol Sci., Jul. 1981; 6 Suppl: 1-16.
Torres-Rodriguez, JM., "New topical antifungal drugs," Arch Med Res. 1993 Winter; 24(4), pp. 371-375 (abstract).
Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.
Wermuth, C.G. "Similarity in drugs: reflections on analogue design," Drug Discovery Today, vol. 11, Nos. 7/8, Apr. 2006, pp. 348-354.
Wormser et al., Protective effect of povidone-iodine ointment against skin lesions induced by sulphur and nitrogen mustards and by nonmustard vesicants, Arch. Toxicol., 1997, 71, 165-170.
Wormser, Early topical treatment with providone-iodine ointment reduces, and sometimes prevents, skin damage following heat stimulus, Letter to the Editor, Burns 24, pp. 383, 1998.
"Arquad HTL8-MS,"*AkzoNobel Functional Applications*, retrieved on Mar. 18, 2013, Retrieved from the Internet: <URL: http://sc.akzonobel.com/en/fa/Pages/product-detail.aspx?prodID=8764>, 1 page.
"Can tuberous sclerosis be prevented?," *Sharecare*, 2002, retrieved on Aug. 29, 2013, <URL:.http://www.sharecare.com/health/autosomal-dominant-genetic-disorders/can-tuberous-sclerosis-be-prevented;jsessionid=850579B60520A907DE75930E061E60E6>, 2 pages.
"Crohn's Disease," *Merch Manual Home Edition*, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.
"Dacarbazine," *Chemical Book*, 2010, retrieved on Oct. 18, 2013, <URL: http://www.chemicalbook.com/ChemicalProductProperty_EN_CB7710656.htm>, 2 pages.
"Drug Index (Professional)—Dacarbazine," *BC Cancer Agency*, Jun. 2004, retrieved on Oct. 18, 2013, <URL:http://www.bccancer.bc.ca/HPI/DrugDatabase/DrugIndexPro/Dacarbazine.htm>, 6 pages.
"Fully refined paraffin waxes (FRP Wax)," *Industrial Raw Materials LLC*, Feb. 21, 2008, retrieved on Aug. 22, 2013, <http://irmwax.com/Wax/Paraffin/fully_refined.asp> 1 page.
"Gas Gangrene," Merch Manual Home Edition, 2008, retrieved on Jan. 16, 2013, <http://www.merckmanuals.com/home/infections/bacterial_infections/gas_gangrene.html?qt=gas gangrene&alt=sh>1 page.
"Human Immunodeficiency Virus Infection," Merch Manual Home Edition, 2008, retrieved on Jan. 16, 2013, <http://www.merckmanuals.com/home/infections/human_immunodeficiency_virus_hiv_infection/humanimmunodeficiency_virus_infection.html?qt=human immunodeficiency virus infection&alt=sh >, 11 pages.
"Minocycline (DB01017)," *DrugBank*, Feb 8, 2013, retrieved on Aug. 15, 2013, <http://www.drugbank.ca/drugs/DB01017>, 10 pages.
"New Nanomaterials to deliver anticancer drugs to cells developed," *Science Daily*, Jun. 2007, retrieved on Oct. 14, 2013, <URL: http://www.sciencedaily.com/releases/2007/06/070607112931.htm>, 3 pages.

(56) References Cited

OTHER PUBLICATIONS

"Product Data Sheet for Meclocycline," *bioaustralis fine chemicals*, Jun. 28, 2013, 1 page.
"View of NCT01171326 on Dec. 7, 2010," *ClinicalTrials.gov archive*, Dec. 7, 2010, retrieved on Sep. 9, 2013, <http://clinicaltrials.gov/archive/NCT01171326/2010_12_07>, 4 pages.
"View of NCT01362010 on Jun. 9, 2011," Jun. 9, 2011, retrieved on Sep. 9, 2013, <http://clinicaltrials.gov/archive/NCT01362010/2011_06_09>, 3 pages.
"What is TSC?," *Tuberous Sclerosis Alliance*, Jan. 1, 2005, retrieved on Feb. 6, 2014, <URL: http://www.tsalliance.org.pages.aspx?content=2>, 3 pages.
Abrams et al., "Ciclopirox gel treatment of scalp seborrheic dermatitis," *Hydroxy-Piridones as Antifungal Agents with Special Emphasis on Onychomycosis*, 1999, Chapter 8, 45-50.
Blaney and Cook, "Topical use of tetracycline in the treatment of acne," *Arch Dermatol*, Jul. 1976, 112:971-973.
Cetearyl Alcohol, Natural Wellbeing, Copyrigh 2001-2012, retrieved on Apr. 10, 2014, http://www.naturalwellbeing.com/learning-center/Cetearyl_Alcohol, 3 pages.
Cunha, "Minocycline versus Doxycycline in the treatment of Lyme Neuroborreliosis," *Clin Infect. Diseases*, 2000, 30: 237-238.
Durian et al., "Scaling behavior in shaving cream," *The Americal Physical Society*, Dec. 1991, 44(12):R7902-7905.
Google search strategy for minocycline solubility, retrieved on Aug. 15, 2013, <http://www.googl.com/search?rls=com.microsoft%3Aen-us%3AIE-SearchBox&q-melocycline+solubility>, 1 page.
Harry, "Skin Penetration," *The British Journal of Dermatology and Syphillis*, 1941, 53:65-82.
Koerber, S., "Humectants and Water Activity," Water Activity News, 2000, ISSN No. 1083-3943.
Lee et al., "Historical review of melanoma treatment and outcomes," *Clinics in Dermatology*, 2013, 31: 141-147.
Livingstone and Hubel, "Segregation of form, color, movement, and depth: Anatomy, physiology, and perception," *Science*, May 1988, 240:740-749.
Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.
Neves et al., "Rheological Properties of Vaginal Hydrophilic Polymer Gels," *Current Drug Delivery*, 2009, 6:83-92.
Prud'homme et al., *Foams: theory, measurements and applications*, Marcel Dekker, Inc., 1996, 327-328.
Purdy et al., "Transfusion-transmitted malaria: unpreventable by current donor exclusion guidelines?" *Transfusion*, Mar. 2004, 44:464.
*Reregistration Eligibility Decision for Pyrethrins*, EPA, Jun. 7, 2006, 108 pages.
Sehgal, " Ciclopirox: a new topical pyrodonium antimycotic agent: A double-blind study in superficial dermatomycoses," British Journal of Dermatology, 1976, 95:83-88.
Schmolka, "A review of block polymer surfactants," *Journal of the American Oil Chemists Society*, Mar. 1977, 54: 110-116.
Sciarra, "Aerosol Technology," Kirk-Othmer Encyclopedia of Chemical Technology, Jul. 2012, 20 pages.
Schott, "Rheology," *Remington's Pharmaceutical Sciences*, 17th Edition, 1985, 330-345.
Scully et al., "Cancers of the oral mucosa treatment and management," *Medscape Drugs, Diseases and Procedures*, Apr. 20, 2012, retrieved on Oct. 12, 2013, <http://emedicine.medscape.com/article/1075729-treatment>, 10 pages.
Softemul-165: Product Data Sheet, Mohini Organics PVT LTD, retrieved Apr. 10, 2014, http://www.mohiniorganics.com/Softemul165.html#, 1 page.
Tavss et al., "Anionic detergent-induced skin irritation and anionic detergent-induced pH rise of bovine serum albumin," *J. Soc. Cosmet. Chem.*, Jul./Aug. 1988, 39:267-272.
Tirmula et al., "Abstract: D28.00011: Enhanced order in thinfilms of Pluronic (A-B-A) and Brij (A-B) Block copolymers blended with poly (acrylic acid)," Session D28: Block Copolymer Thin Films, Mar. 13, 2006, 1 page, Abstract.
Tsai, et al., "Drug and Vehicle Deposition from Topical Applications: Use of in Vitro Mass Balance Technique with Minosidil Solutions", J. Pharm. Sci., 81(8):736-743 (1992)—Abstract, 1 page.

\* cited by examiner

SUBSTANTIALLY NON-AQUEOUS FOAMABLE PETROLATUM BASED PHARMACEUTICAL AND COSMETIC COMPOSITIONS AND THEIR USES

CROSS REFERENCE TO RELATED APPLICATIONS

This application is a continuation of and claims the benefit of priority under 35 U.S.C §120 to U.S. patent application Ser. No. 12/025,547, filed Feb. 4, 2008, entitled "Substantially Non-Aqueous Foamable Petrolatum Based Pharmaceutical And Cosmetic Compositions And Their Uses," which claims the benefit of priority under 35 U.S.C. §119(e) to U.S. Provisional Application No. 60/899,176 filed Feb. 2, 2007, entitled "Non-Alcoholic Foamable Petrolatum Based Pharmaceutical And Cosmetic Compositions And Their Uses," and to U.S. Provisional Application No. 60/915,859 filed May 3, 2007, entitled "Non-Aqueous Foamable Petrolatum And Miscible Solvent Based Pharmaceutical And Cosmetic Compositions And Their Uses," and which is a continuation-in-part of co-pending U.S. patent application Ser. No. 11/940,290, filed on Nov. 14, 2007, which claims the benefit of priority under 35 U.S.C. §119(e) to U.S. Provisional Patent Application No. 60/858,747, filed on Nov. 14, 2006, both entitled "Stable Non-Alcoholic Foamable Pharmaceutical Emulsion Compositions With An Unctuous Emollient And Their Uses," all of which are herein incorporated in their entirety by reference.

BACKGROUND

Petrolatum is used in dermatology to lubricate, protect, heal and medicate the skin and as a vehicle for topical drugs. Petrolatum is not suited to formation of foams. It is an unctuous solid and does not flow and is not shakable per se. Addition of large amounts of propellant to try and improve its flow is not desirable in general since the resultant material can have a cooling effect on application to the skin, mucosal cavity or body cavity. Addition of hydrophobic solvents can be useful to improve healing qualities of the formulation and to soften the petrolatum, but it can also significantly and substantially complicate or impede foam formation.

Foams are complex multi-ingredient systems which do not form under all circumstances. High quality foams are not at all easy to produce especially in a waterless environment. Yet, foams are easy to apply, use and spread and are a preferred mode of topical application. Changes in foam composition, such as, by the addition of active ingredients, may destabilize the foam. There is, therefore, a need for a foam composition, which provides desirable properties to the skin or body cavity and can be stable whilst accommodating a variety of active ingredients.

Petrolatum in its various forms has a number of useful attributes for use in topical foamable pharmaceutical and cosmetic compositions. They are inherently stable and inert, which are clearly desirable characteristics. They are also able to moisturize and soften the skin and in appropriate amounts can act as a protective or barrier layer and can form a barrier to water, which can, for example, solubilize or cause destabilization of some active ingredients. By careful design and appropriate formulation of petrolatum compositions they can act to improve drug delivery to the skin; provide a protective environment for the drug and yet remain resistant to being washed off unintentionally. On the other hand petrolatums are by their nature greasy materials and can present a difficult challenge to formulate them into a topical non-aqueous or substantially so foamable composition that can deliver substantially uniform and stable foam that ameliorates and or overcomes the look and feel of a greasy material. It is further a problem to incorporate into such a vehicle pharmaceutically effective amounts of one or more active pharmaceutical ingredients such that they are uniformly present throughout the formulation and are effectively delivered especially without the use of an alcohol in the formulation.

Aliphatic alcohols in foam compositions promote fast drying and thereby attempt to address the sticky feeling left by many topical formulations after application; however, alcohols, and in particular short chain alcohols like methyl, ethyl and isopropyl alcohols are defatting agents and may cause skin to become dry and cracked. Also, the presence of such alcohols generates alcoholic foam that is thermal sensitive and quick breaking, e.g., it collapses readily upon contact with a surface upon exposure to body temperature environment. Although certain compositions based on petrolatum are known they are, for example, designed to form an occlusive layer in the presence of active pharmaceutical agents that are not soluble in the water or oil phase. Although some lipophillic compositions containing petrolatum and silicone oil are known, the silicone oil is an essential and main component and it is used to try and overcome the greasy feeling of petrolatum. Silicones can have substantial disadvantages in foamable compositions and foams especially in significant levels.

In the light of the unctuous, greasy, tacky, and heavy nature of petrolatum, there are problems in producing stable emulsion foams of good quality and texture from high levels of petrolatum and there is a real technical challenge of achieving inter alia a good bubble structure, texture, spreadability and look and feel. The presence of water is important in contributing to feel of the foam. Developing foams with such characteristics that are substantially free of water is a technical and inventive challenge. This challenge is increased where the formulations are to be substantially free of silicone oil and substantially free of lower alcohols.

Alcohol is known to impair the integrity of the skin barrier, dry the skin and cause skin irritation. The incidence skin irritation (burning, itching and stinging) can be very high. Thus, while alcohol is useful in solubilizing an active agent and enabling effective dermal penetration of an active agent, the development of a safe foam vehicle, which will overcome the evident skin drying and irritation caused by alcohol, is warranted, especially where sensitive skin, mucosa, or body cavity membranes are being targeted. Furthermore, foam compositions that possess a lesser degree of thermal sensitivity, thus being more useful for the treatment of large skin areas are desired.

Foamable compositions that produce foams, which are soft are desirable especially with improved stability.

It is particularly advantageous to have a foamable vehicle that is suitable for use as a base for delivery of not merely one type of active pharmaceutical ingredient (API) but is adaptable for use with one or more API's from a wide range of different types of API's with relatively minimal or minor adjustment to the vehicle. For example, by altering the amount of a component or by the addition of a buffer that provides a pH at which the API is stable as would be appreciated by a person skilled in the art.

SUMMARY

This application relates to petrolatum-based foamable vehicles, pharmaceutical compositions and resultant foams. In one embodiment, the petrolatum-based foamable vehicles, pharmaceutical compositions and resultant foams are non-aqueous. In one embodiment, petrolatum-based foamable vehicles, pharmaceutical compositions and resultant foams have low water content. The application further relates to such compositions and to such resultant foams that are non-silicone and or are non-alcoholic or substantially so.

A prime concept covered herein is that petrolatum as a hydrophobic carrier is a main ingredient and is at least about 50% of the foamable carrier alone or in combination with a solvent substantially miscible therein for example a hydrophobic oil. In a preferred aspect the percentage of petrolatum is more than about 60%. In one aspect the foamable carrier is non-aqueous and the petrolatum is at least about 25% and is in combination with a solvent substantially miscible therein such that together they are at least about 80% and the carrier is substantially free of silicone oil. By substantially free it is meant that the silicone oil content in the composition is less than about 1%. In another aspect the foamable carrier is substantially non-aqueous or has low water content and the petrolatum is more than about 50% or more than about 55% and preferably more than about 60%. By substantially non-aqueous or low water content it is meant that the amount of water if present in the composition is small and is less than about 26%, preferably less than about 16% and more preferably less than about 13%. Although the proportion of water is relatively very small by selective use of appropriate and compatible surfactants it can be possible to produce both water in oil and also oil in water petrolatum emulsion compositions. Whilst these carriers are intended to be without lower or short chain alcohols, where an API is provided as an alcoholic extract, such small amount of alcohol is permitted in the compositions. In certain embodiments, such lower alcohol content is reduced or essentially eliminated by evaporation upon warming.

In an embodiment the petrolatum based carriers comprise one or more active pharmaceutical ingredients (API's). The formulations are designed to carry homogeneously large ranges of API's from microgram levels to up to about 33% of the composition. Some API's are stable in one kind of environment whilst others require a different environment. For example, many steroids are known to undergo rearrangement at high pH, and are more stable in acidic formulations whilst vitamin D and its derivatives fare better in a basic medium. So adding an acidic modulating agent such as an acidic buffer, or fatty acid helps prevent steroid degradation whilst the addition of a basic modulating agent, such as a basic buffer or triethanolamine is useful to maintain acceptable stability for vitamin D and derivatives. Other substances break down or react more rapidly in the presence of water and therefore are sustained better in a non-aqueous medium. The formulations described herein offer waterless and substantially waterless or low water content variations and an appropriate carrier may be selected for an API depending on its sensitivity and reactivity in the presence and absence of relatively small amounts of water. Whilst the carrier compositions described herein may be useful carriers for API's some are not compatible in the same formulations and may react or breakdown. The formulations described are suitable for use in dual or multi chamber foam delivery devices, where each chamber delivers an API which if stored with the API's in the other chamber(s) would have broken down. In one embodiment the carrier in the first chamber is substantially waterless and the carrier in the second chamber is waterless. In another embodiment the carrier is basically the same in each chamber although some minor variations such as to pH or artificial pH or in the presence of one or more preservatives, stabilizers, antioxidants, and the like may be made to reflect the specific requirements of the API.

To generate the good quality foams described herein the formulations contain a foam agent. In one or more embodiments the foam agent is selected from the group consisting of a surfactant, a surfactant combination, a foam adjuvant and combinations thereof. In one or more further embodiments the quality may be improved by addition of a polymeric agent. The polymeric agent may preferably have some surfactant-like properties or help to ameliorate the tacky greasy properties of petrolatum.

In one embodiment, the foamable composition is a non-aqueous, non-alcoholic foamable composition that includes a foamable carrier and at least one liquefied or compressed gas propellant. The foamable carrier includes (1) a petrolatum or mixtures thereof at a concentration of about 25% to about 95% by weight; (2) a solvent substantially miscible in the petrolatum at a concentration of about 0% to about 70% by weight; and (3) at least one foam agent selected from the group consisting of a surfactant, a surfactant system, a foam adjuvant and combinations thereof; at a concentration of about 0.1% to about 20% by weight. In the absence of the solvent, the petrolatum is present in the foamable carrier at a concentration of at least about 50% by weight. In the presence of the solvent, (i) the petrolatum is present in the foamable carrier at a concentration of at least about 25% by weight and the solvent and petrolatum are together present in the foamable carrier at a concentration of least about 55% by weight; or (ii) the amount of petrolatum is about the same as or in excess of the solvent and, together, the solvent and petrolatum are present in the foamable carrier at a concentration of at least about 80%. The ratio of the foamable carrier to the propellant is 100:10 to 100:35. The composition is substantially free of silicone. The composition is stored in a pressurized container or aerosol container and upon release expands to form a breakable foam.

In one embodiment, the foamable composition is a non-aqueous, non-alcoholic foamable composition that includes a foamable carrier and at least one liquefied or compressed gas propellant. The foamable carrier includes (1) a petrolatum or mixtures thereof at a concentration of about 50% to about 95% by weight; (2) a solvent substantially miscible in the petrolatum at a concentration of about 0% to about 45% by weight; (3) at least one foam agent selected from the group consisting of a surfactant, a surfactant system; a foam adjuvant and combinations thereof at a concentration of about 0.1% to about 20% by weight; and (4) an effective amount of an active pharmaceutical agent. The ratio of the foamable carrier to the propellant ranges from about 100:10 to about 100:35. The composition is substantially free of silicone. Moreover, the composition is resistant to centrifugation at 1000 rpm for about 10 minutes; is flowable or flowable to a degree and or is shakable or substantially so when stored in a pressurized container or an aerosol container and upon release expands to form a breakable foam having no substantial or sustained cooling affect and having a foam hardness in the range of about 5 g to about 100 g.

In one embodiment, the foamable composition is a low water content, non-alcoholic foamable composition that includes a foamable carrier and at least one liquefied or compressed gas propellant. The foamable carrier includes (1) a petrolatum or mixtures thereof at a concentration of about 25% to about 95% by weight; (2) a solvent substantially miscible in the petrolatum at a concentration of 0% to about 70% by weight; (3) at least one foam agent selected from the group consisting of a surfactant, a surfactant system, a foam adjuvant and combinations thereof; at a concentration of about 0.1% to about 20% by weight; and (4) water at a concentration of up to about 26% by weight. In the absence of the solvent, the petrolatum is present in the foamable carrier at a concentration of at least about 50% by weight. In the presence of the solvent: (i) the petrolatum is present in the foamable carrier at a concentration of at least about 25% by weight and the solvent and petrolatum are together present in the foamable carrier at a concentration of least about 55% by weight; or (ii) the amount of petrolatum is about the same as or in excess of the solvent and, together, the solvent and petrolatum are present in the foamable carrier at a concentration of at least about 80%. The ratio of the foamable carrier to the propellant ranges from about 100:10 to about 100:35. The composition is substantially free of silicone. The composition is stored in a pressurized container or aerosol container and upon release expands to form a breakable foam. In one embodiment, the foamable composition is a low water content, non-alcoholic foamable composition that includes a foamable carrier and at least one liquefied or compressed gas propellant. The foamable carrier includes (1) a petrolatum or mixtures thereof at a concentration of about 50% to about 95% by weight; (2) a solvent substantially miscible in the petrolatum at a concentration of about 0% to about 45% by weight; (3) at least one foam agent selected from the group consisting of a surfactant, a surfactant system; a foam adjuvant and combinations thereof at a concentration of about 0.1% to about 20% by weight; and (4) an effective amount of an active pharmaceutical agent. The solvent is water and is present in the carrier at a concentration of about 0.1% to about 26% by weight. The ratio of the foamable carrier to the propellant ranges from about 100:10 to about 100:35. The composition is substantially free of silicone. The composition is resistant to centrifugation at 1000 rpm for about 10 minutes and is flowable or flowable to a degree and or is shakable or substantially so when stored in a pressurized container or aerosol container and upon release expands to form a breakable foam having no substantial or sustained cooling affect and having a foam hardness in the range of about 5 g to about 100 g In one or more embodiments there is provided a substantially non-aqueous, non-alcoholic, non-silicone foamable carrier composition comprising:
(1) a petrolatum or mixtures thereof at a concentration of about 25% to about 95% by weight prior to the addition of propellant;
(2) a solvent substantially miscible therein other than the propellant, at a concentration of about 0% to about 70% by weight prior to the addition of propellant;
(3) at least one foam agent selected from the group consisting of a surfactant, surfactant system, a foam adjuvant and combinations thereof at a concentration of about 0.1% to about 20% by weight prior to the addition of propellant;
(4) at least one liquefied or compressed gas propellant at a concentration of about 10% to about 35% by weight of the total composition;
wherein in the absence of the said substantially miscible solvent the amount of petrolatum is at least about 50%; and
wherein in the presence of the substantially miscible solvent the amount of petrolatum is either (i) at least about 25% prior to the addition of propellant and the amount of the substantially miscible solvent in combination with petrolatum is at least about 55% prior to the addition of propellant or (ii) the amount of petrolatum is about the same as or in excess of the substantially miscible solvent and their combined amount is at least about 80% prior to the addition of propellant and wherein the composition is stored in an aerosol container and upon release expands to form a breakable foam.

In one or more other embodiments the amount of petrolatum is in excess of about 50% and there is present an amount of solvent substantially miscible therein between about 0.1% to about 45%. Preferably it is in excess of about 55% and the range is about 0.1% to about 40% and more preferably in excess of about 60% and the range is about 0.1% to about 35%.

In one or more embodiments there is provided a substantially non-aqueous, non-alcoholic non-silicone foamable carrier composition comprising:
(1) a petrolatum or mixtures thereof at a concentration of about 50% to about 95% by weight prior to the addition of propellant;
(2) a solvent substantially miscible therein other than the propellant, at a concentration of about 0% to about 45% by weight prior to the addition of propellant;
(3) at least one foam agent selected from the group consisting of a surfactant, a surfactant system; a foam adjuvant and combinations thereof at a concentration of about 0.1% to about 20% by weight prior to the addition of propellant;
(4) at least one liquefied or compressed gas propellant at a concentration of about 10% to about 35% by weight of the total composition;
and
(5) an effective amount of an active pharmaceutical agent;
and wherein the composition is resistant to centrifugation at 1000 rpm for about 10 minutes; wherein the composition is flowable or flowable to a degree and or is shakable or substantially so when stored in an aerosol container and upon release expands to form a breakable foam having no substantial or sustained cooling affect and having a foam hardness in the range of about 5 g to about 100 g.

In one or more other embodiments the formulations and foams are non-aqueous, non-silicone and non-alcoholic (being in the absence of a lower alcohol). In one or more other embodiments the formulations and foams have at least two of the three features listed.

Non-Aqueous Formulations

Foamable non-aqueous compositions are described that are non-aqueous or essentially so, are stable and able to provide some of the main attributes of a petrolatum ointment or cream in a topical foamable formulation and which can deliver a substantially uniform and stable foam without the use of an alcohol in the formulation. By "non-aqueous" or "essentially non-aqueous" it is meant that the compositions contain at most incidental and trace amounts of water. In one embodiment, the water content is very small being about less than about 5%. By "without alcohol" or "non-alcoholic" it is intended to exclude the use of lower or short chain alcohols. These compositions comprise petrolatum. The petrolatum phase is the main phase or is a major element of the carrier. The formulations can also ameliorate or overcome to a degree the look and feel of a greasy material. These compositions can provide an improved delivery system over ointments and creams.

In one or more embodiments, the foamable non-aqueous compositions are flowable or flowable to a degree and or are shakable and can expand to produce a good quality foam without the propellant having a significant cooling effect.

In one or more embodiments, the foamable non-aqueous compositions produce foams that are soft or with an improved softness.

In one or more embodiments, pharmaceutically effective amounts of one or more active pharmaceutical ingredients are incorporated into the foamable non-aqueous composition.

In one or more embodiments an active ingredient is distributed homogeneously in the composition are described.

In one or more embodiments, substantial amounts of an active ingredient are distributed homogeneously in the composition.

In one or more embodiments, foamable non-aqueous compositions are provided without a co-solvent.

In one or more embodiments, foamable non-aqueous compositions are provided in which the solvent comprises a propellant, which evaporates on expansion to produce a foam.

In one or more embodiments, the foamable non-aqueous composition is suitable for use as a base for delivery for API's, which are by their nature emulsion destabilizers, micelle destabilizers or interphase destabilizers, with relatively minimal or minor adjustment to the vehicle or in the method of preparation. Pharmaceutical salts, for example, are in general emulsion destabilizers.

The foamable non-aqueous compositions are described that improve the solubility and/or deliverability of the active pharmaceutical to a target skin, mucosa or body cavity area and/or provide an improved delivery system over ointments and creams.

The present invention relates to non-aqueous, non-alcoholic, non-silicone, foamable carriers and pharmaceutical and cosmetic compositions comprising at least, a hydrophilic carrier comprising petrolatum or mixtures thereof with a solvent substantially miscible therein, a surfactant, and a propellant with and without the addition of an active agent.

The present invention relates to non-aqueous, non-alcoholic, non-silicone, foamable carriers and pharmaceutical and cosmetic compositions comprising at least, a hydrophilic carrier comprising petrolatum or mixtures thereof with a solvent substantially miscible therein, a surfactant, and a propellant, with and without the addition of an active agent, wherein the foam produced by the carrier or pharmaceutical composition when packaged in an aerosol container and released has a foam hardness in the range of about 5 g to about 100 g. Preferably, hardness level is towards the lower part of the range reflecting relative softness. Further, in an embodiment when the resultant foam is applied to a surface it does not have any cooling or significant cooling effect.

The present invention relates to non-aqueous, non-alcoholic, non-silicone foamable carriers and pharmaceutical and cosmetic compositions comprising a petrolatum or mixtures thereof with a solvent substantially miscible therein, a surfactant, and a propellant, which can hold substantial amounts of active agents and still produce a good quality stable breakable foam.

The present invention relates to non-aqueous, non-alcoholic, non-silicone foamable carriers and pharmaceutical and cosmetic compositions with relatively high viscosity prior to addition of the propellant. In some embodiments, relatively high viscosity is a viscosity from about 12,000 CPs to about 500,000 CPs. In some embodiments, relatively high viscosity is a viscosity from about 20,000 CPs to about 500,000 CPs. In some embodiments, relatively high viscosity is a viscosity from about 50,000 CPs to about 500,000 CPs. In some embodiments, relatively high viscosity is a viscosity from about 100,000 CPs to about 500,000 CPs. In some embodiments, relatively high viscosity is a viscosity of at least about 20,000 CPs. In some embodiments, relatively high viscosity is a viscosity of at least about 50,000 CPs. In some embodiments, relatively high viscosity is a viscosity of at least about 100,000 CPs.

The present invention also relates to non-aqueous, non-alcoholic, non-silicone, foamable carriers and pharmaceutical and compositions comprising a petrolatum or mixtures thereof with a solvent substantially miscible therein, a surfactant, a propellant, wherein the propellant dissolves in the composition.

The present invention also relates to non-aqueous, non-alcoholic, non-silicone, foamable carriers and pharmaceutical and cosmetic compositions comprising a petrolatum or mixtures thereof with a solvent substantially miscible therein, a surfactant, a propellant, wherein the propellant dissolves in the composition and which when stored in a pressurized canister rapidly expands on release to produce a breakable foam.

The present invention also relates to non-aqueous, non-alcoholic, non-silicone, foamable carriers and pharmaceutical and cosmetic compositions comprising a petrolatum or mixtures thereof with a solvent substantially miscible therein, a surfactant, a propellant, wherein the propellant dissolves in the composition.

The present invention also relates to non-aqueous, non-alcoholic, non-silicone, foamable based pharmaceutical compositions comprising petrolatum with a solvent substantially miscible therein, a surfactant, a propellant, and an active agent wherein the active agent is insoluble and is distributed uniformly in the composition or, wherein the composition or a phase thereof is able at least to a very limited degree to solubilize the active agent or wherein the composition or a phase of the composition is able to a degree to solubalize the active agent.

In certain embodiments where the composition is essentially non-aqueous but contains a small amount of water the hydrophobic carrier or composition does not in certain aspects contain a non-propellant organic co-solvent.

The present invention relates to non-aqueous, non-alcoholic, non-silicone, foamable compositions wherein each composition is flowable or flowable to a degree and or is shakable or substantially shakable when stored in an aerosol container and upon release expands to form a breakable foam that effectively delivers petrolatum with a solvent substantially miscible therein, at a concentration of from about 25% to about 95% by weight of the foam. Preferably the amount of petrolatum is about more than about 35% and more preferably the amount of petrolatum is more than about 50% or more than about 55% or more than about 60%.

The present invention relates to a non-aqueous, non-alcoholic, non-silicone, foamable carrier composition comprising:
(1) a petrolatum or mixtures thereof with a solvent substantially miscible therein, at a concentration of about 25% to about 95% by weight prior to the addition of propellant;
(2) at least one surfactant or surfactant system, at a concentration of about 0.1% to about 20% by weight; prior to the addition of propellant;
(3) at least one liquefied or compressed gas propellant at a concentration of about 10% to about 35% by weight of the total composition;
and wherein the composition is stored in an aerosol container and upon release expands to form a breakable foam.

In one or more embodiments the solvent substantially miscible in petrolatum is from about 1% to about not more than 68% by weight of the composition, preferably about not more than 55%, more preferably about not more than 45% by weight of the composition.

The present invention further relates to said compositions additionally comprising one or more additional active agents.

Thus, the present invention also relates to a non-aqueous, non-alcoholic, non-silicone, foamable pharmaceutical or cosmetic composition comprising:

(1) a petrolatum or mixtures thereof with a solvent substantially miscible therein, at a concentration of about 25% to about 95% by weight prior to the addition of propellant;
(2) at least one surfactant or surfactant system; at a concentration of about 0.1% to about 20% by weight prior to the addition of propellant;
(3) at least one liquefied or compressed gas propellant at a concentration of about 10% to about 35% by weight of the total composition;
(4) at least one foam adjuvant; and
(5) an effective amount of an active pharmaceutical agent; and wherein the wherein the composition is flowable or flowable to a degree and or is shakable or substantially so when stored in an aerosol container and upon release expands to form a breakable foam.

In one or more embodiments the solvent substantially miscible in petrolatum or mixtures thereof is a hydrophobic solvent or an unctuous additive.

In a particular embodiment the solvent is an oil, preferably a therapeutically active oil. Thus, the present invention relates to said composition comprising one or more therapeutically active oils. The presence of oil on the one hand acts to soften and increase the fluidity of the petrolatum or mixtures thereof but on the other hand it significantly and substantially complicates the formulation and the selection of surfactants and other solvents and or foam adjuvants and or propellants appropriate to achieve a foam of quality.

In an embodiment the solvent comprises a mineral oil. In other embodiments the solvent comprises a therapeutic oil.

In an embodiment, the gas propellant and its amount can be significant in improving the characteristics of the foam. Indeed the propellant may itself be a solvent with respect to the foamable composition even though ultimately the propellant disappears from the composition upon release as it expands to form a breakable foam.

In an embodiment, the gas propellant comprises n butane.

In an embodiment, the gas propellant comprises a mixture of n-butane, isobutane and propane. The mixture may be varied as a man skilled in the art would appreciate.

In some embodiments, the foamable cosmetic or pharmaceutical composition is non-flammable, wherein said gas propellant contains hydrofluorocarbon.

Low Water Content Formulations

The aforesaid description of the non-aqueous formulations is also generally applicable to the low water content or substantially non-aqueous formulations herein with where necessary appropriate changes as would be appreciated by a man of the art. For example, where waterless is mentioned above the compositions further described below may also be waterless but without substantial amounts of a hydrophobic oil or where the compositions described below contain some small amount of water the compositions are formulated as an emulsion as opposed to a single phase. Similarly, where compositions above refer to a solvent which is substantially miscible in petrolatum, the compositions below are primarily concerned with hydrophilic or polar solvents. Thus, the previous section may be read and applied to these formulations with these points in mind. Other embodiments by way of example are specifically described below.

Petrolatum foamable compositions wherein the petrolatum phase is the main phase of the composition that are shakable and can expand to produce a good quality foam without the propellant having a significant cooling effect are described and can provide an improved delivery system over ointments and creams.

Petrolatum foamable and non-aqueous petrolatum foamable compositions in which the petrolatum phase is the main phase of the composition and contains an active ingredient distributed homogeneously in the composition are described. These compositions provide an improved delivery system over ointments and creams.

In one or more embodiments, petrolatum foamable compositions are provided without a cosolvent in which the petrolatum phase is the main phase of the composition and contains substantial amounts of an active ingredient distributed homogeneously in the composition.

In one or more embodiments, petrolatum foamable compositions are provided in which the solvent is a propellant, which evaporates on expansion to produce a foam. The petrolatum phase is the main phase of the composition and can contain substantial amounts of an active ingredient distributed homogeneously in the composition.

In one or more embodiments, a foamable petrolatum composition is suitable for use as a base for delivery of not merely one type of API but is adaptable for use with one or more API's from a wide range of different types of API's with relatively minimal or minor adjustment to the vehicle. For example, by altering the amount of a component or by the addition of a buffer that provides a pH at which the API is stable as would be appreciated by a person skilled in the art.

The present invention also relates to stable non-alcoholic foamable petrolatum based carriers and pharmaceutical and cosmetic compositions comprising a petrolatum or mixtures thereof, a surfactant, a propellant, with and without a solvent wherein the propellant dissolves in the composition and which when stored in a pressurized canister rapidly expands on release to produce a breakable foam.

The present invention also relates to stable non-alcoholic foamable petrolatum based carriers and pharmaceutical and cosmetic compositions comprising a petrolatum or mixtures thereof, a surfactant, a propellant, with and without a solvent wherein the propellant dissolves in the composition and which are resistant to creaming at 3000 rpm for at least 10 minutes.

The present invention also relates to stable non-alcoholic foamable petrolatum based pharmaceutical and cosmetic compositions comprising petrolatum mixtures.

The present invention also relates to stable non-alcoholic foamable petrolatum based pharmaceutical compositions comprising petrolatum, a surfactant, a solvent, a propellant, and an active agent wherein the active agent is insoluble and is distributed uniformly in the composition which does not contain a non propellant organic cosolvent.

The present invention also relates to stable non-alcoholic foamable pharmaceutical emulsion compositions comprising petrolatum, a surfactant, a solvent, a propellant, and an active agent, wherein the composition or a phase thereof is able at least to a very limited degree to solubilize the active agent; and or so that the composition does not comprise a non propellant organic cosolvent.

The present invention also relates to stable non-alcoholic foamable petrolatum based pharmaceutical compositions comprising a petrolatum or mixtures thereof, a surfactant, a solvent, a propellant, and an active agent wherein the composition or a phase of the composition is able to a degree to solubalize the active agent.

The present invention relates to stable non-alcoholic foamable petrolatum based compositions wherein each composition is shakable or substantially shakable stored in an aerosol container and upon release expands to form a breakable foam that effectively delivers petrolatum at a concentration of about 50% to about 95% by weight of the foam. Preferably petrolatum is delivered at a concentration of at least about 55%, and more preferably at least about 60%.

The present invention relates to stable non-alcoholic foamable petrolatum based compositions wherein each composition is flowable or flowable to a degree when stored in an aerosol container and upon release expands to form a breakable foam that effectively delivers petrolatum at a concentration of about 50% to about 95% by weight of the foam.

The present invention relates to a stable non-alcoholic foamable carrier composition comprising:

(1) a petrolatum or mixtures thereof, at a concentration of about 50% to about 95% by weight prior to the addition of propellant;
(2) at least one surfactant or surfactant system; at a concentration of about 0.1% to about 15% by weight; prior to the addition of propellant;
(3) at least one liquefied or compressed gas propellant at a concentration of about 10% to about 35% by weight of the total composition;
and wherein the composition is resistant to creaming at 3000 rpm for at least 10 minutes; wherein the composition is stored in an aerosol container and upon release expands to form a breakable foam.

The present invention further relates to said compositions comprising in addition a solvent, preferably water or a hydrophilic solvent. In one or more embodiments the solvent is about not more than 40% by weight of the composition.

The present invention relates to a stable non-alcoholic foamable pharmaceutical or cosmetic composition comprising:

(1) a petrolatum or mixtures thereof, at a concentration of about 50% to about 95% by weight prior to the addition of propellant;
(2) at least one surfactant or surfactant system; at a concentration of about 0.1% to about 15% by weight prior to the addition of propellant;
(3) at least one liquefied or compressed gas propellant at a concentration of about 10% to about 35% by weight of the total composition;
(4) at least one solvent; and
(5) an effective amount of an active pharmaceutical agent;
and wherein the composition is resistant to creaming at 3000 rpm for at least 10 minutes; wherein the composition is flowable or flowable to a degree when stored in an aerosol container and upon release expands to form a breakable foam. In an alternative embodiment the carrier composition is shakable or substantially so.

The present invention further relates to said composition comprising one or more additional therapeutically active oils.

In an embodiment the active agent is an alcoholic extract, an aqueous extract or an aqueous alcoholic extract. In such limited circumstances the amount of water or lower alcohol is permitted to the extent necessary to deliver an effective amount of the API.

In an embodiment these substantially non-aqueous formulations and foams are also non-silicone and or non-alcoholic or substantially so.

Methods of Treatment Using Non-Aqueous and Substantially Non-Aqueous Compositions The present invention further provides a method of treating, alleviating or preventing a disorder of mammalian subject, comprising administering a therapeutically effective amount of the herein-mentioned compositions to an afflicted target site.

The present invention further provides a method of treating, alleviating or preventing a nappy rash of mammalian subject, comprising administering a therapeutically effective amount of the herein-mentioned compositions to an afflicted target site. In an embodiment the petrolatum based composition contains Zinc Oxide as an API for use against or to treat or prevent minor skin irritations (e.g., burns, cuts, poison ivy, rash, particularly diaper or nappy rash). The compositions described herein are ideal for carrying effective high concentrations of API.

The present invention further provides a use of any of the herein-mentioned compositions for the manufacture of a medicament for treating, alleviating or preventing a disorder of a mammalian subject in need thereof.

The present invention further provides a use of any of the herein-mentioned compositions for the manufacture of a medicament for treating, alleviating or preventing nappy rash of a mammalian subject in need thereof.

In one or more embodiments any of the foregoing methods of treatment may be applied by providing a first pharmaceutical composition in a first foam canister and a second pharmaceutical composition in a second canister. The contents of each canister may be applied individually in an appropriate sequence or at the same time. The canisters may be part of a dual or multi chamber foam delivery device.

DETAILED DESCRIPTION

Non-Aqueous Formulations

Figure 1A:
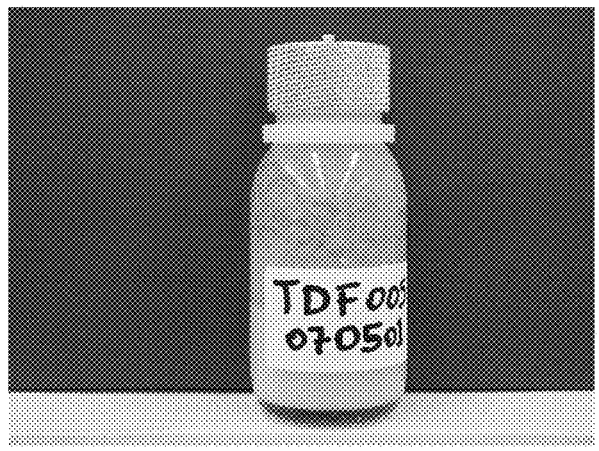
FIGS. 1a and 1b are pictures of two elevations (vertical and horizontal) of a waterless oil relatively low petrolatum carrier composition with Aluminum starch octenyl succinate ("ASOS") comprising a propellant, which shows that the formulation is homogeneous and liquid. The formulation is presented in Example 1.

The present invention provides safe and effective foamable petrolatum based pharmaceutical and cosmetic vehicles and compositions. More particularly, it provides non-aqueous, non-alcoholic, non-silicone or essentially so, foamable petrolatum based pharmaceutical or cosmetic carriers and compositions in which a petrolatum or mixtures thereof is the largest single component or is a substantial or major component by weight in the carrier or composition. The present invention further provides low water content foamable petrolatum based pharmaceutical or cosmetic carriers in which a petrolatum or mixture thereof is the largest single component or is a substantial or major component by weight in the carrier or composition. The vehicle or composition further comprises at least one surfactant or surfactant system. The vehicle or composition further comprises at least one propellant wherein the composition is stored in an aerosol container and upon release expands to form a foam. In one or more embodiments the carrier or composition further comprises one or more active agents which may be insoluble, at least soluble to a very limited degree or soluble in the composition or a phase thereof.

By low water content or essentially non-aqueous it is intended the formulations may have present a small amount of water (i.e., incidental or trace amounts of water). In one embodiment, the formulations have less than about 5% water content. In one embodiment, the formulations have less than about 4% water content. In one embodiment, the formulations have less than about 3% water content. In one embodiment, the formulations have less than about 2% water content. In one embodiment, the formulations have less than about 1% water content. In one or more embodiments where the composition is has low water content or is essentially non-aqueous it may contain a small amount of water and in certain aspects the carrier or composition does not contain a non propellant organic co-solvent.

It was unexpectedly discovered that after dissolving the propellant into pre-foam formulations without solvent so that the viscosity is high that a change in the petrolatum formulation is observed such that it is shakable and flowable. It is believed that in certain embodiments some compositions may be marginally or apparently non-shakable and still have a degree of flowability such that a good quality foam can be expelled from the canister.

The present invention also relates to foamable petrolatum based pharmaceutical and cosmetic compositions comprising petrolatum mixtures. By combining appropriate amounts of different types of petrolatum with a solvent substantially miscible therein it is possible for example, to prepare foams which are able to mimic substantially barrier properties of petrolatum ointments and petrolatum based barrier creams for nappy rash. In one embodiment a low melting point petrolatum is mixed with a petrolatum with a higher melting point. In certain embodiments the major petrolatum is the lower molecular weight petrolatum. In other embodiments the petrolatum is mixed in a ratio for example, of about 5:1; 4:1; 3:1; 2:1; or 1:1 of lower melting point to higher melting point petrolatum. In some embodiments the ratio of mixture can be of higher melting point to lower melting point. In certain embodiments a softer type of petrolatum is utilized on its own or in a mixture.

In an embodiment it was surprisingly found that it was possible to exclude stabilizers other than a surfactant and still prepare a reasonable foam in the presence of ASOS, which whilst improving skin feel can ameliorate foam quality In one or more embodiments it is possible to incorporate uniformly into a petrolatum based foamable vehicle, pharmaceutically or cosmetically effective amounts of one or more active cosmetic, therapeutic or pharmaceutical ingredients (agents).

In one or more embodiments it is possible to incorporate uniformly into a petrolatum based foamable vehicle, substantial amounts of one or more active ingredients.

In one or more embodiments it is possible to deliver uniformly in a foam produced from a petrolatum based foamable vehicle, an amount of active ingredients of up to about 33% preferably up to 20% by weight of the composition before addition of propellant.

In one or more embodiments, the foamable carriers described herein are suitable for use as a base for delivery of not merely one type of API but are adaptable for use with one or more API's from a wide range of different types of API's with relatively minimal or minor adjustment to the carrier, for example, by altering the amount of a component, as would be appreciated by a person skilled in the art. Although pH applies to aqueous environments in one or more embodiments the presence of a buffer or pH agent can also help to provide a stable environment for an active agent. In a preferred aspect the buffer or pH agent is provided in an effective amount that provides a pH at which the API is stable. Likewise chelating agents, antioxidants and anti-ionization agents may also be usefully added In one or more embodiments there is provided a foamable vehicle or carrier that is suitable for use as a base for delivery for API's, which are by their nature destabilizes, with relatively minimal or minor adjustment to the vehicle or in the method of preparation. Pharmaceuticals that have a hydrophobic region may be absorbed at least partially by the hydrophobic carrier compositions. Thus, the identification of petrolatum based compositions that are effective in having anti destabilization properties in combination with at least one surfactant or surfactant system provides special advantages and is another embodiment.

In one or more embodiments there is provided a non-aqueous, non-alcoholic, non-silicone, foamable carrier composition comprising:
(1) a petrolatum or mixtures thereof with a solvent substantially miscible therein, at a concentration of about 25% to about 95% by weight prior to the addition of propellant;
(2) at least one surfactant or surfactant system; at a concentration of about 0.1% to about 20% by weight; prior to the addition of propellant;
(3) at least one liquefied or compressed gas propellant at a concentration of about 10% to about 35% by weight of the total composition;
and wherein the composition is stored in an aerosol container and upon release expands to form a breakable foam.

In certain embodiments the foamable carriers and compositions described herein are resistant to centrifugation at 1000 rpm for at least 10 minutes, for example, when the petrolatum concentration is relatively high.

In one or more embodiments there is provided a non-aqueous, non-alcoholic, non-silicone, foamable carrier composition comprising:
(1) a petrolatum or mixtures thereof with a solvent substantially miscible therein, at a concentration of about 20% to about 95% by weight prior to the addition of propellant;
(2) at least one surfactant or surfactant system; at a concentration of about 0.1% to about 20% by weight prior to the addition of propellant;
(3) at least one liquefied or compressed gas propellant at a concentration of about 10% to about 35% by weight of the total composition;
(4) at least one foam adjuvant; and
(5) an effective amount of an active pharmaceutical agent;
and wherein the composition is flowable or flowable to a degree and or is shakable or substantially so when stored in an aerosol container and upon release expands to form a breakable foam having a foam hardness in the range of about 5 g to about 100 g.

A breakable foam is thermally stable or substantially so, yet breaks under shear force. The breakable foam is not "quick breaking", i.e., it does not readily collapse upon exposure to body temperature environment. Shear-force breakability of the foam is clearly advantageous over thermally induced breakability, (due to, for example, the presence of alcohol) since it allows comfortable application and well directed administration to the target area.

'Shakability' in the context herein means that the composition contains some or sufficient flow to allow the composition to be mixed or remixed on shaking By shakable it indicates that some motion or movement of the formulation can be sensed when the canister containing the formulation is shaken or is firmly shaken.

In one or more embodiments there is provided a non-aqueous, non-alcoholic, non-silicone, foamable carrier composition comprising:

(1) a petrolatum or mixtures thereof with a solvent substantially miscible therein, at a concentration of about 50% to about 95% by weight prior to the addition of propellant;
(2) at least one surfactant or surfactant system; at a concentration of about 0.1% to about 20% by weight prior to the addition of propellant;
(3) at least one liquefied or compressed gas propellant at a concentration of about 10% to about 35% by weight of the total composition;
(4) at least one foam adjuvant; and
(5) an effective amount of an active pharmaceutical agent;
and wherein the composition is resistant to centrifugation at 1000 rpm for at least 10 minutes; wherein the composition is flowable or flowable to a degree and or is shakable or substantially so when stored in an aerosol container and upon release expands to form a breakable foam.

In one or more embodiments the foamable carriers and compositions described herein are stored in an aerosol container and upon release expands to form a breakable foam having a foam hardness in the range of about 5 g to about 100 g.

In a further embodiment the foam hardness is in the range of about 10 g to about 90 g or more preferably about 15 g to about 55 g.

In a further embodiment the petrolatum or mixture thereof influences foam hardness such that the foam produced is soft. Softness especially with stability improves usability. If the foam, for example, is intended upon application to form a barrier, the attribute of softness should be adjusted, balanced, increased or reduced with the need to provide an effective barrier. A little less softness can be achieved, for example, by adding a proportion of petrolatum with a higher melting point or increasing the amount of waxy or solid surfactant. Alternatively it may be achieved by reducing the amount of solvent or liquid surfactant. To the extent liquid surfactant is reduced it may be compensated by increasing solid or waxy surfactant or by addition of foam adjuvants.

In a further embodiment petrolatum or mixtures thereof is between about 57% to about 90% by weight of the foamable carrier (i.e., prior to the addition of propellant).

In a further embodiment petrolatum or mixtures thereof is preferably between about 57% to about 82% by weight of the foamable carrier.

In a further embodiment the surfactant or surfactant system is preferably between about 3% to about 15% by weight of the foamable carrier (i.e., prior to the addition of propellant).

The ratio between the petrolatum and solvent is determined according to the desirable level of petrolatum and the importance of the solvent from one or more non limiting aspects including, therapeutic effect, liquefying effect, hardness, resistance to centrifugation, enhancing solubility or penetration, and taking into account appropriate and desirable pharmacologic and safety properties of the product. Typically, the solvent to petrolatum ranges between about 3:1 and about 1:100, for example, about 3:1, about 2:1, about 1:1, about 1:2, about 1:3, about 1:4, about 1:5 about, about 1:10; about 2:25, about 1:15, about 2:35, about 1:20, about 2:45 and about 1:25, about 1:30; about 1:40 about 1:50; about 1:60; about 1:70; about 1:80; about 1:90; about 1:100 preferably between about 1:15 to about 1:60.

In one or more embodiments the solvent is a PPG alkyl ether, preferably PPG15 stearyl ether.

In one or more embodiments the solvent is a combination of an oil and a PPG alkyl ether. In a preferred embodiment the oil comprises a light mineral oil and the ether comprises PPG15 stearyl ether.

In one or more embodiments the surfactant or combination of surfactants is selected from one or more of the group consisting of ceteth20, steareth 2, steareth 20, glucose methyl stearate, methyl glucose sesquistearate, Span 20, Span 80, Tween 20, and Tween 80.

In one or more embodiments the combination of surfactants is a complex emulgator.

In one or more embodiments the foam adjuvant is selected from one or more of the group consisting of oleyl alcohol, behenyl alcohol, and cetostearyl alcohol.

In one or more embodiments the foam adjuvant is selected from one or more of the group consisting of cetyl alcohol, and stearyl alcohol.

In a further embodiment the surfactant and its amount is selected so that the composition is sufficiently shakable so that substantially uniform foam extrusion is possible. In general terms, as the amount of solid or waxy surfactant is increased the shakability of the formulation reduces until a limitation point is reached where the formulation becomes non shakable and unsuitable. To this extent the maximum effective amount of surfactant that may be used may be limited by the need for shakability.

In a further embodiment the surfactant and its amount is selected so that the composition is sufficiently flowable so that substantially uniform foam extrusion is possible. In general terms, as the amount of solid or waxy surfactant is increased the flowability of the formulation reduces until a limitation point is reached where the formulation becomes non flowable and unsuitable To this extent, the maximum effective amount of surfactant that may be used may be limited by the need for some flowability.

In selecting a suitable surfactant or combination thereof it should be borne in mind that in certain exceptional embodiments the composition may be marginally shakable or apparently non shakable but nevertheless is flowable or flowable to a degree that it can flow under the pressure of the propellant through an aerosol valve to expand and form a good quality foam. This exception may be due to one or more of a number of factors such as, the high viscosity, the softness, the lack of crystals, the pseudoplastic or semi pseudo plastic nature of the composition and the dissolution of the propellant into the petrolatum. In such circumstances apart from using a standard dip tube aerosol system in certain embodiments an inverse canister system without a dip tube may be preferred and is ideal for formulations which are flowable to a degree but are apparently or marginally non shakable.

In a further embodiment the propellant or mixtures thereof and amounts thereof are selected so that the composition is sufficiently shakable so that substantially uniform foam extrusion is possible. An aspect of this embodiment is the property of the propellant to form a single phase with petrolatum.

In a further embodiment the propellant or mixtures thereof and amounts thereof are selected so that the composition is sufficiently flowable so that substantially uniform foam extrusion is possible. An aspect of this embodiment is the property of the propellant to form a single or homogeneous phase with petrolatum.

In a further embodiment the propellant and the surfactant or surfactant system and their amounts are selected so that the composition is sufficiently shakable so that substantially uniform foam extrusion is possible.

In a further embodiment the propellant and the surfactant or surfactant system and their amounts are selected so that the composition is sufficiently flowable so that substantially uniform foam extrusion is possible.

In a further embodiment the propellant is preferably between about 5% to about 30% by weight of the composition.

In a further embodiment the propellant is preferably between about 8% to about 20% by weight of the composition.

In a further embodiment the propellant is in a sufficient amount to expel the composition from the canister upon actuation to form a foam but is not sufficient to have a cooling effect on application of the foam to the skin.

In a further embodiment the foam produced from the composition or carrier is capable of remaining substantially unchanged after at least one freeze thaw cycle.

In a further embodiment the degree of solubility of the active agent is slightly, sparingly or more soluble.

In a further embodiment the degree of solubility of the active agent is very slightly soluble.

In certain embodiments where the composition has low water content or is essentially non-aqueous, the carrier or composition does not comprise a non propellant organic co-solvent.

In a further embodiment the active ingredient may be a cosmetic agent or a placebo. In which case, the carrier composition may itself be useful for the treatment prevention or amelioration of various general skin and cosmetic complaints such as aging, atopic dermatitis, contact dermatitis and radiation or burn injury and the like.

In one or more embodiments the composition further comprises one or more additional active agents. In a preferred embodiment the active agents compliment each other or may have a synergistic effect.

In one or more embodiments comprises one or more additional therapeutically active oils.

In some embodiments, the foamable cosmetic or pharmaceutical composition is non-flammable, wherein said gas propellant contains hydrofluorocarbon.

In one or more embodiments there is provided a method of treating, alleviating or preventing a disorder of mammalian subject, comprising administering a therapeutically effective amount of the above-mentioned compositions to an afflicted target site.

In one or more embodiments there is provided a method of treating, alleviating or preventing nappy rash in a mammalian subject, comprising administering a therapeutically effective amount of the above-mentioned compositions to an afflicted target site.

In one or more embodiments there is provided use of a therapeutically effective amount of the above-mentioned compositions in the manufacture of a medicament.

In one or more embodiments there is further provided a therapeutically effective amount of the above-mentioned compositions for use in the manufacture of a medicament.

In one or more embodiments the petrolatum may alone or in combination with a stabilizing agent or vica versa may help to ameliorate, counteract, or overcome undesirable effects and drawbacks of an API, such as destabilization, precipitation or breakdown.

In one or more embodiments the stabilizing agent can also assist or improve the skin feeling. Non limiting examples are polymeric agent such as ASOS, an alkyl lactate such as C-12 to C-15 alkyl lactate, a cellulose like carboxymethyl cellulose sodium and microcrystalline cellulose or methocel and xantham gum. In a preferred embodiment the polymeric agent comprises ASOS.

Additionally, in one or more embodiments there is provided foamable petrolatum based compositions that are stable and able to provide some of the main attributes of a petrolatum composition when delivered as a topical substantially uniform and stable foam and without the use of an alcohol in the formulation.

Additionally, in one or more embodiments there is provided foamable petrolatum based compositions that are stable and able to provide some of the main attributes of a petrolatum composition when delivered as a topical substantially uniform and stable foam with barrier properties and without the use of a volatile alcohol and or a volatile silicone in the formulation. In an embodiment the barrier properties are enhanced or improved by the refatting qualities of the solvent substantially miscible in the petrolatum.

In one or more embodiments a foamable pharmaceutical composition is provided also incorporating an added hydrophobic solvent, for example, as a look and feel enhancer, solubility enhancer or deliverability enhancer.

In one or more embodiments a foamable pharmaceutical composition is provided also incorporating an added polar solvent, for example, as penetration enhancer, solubility enhancer or deliverability enhancer. Preferably the enhancer is selected to be substantially miscible in the composition. In one or more embodiments the polar solvent or the potent solvent is in a small amount.

In one or more embodiments non limiting examples of other non-aqueous solvents, which preferably are added in small amounts are solvents such as polyethylene glycol (PEG), isosorbide derivatives, such as dimethyl isosorbide, propylene gycol (PG), hexylene glycol and glycerin, diethylene glycol monoethyl ether, a liquid polyethylene glycol, glycofurol, tetrahydrofurfuryl alcohol, polyethyleneglycol, ether, DMSO, a pyrrolidone, N-methyl pyrrolidones, N-Methyl-2-pyrrolidone, 1-Methyl-2-pyrrolidinone, ethyl proxitol, dimethylacetamide, a PEG-type surfactant, an alpha hydroxy acid, lactic acid and glycolic acid, hexylene glycol, benzyl alcohol, DMSO, glycofurol and ethoxydiglycol (transcutol), butylene glycols, glycerol, pentaerythritol, sorbitol, mannitol, oligosaccharides, monooleate of ethoxylated glycerides having about 8 to 10 ethylene oxide units, and cyclodextrins, esters, such as ethyl propionate, tributylcitrate, acetyl triethylcitrate, acetyl tributyl citrate, triethylcitrate, ethyl butyrate, propylene glycol monoacetate, propylene glycol diacetate, .epsilon.-caprolactone and isomers thereof, .delta.-valerolactone and isomers thereof, .beta.-butyrolactone and isomers thereof; and other solubilizers known in the art, such as dimethyl acetamide.

In an embodiment the non-aqueous solvent is monooctanoin.

In one or more embodiments a foamable pharmaceutical composition is provided wherein the ratios of surfactant, petrolatum and added polar solvent as penetration enhancer are selected or adapted to provide a selected pharmacological or safety property.

In one or more embodiments a foamable pharmaceutical composition is provided also incorporating a polymeric agent. The polymeric agent whilst it is believed to be non essential can be useful in improving foam characteristics including hardness, viscosity, and feel.

In one or more embodiments the polymeric agent is selected from a bioadhesive agent, a gelling agent, a film forming agent and a phase change agent and can be from about 0.01% to about 5% by weight.

In one or more embodiments of the pharmaceutical or cosmetic foamable product is non-flammable.

According to one or more embodiments, the foamable composition is non-alcoholic or alcohol free, i.e., free of short chain alcohols. Short chain alcohols, having up to 5 carbon atoms in their carbon chain skeleton and one hydroxyl group, such as ethanol, propanol, isopropanol, butaneol, iso-butaneol, t-butaneol and pentanol, are considered less desirable solvents or polar solvents due to their skin-irritating effect. In one or more further embodiments, the composition is substantially alcohol-free and can includes less than about 5% final concentration of lower alcohols, preferably less than about 2%, more preferably less than about 1%. Where the active ingredient is provided in an alcoholic extract then in such limited circumstances the alcoholic content may be up to about 8%.

Non-limiting benefits include:
the ability of the resultant foam to conserve of skin barrier properties;
the reduction of skin irritation;
satisfactory or increased penetration of the active or beneficial agent whilst replenishing the skin for example by moisturizing or adding fats or oils.

The ratio between the stabilizing agent or polymeric agent and petrolatum is determined according to the desirable level of petrolatum and taking into account appropriate and desirable pharmacologic and safety properties of the product. Typically, the stabilizing agent to petrolatum ranges between about 1:5 and about 1:100, for example, about 1:5, about 2:15, about 1:10, about 2:25, about 1:15, about 2:35, about 1:20, about 2:45 and about 1:25, about 1:30; about 1:40 about 1:50; about 1:60; about 1:70; about 1:80; about 1:90; about 1:100 preferably between about 1:15 to about 1:60.

Low Water Content Formulations

As indicated herein the aforesaid description of the non-aqueous formulations is also generally applicable to the low water content formulations herein with where necessary appropriate changes as would be appreciated by a man of the art. The non limiting examples given in the Summary also apply here. Thus, the previous section may be read and applied to these formulations with these points in mind. Other embodiments by way of example are specifically described below.

The present invention relates to stable non-alcoholic foamable petrolatum based carriers and pharmaceutical and cosmetic emulsion compositions comprising a petrolatum or mixtures thereof, a surfactant, and a propellant and in certain cases a solvent, with and without the addition of an active agent, wherein the foam produced by the carrier or pharmaceutical composition when packaged in an aerosol container and released has a foam hardness in the range of about 5 g to about 100 g. Unexpectedly some of the compositions show hardness measurements in the upper range and yet have a relatively soft feeling.

The present invention relates to stable non-alcoholic foamable petrolatum based carriers and pharmaceutical and cosmetic emulsion compositions with very high viscosity measurements prior to addition of the propellant. In one or more embodiments the pre foam formulation can have a wide range of viscosity from about 500,000 to about 12,000 CP or less. For example, from about 500,000 to about 300,000, from about 400,000 to about 150,000; from about 375,000 to about 225,000; from about 225,000 to about 75,000; from about 125,000 to about 12,000 or less.

It was unexpectedly discovered that after dissolving the propellant into pre foam formulations with such high viscosity that there is a change in the petrolatum such that it is shakable and flowable. It is believed that in certain embodiments some compositions may be marginally or apparently non shakable and still have a degree of flowability such that a good quality foam can be expelled from the canister.

The present invention also relates to stable non-alcoholic foamable petrolatum based pharmaceutical and cosmetic compositions comprising petrolatum mixtures. It was discovered that by combining appropriate amounts of different types of petrolatum foams which are able to mimic the barrier properties of petrolatum ointments and particularly petrolatum based barrier creams for nappy rash. In one embodiment a low melting point petrolatum is mixed with a petrolatum with a higher melting point. In certain embodiments the major petrolatum is the lower molecular weight petrolatum. In other embodiments the petrolatum is mixed in a ratio for example, of about 5:1; 4:1; 3:1; 2:1; or 1:1 of lower melting point to higher melting point petrolatum. In some embodiments the ratio of mixture can be of higher melting point to lower melting point.

In an embodiment it was surprising found that it was possible to exclude stabilizers other than a surfactant and still prepare a creamy stable foam without and with an active pharmaceutical ingredient.

In one or more embodiments there is provided a foamable vehicle that is suitable for use as a base for delivery of not merely one type of active pharmaceutical ingredient (API) but is adaptable for use with one or more API's from a wide range of different types of API's with relatively minimal or minor adjustment to the vehicle. For example, for compositions with a solvent, by altering the amount of a component or by the addition of a buffer that provides a pH in an aqueous environment or a postulated pH in a non-aqueous environment in which the API is stable and or by use of a chelating agent as is described below as would be appreciated by a person skilled in the art.

In one or more embodiments there is provided a stable non-alcoholic foamable carrier composition comprising:
(1) a petrolatum or mixtures thereof, at a concentration of about 50% to about 95% by weight prior to the addition of propellant;
(2) at least one surfactant; at a concentration of about 0.1% to about 15% by weight; prior to the addition of propellant;
(3) at least one liquefied or compressed gas propellant at a concentration of about 10% to about 35% by weight of the total composition;
and wherein the composition is resistant to creaming at 3000 rpm for at least 10 minutes; wherein the composition is stored in an aerosol container and upon release expands to form a breakable foam and wherein the carrier is shakable or substantially so.

In one or more embodiments there is provided a stable non-alcoholic foamable carrier composition comprising:
(1) a petrolatum or mixtures thereof, at a concentration of about 50% to about 95% by weight prior to the addition of propellant;
(2) at least one surfactant; at a concentration of about 0.1% to about 15% by weight; prior to the addition of propellant;
(3) at least one liquefied or compressed gas propellant at a concentration of about 10% to about 35% by weight of the total composition;
and wherein the composition is resistant to creaming at 3000 rpm for at least 10 minutes; wherein the composition is flowable or flowable to a degree when stored in an aerosol container and upon release expands to form a breakable foam.

In one or more embodiments there is provided a stable non-alcoholic foamable carrier composition comprising:
(1) a petrolatum or mixtures thereof, at a concentration of about 50% to about 95% by weight prior to the addition of propellant;
(2) at least one surfactant or surfactant system; at a concentration of about 0.1% to about 15% by weight; prior to the addition of propellant;

(3) at least one liquefied or compressed gas propellant at a concentration of about 10% to about 35% by weight of the total composition;
and wherein the composition is resistant to creaming at 3000 rpm for at least 10 minutes; wherein the composition is stored in an aerosol container and upon release expands to form a breakable foam having a foam hardness in the range of about 5 g to about 100 g and wherein the carrier is shakable or substantially so.

In one or more embodiments there is provided a stable non-alcoholic foamable pharmaceutical or cosmetic composition comprising:
(1) a petrolatum or mixtures thereof, at a concentration of about 50% to about 95% by weight prior to the addition of propellant;
(2) at least one surfactant or surfactant system; at a concentration of about 0.1% to about 15% by weight prior to the addition of propellant;
(3) at least one liquefied or compressed gas propellant at a concentration of about 10% to about 35% by weight of the total composition;
(4) at least one solvent; and
(5) an effective amount of an active pharmaceutical agent;
and wherein the carrier is resistant to creaming at 3000 rpm for at least 10 minutes; wherein the composition is stored in an aerosol container and upon release expands to form a breakable foam and wherein the carrier is shakable or substantially so.

The present invention relates to a stable non-alcoholic foamable pharmaceutical or cosmetic composition comprising:
(1) a petrolatum or mixtures thereof, at a concentration of about 50% to about 95% by weight prior to the addition of propellant;
(2) at least one surfactant or surfactant system; at a concentration of about 0.1% to about 15% by weight prior to the addition of propellant;
(3) at least one liquefied or compressed gas propellant at a concentration of about 10% to about 35% by weight of the total composition;
(4) a solvent; and
(5) an effective amount of an active pharmaceutical agent;
and wherein the composition is resistant to creaming at 3000 rpm for at least 10 minutes; wherein the composition is flowable or flowable to a degree when stored in an aerosol container and upon release expands to form a breakable foam.

In one or more embodiments there is provided a stable non-alcoholic foamable pharmaceutical or cosmetic composition comprising:
(1) a petrolatum or mixtures thereof, at a concentration of about 50% to about 95% by weight prior to the addition of propellant;
(2) at least one surfactant or surfactant system; at a concentration of about 0.1% to about 15% by weight prior to the addition of propellant;
(3) at least one liquefied or compressed gas propellant at a concentration of about 10% to about 35% by weight of the total composition;
(4) a solvent; and
(5) an effective amount of an active pharmaceutical agent;
and wherein the carrier is resistant to creaming at 3000 rpm for at least 10 minutes; wherein the composition is stored in an aerosol container and upon release expands to form a breakable foam having a foam hardness in the range of about 5 g to about 100 g and wherein the carrier is shakable or substantially so.

In a further embodiment the foam hardness is in the range of about 10 g to about 90 g or more, preferably about 30 g to about 85 g.

In a further embodiment the surfactant or surfactant system is preferably between about 1% to about 10% by weight of the composition prior to the addition of propellant.

In a further embodiment the surfactant and its amount is selected so that the composition is sufficiently shakable so that substantially uniform foam extrusion is possible. To this extent the maximum effective amount of surfactant that may be used may be limited by the need for shakability.

In a further embodiment the surfactant and its amount is selected so that the composition is sufficiently flowable so that substantially uniform foam extrusion is possible. To this extent the maximum effective amount of surfactant that may be used may be limited by the need for some flowability.

In a further embodiment the propellant is preferably between about 10% to about 30% by weight of the composition.

In a further embodiment the propellant is preferably between about 14% to about 26% by weight of the composition.

In a further embodiment the active ingredient may be partially insoluble in a phase of the emulsion. In other embodiments it may be insoluble in a phase.

In one or more embodiments a stabilizing agent may alone or in combination with petrolatum help to ameliorate, counteract, or overcome undesirable effects and drawbacks of an API, such as destabilization, on an emulsion vehicle, on a phase, on micelles or on an interphase. In one or more embodiments the stabilizing agent comprises a polymeric agent such as ASOS, an alkyl lactate such as C-12 to C-15 alkyl lactate, carboxymethyl cellulose sodium and microcrystalline cellulose or methocel and xantham gum. For example, in preparing stable non-alcoholic petrolatum foamable pharmaceutical water in oil emulsion compositions suitable for delivery of an active pharmaceutical ingredient a combination of surfactants, a metal starch, and an alkyl lactate can be used to achieve a stable foam.

When water is present the foamable composition can be an emulsion, or microemulsion, or nanoemulsion.

In an embodiment these low water content formulations and foams are also non-silicone and or non-alcoholic or substantially so.

General

Solvent and optional ingredients are added to complete the total mass of the foamable carrier to 100%.

All % values are provided on a weight (w/w) basis. In the examples the components of the composition are added to a total of 100% exclusive of the propellant.

Aging

Formulation of foam is a very delicate balance between the functional inactive ingredients, excipients, which contribute to bubble size, viscosity, hardness look and feel and stability. In order to assure accurate and continuous foam actuation, the Foam Formulation should during its intended life or use period be liquid and shakable in the canister, otherwise it will not flow easily and completely towards and through the valve. In the context of high levels of petrolatum foamable formulations it is possible as an exception for the composition to be marginally or apparently non shakable whilst the composition has a sufficient degree of flowability under pressure of the propellant that it is possible to obtain a good quality of foam.

Stability of compositions of petroleum and solvents substantiality miscible therein together with surfactants and other additives is desired. Testing for aging as reflected by creaming or phase separation whilst normally considered in the realm of emulsions may also be used to explore waterless compositions. The concept of creaming in waterless single phase compositions may be artificial and not accurately applicable and requires investigation. Resistance to creaming or phase separation can be determined by taking a sample and subjecting it to a significant G force through centrifugation to simulate accelerated aging. Waterless compositions in which petrolatum is the main component may have some inherent resistant to "creaming" or phase separation because of the physical properties of petrolatum. In the context of foamable compositions improved physical stability may be obtained by an appropriate choice of product viscosity through use of different blends of petrolatum together with one or more solvents substantially miscible in petrolatum plus a surfactant or surfactant system optionally in combination with stabilizing agents and or viscoelastic agents, which can provide suitable rheology whilst retaining the requirements of shakability or at least flowability. In the context the solvents and the surfactants used can have a considerable influence on rheology, shakability and flowability.

Where there is an emulsion, for example, when water and surfactants are formulated with petrolatum stability of emulsions and resilience to creaming is desired. Emulsions in which petrolatum is the main single component or is the main component may be inherently resistant to creaming because of the physical properties of petrolatum. In the context of foamable emulsion compositions it has been discovered that improved physical stability is obtained by an appropriate choice of product viscosity through use of different blends of petrolatum plus a surfactant or surfactant system optionally in combination with stabilizing agents and or viscoelastic agents, which can provide suitable rheology whilst retaining the requirements of shakability or at least flowability and by controlling droplet size.

By creaming it is meant that an upper layer forms. The creaming value is defined as the relative volume of the creamed phase and the total volume the sample. The expression used for calculation of the creaming volume is as follows:

$$\% \text{ Creaming} = \frac{V_{Creamed\ Phase}}{V_{total}} \times 100$$

Creaming values are between 1% and 99%, accordingly. 100% means "no creaming" which is the desirable best score. 0% (Zero value) indicates phase separation and is the worst score.

By physically durable it is intended that the formulation is capable of physically withstanding to a substantial degree at least one of centrifugation at about 1000 rpm for non-aqueous formulations and at about 3000 rpm for emulsions for about 10 minutes in each case; or one, or possibly more freeze thaw cycles; or a period of time at an elevated temperature of say 30° C. or say 40° C. for say about one month; or a prolonged period of time at room temperature for say about three months. In preferred embodiments the formulations can withstand 3 months at 30 C or 40 C and or 6 months at room temperature.

In an embodiment the composition should exhibit pseudoplastic rheological behavior.

By selective use of appropriate stabilizing surfactant, co-surfactants and optionally stabilizing polymers and foam adjuvants the compositions can be stabilized.

By appropriate selection of agents, surfactants and solvent in a petrolatum base composition to facilitate biocompatibility and to achieve the appropriate balance of physical properties, it is possible to prepare formulations that are resilient to aging when subjected to centrifugation which could be extrapolated to reflect a reasonable stable shelf life.

Petrolatum

Petrolatum is known by various names including yellow soft paraffin, yellow petrolatum, mineral jelly; and petroleum jelly. Petrolatum is a purified mixture of semisolid saturated hydrocarbons having the general formula $C_nH_{2n+2}$, and is obtained from petroleum. The hydrocarbons consist mainly of branched and unbranched chains although some cyclic alkanes and aromatic molecules with paraffin side chains may also be present. Some forms may contain a suitable stabilizer (antioxidant). It is mainly used as an emollient and ointment base in topical pharmaceutical formulations creams and transdermal applications. Therapeutically, sterile gauze dressings containing petrolatum may be used for nonadherent wound dressings. Petrolatum is additionally widely used in cosmetics and in some food applications. It is odorless, and tasteless.

The rheological properties of petrolatum are determined by the ratio of the unbranched chains to the branched chains and cyclic components of the mixture. Petrolatum contains relatively high amounts of branched and cyclic hydrocarbons, in contrast to paraffin, which accounts for its softer character and makes it an ideal ointment base. In one or more embodiments, a petrolatum or a petrolatum mixture is selected such that it has a quality of relative softness.

Petrolatum is an inherently stable material. On exposure to light any impurities present may be Oxidation may be inhibited by the inclusion of a suitable antioxidant such as butylated hydroxyanisole, butylated hydroxytoluene, or alpha tocopherol.

In preparing Petrolatum compositions they should not be heated for extended periods above the temperature necessary to achieve complete fluidity (approximately 75° C.).

Various grades of petrolatum are commercially available, which vary in their physical properties depending upon their source and refining process. Petrolatum obtained from different sources may therefore behave differently in a formulation. White petrolatum is a preferred petrolatum for use in cosmetics and pharmaceuticals, Additives, such as microcrystalline wax, may be used to add body to petrolatum.

The petrolatum used in the present invention was examined microscopically and no wax crystallization was observed. Thus, in one or more embodiments the petrolatum selected shows no tendency to wax crystallization. In one or more further embodiments the petrolatum based foamable carriers and compositions are free or substantially free of wax crystallization. In one or more further embodiments the petrolatum based foamable carriers and compositions are free or substantially free of wax crystallization when the petrolatum level is about 50% to about 95% by weight in the composition before the addition of propellant.

MMP Inc state in their sales booklet on Sofinetic™ LMP (Rev 02/05 KVB) that they conducted studies with varying grades of petroleum USP to avoid formation of wax crystals in emulsions containing 20% petrolatum and that MMP's supersoft grade incorporated into low emulsifier content formulations containing 20% petroleum has been shown to eliminate undesirable crystallization of wax. They further state that when compared to similar compositions made with a higher melting point grade of petrolatum the Sofinetic™ LMP exhibited no tendency to wax crystallization.

In certain embodiments, in the context, the term petrolatum relates to any fatty substance, having rheological properties and meting temperature patterns in the same range as described above for petrolatum.

Unctuous Additives

A "unctuous additive" as used herein refers to a greasy, fatty, waxy or oily material, including liquids, semi solids and solids which can be mixed with petrolatum to alter refine or improve the petrolatum based compositions. In one or more embodiments a small, moderate medium or lager amount of one or more unctuous additive may be blended with petrolatum provided the petrolatum remains the single largest component of the composition. In one or more other embodiments the unctuous additive can be the major component of the blend with petrolatum. Even if not the main component the properties of petrolatum at the levels of about at least 25% in the present invention it may still have a major or dominating influence on the composition. In any event unctuous additives may also have a role in effecting the solubility of an API. Unexpectedly it has been noted that in certain cases where an oil is combined with petrolatum the resultant foam has a significantly lower density.

Non limiting examples of unctuous additives that may be used in the pharmaceutical composition may be natural or synthetic or a synthetic derivative and, include higher aliphatic hydrocarbons, animal or vegetable fats, greases and oils, waxes, and combinations thereof.

In one or more embodiments, specific non limiting examples are higher aliphatic hydrocarbons, mineral jelly and fractions thereof, paraffin, squalane, ceresin, mineral oil and the like.

In one or more embodiments, specific non limiting examples of the waxes include beeswax, carnauba wax, microcrystalline wax, candilla wax, berry wax, montan wax, polyethylene wax and ethylene vinyl acetate (EVA) copolymers spermaceti, lanolin, wool wax, wool fat, wax blend, solid paraffin, oxidized wax, waxy solids or waxy semi-solids, synthetic wax's and the like.

In one or more embodiments, non limiting specific examples of the animal or vegetable fats and oils include, triglycerides, olive oil, almond oil, avocado oil, borage oil, castor oil, cocoa butter, palm oil, turtle oil, cod-liver oil, whale oil, beef tallow, butter fat, shea butter, shorea butter, and the like.

In one or more embodiments, the above-described unctuous additive may be used alone or in combination with petrolatum.

The use of high melting point hydrocarbons, such as petrolatum can be occlusive when applied to the skin. In one or more embodiments, when an extensive refatting or moisturizing effect is required, then petrolatum in concentrations of more than 25% preferably more than 50% to about 95% prior to the addition of propellant is included in the compositions.

In order to derive, develop or optimize a composition, which is readily foamable upon release from a pressurized container, additional components may also be introduced, as provided herein below.

Hydrophobic Solvents

Further in one or more embodiments petrolatum and petrolatum mixtures may also be combined with one or more hydrophobic solvents or carriers, which are materials suitable for use to blend with or act as a carrier for the petrolatum emollients. They may also have a further role in effecting the solubility of an API.

In one or more other embodiments the hydrophobic solvents or carriers are ester oils. Specific non limiting examples of the ester oils include isopropyl myristate, isopropyl palmitate, butyl stearate, hexyl laurate, octyldodecyl myristate, di-isopropyl adipate, isocetyl myristate, di-isopropyl sebacate, and the like.

In one or more other embodiments the hydrophobic solvents or carriers are higher alcohols. Specific non limiting examples of the higher alcohols include cetyl alcohol, oleyl alcohol, isostearyl alcohol, octyldodecanol and the like.

According to one or more embodiments, hydrophobic solvents or carriers are liquid oils originating from vegetable, marine or animal sources. Suitable liquid oil includes saturated, unsaturated or polyunsaturated oils. By way of example, the unsaturated oil may be olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils or mixtures thereof, in any proportion.

Suitable hydrophobic solvents or carriers also include polyunsaturated oils containing poly-unsaturated fatty acids. In one or more embodiments, the unsaturated fatty acids are selected from the group of omega-3 and omega-6 fatty acids. Examples of such polyunsaturated fatty acids are linoleic and linolenic acid, gamma-linoleic acid (GLA), eicosapentaenoic acid (EPA) and docosahexaenoic acid (DHA). Such unsaturated fatty acids are known for their skin-conditioning effect, which can contribute to the therapeutic benefit of the present foamable composition. Thus, the hydrophobic solvent can include at least 3% preferably at least 6% of an oil selected from omega-3 oil, omega-6 oil, and mixtures thereof.

In the context, oils that possess therapeutically beneficial properties are termed as "therapeutically active oil."

Another class of hydrophobic solvents or carriers is the essential oils, which are also considered therapeutically active oils, and which contain active biologically occurring molecules and, upon topical application, exert a therapeutic effect. Non-limiting examples of essential oils include rosehip oil, which contain retinoids and is known to reduce acne and post-acne scars, and tea tree oil, which possess antibacterial, antifungal and antiviral properties. Other examples of essential oils are oils of anise, basil, bergemont, camphor, cardamom, carrot, canola, cassia, catnip, cedarwood, citronella, clove, cypress, eucalyptus, frankincense, garlic, ginger, grapefruit, hyssop, jasmine, jojova, lavender, lavandin, lemon, lime, mandarin, marjoram, myrrh, neroli, nutmeg, orange, peppermint, petitgrain, rosemary, sage, spearmint, star anise, tangerine, thyme vanilla, verbena and white clover.

Another class of therapeutically active oils is liquid hydrophobic plant-derived oils, which are known to possess therapeutic benefits when applied topically.

Silicone oils also may be used and are desirable due to their known skin protective and occlusive and antifriction properties. Moreover they may mask to some extent the tacky greasy feeling of petrolatum on the skin. Suitable silicone oils include non-volatile silicones, such as polyalkyl siloxanes, polyaryl siloxanes, polyalkylaryl siloxanes and polyether siloxane copolymers, polydimethylsiloxanes (dimethicones) and poly(dimethylsiloxane)-(diphenyl-siloxane) copolymers. Silicone oils are also considered therapeutically active oil, due to their barrier retaining and protective properties. However, silicone oils are not essential. They are foam defoamers and therefore if included are ideally used in relatively small amounts, such as less than about 5% if there is more than 50% petrolatum, and in other cases where the petrolatum is under about 50% then the silicones should be less than about 1%. To counteract to some extent the defoaming properties extra surfactant and or foam adjuvant may be usefully added. If volatile silicones are used they evaporate from the skin and effect the deposited composition and can interfere with its occlusive properties and may cause dryness. In a preferred embodiment there is no silicone or less than 1%. When the level of petrolatum is at least about 50% or more then higher levels of silicone may be used.

A further class of hydrophobic solvents or carriers includes hydrophobic liquids, selected from the family of organic liquids described as "emollients." Emollients possess a softening or soothing effect, especially when applied to body areas, such as the skin and mucosal surfaces. Examples of suitable emollients include isopropyl myristate, isopropyl palmitate, isopropyl isostearate, diisopropyl adipate, diisopropyl dimerate, maleated soybean oil, octyl palmitate, cetyl lactate, cetyl ricinoleate, tocopheryl acetate, cetyl acetate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, octyl dodecanol, sucrose esters of fatty acids and octyl hydroxystearate.

In one or more embodiments the petrolatum based foamable carrier and composition comprises a hydrophobic solvent selected from the group consisting of:
1 a high-melting point hydrocarbon;
2 a liquid oil originating from vegetable, marine or animal sources;
3 an oil selected from the group consisting of (1) a saturated oil; (2) an unsaturated oil; and (3) a polyunsaturated oil;
4 an oil selected from the group consisting of olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil and evening primrose oil;
5 an poly-unsaturated fatty acid selected from the group consisting of (1) an omega-3 fatty acid and (2) an omega-6 fatty acid;
6 an poly-unsaturated fatty acid selected from the group consisting of linoleic acid, linolenic acid, gamma-linoleic acid (GLA), eicosapentaenoic acid (EPA) and docosahexaenoic acid (DHA);
7 a therapeutically active oil;
8 an essential oil;
9 an oil derived from a plant selected from the group consisting of anise, basil, bergemont, camphor, cardamom, carrot, canola, cassia, catnip, cedarwood, citronella, clove, cypress, eucalyptus, frankincense, garlic, ginger, grapefruit, hyssop, jasmine, jojova, lavender, lavandin, lemon, lime, mandarin, marjoram, myrrh, neroli, nutmeg, orange, peppermint, petitgrain, rosemary, rosehip, sage, spearmint, star anise, tea tree, tangerine, thyme vanilla, verbena and white clover;
10 a silicone oil;
11 an oil selected from the group consisting of a polyalkyl siloxane, a polyaryl siloxane, a polyalkylaryl siloxane, a polyether siloxane copolymer, a polydimethylsiloxane and a poly(dimethylsiloxane)-(diphenyl-siloxane) copolymer;
12 a hydrophobic emollient; and
13 an oil selected from the group consisting of isopropyl myristate, isopropyl palmitate, isopropyl isostearate, diisopropyl adipate, diisopropyl dimerate, maleated soybean oil, octyl palmitate, cetyl lactate, cetyl ricinoleate, tocopheryl acetate, cetyl acetate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, octyl dodecanol, sucrose esters of fatty acids and octyl hydroxystearate.

In one or more embodiments the petrolatum based foamable carrier and composition comprises a hydrophobic solvent in a moderate or larger amount.

Polypropylene Glycol (PPG) Alkyl Ethers

In the context, a polypropylene glycol alkyl ether (PPG alkyl ether) is a liquid, water-insoluble propoxylated fatty alcohol, having the molecular formula of $RO(CH_2CHOCH_3)$; wherein "R" is a straight-chained or branched $C_4$ to $C_{22}$ alkyl group; and "n" is in the range between 4 and about 50.

(PPG alkyl ethers), are organic liquids that function as skin-conditioning agent in pharmaceutical and cosmetic formulations. They possess exceptional emollient effect, side by side with enhanced solvency properties, which facilitates solubilization of active agents in a composition comprising a PPG alkyl ether. PPG alkyl ethers offer the following advantages when used as a component in the foamable composition:

Due to the polypropylene glycol moiety, PPG alkyl ethers possess certain surface active properties and they assist in the coupling of polar and non-polar oils in an emulsion formulation.

PPG alkyl ethers are non-occlusive; offering a long-lasting and velvety feel.

They are chemically stable at extreme pH conditions;

Excellent solvency properties, particularly with difficult to formulate active agents When combined with certain surfactants, such as Brij 72 and Brij 721, PPG alkyl ethers form oleosomes and/or liquid crystal structures, which provide long lasting moisturization, excellent spreading as well as prolonged hydration properties Exemplary PPG alkyl ethers include PPG-2 butyl ether, PPG-4 butyl ether, PPG-5 butyl ether, PPG-9 butyl ether, PPG-12 butyl ether, PPG-14 butyl ether, PPG-15 butyl ether, PPG-16 butyl ether, PPG-17 butyl ether, PPG-18 butyl ether, PPG-20 butyl ether, PPG-22 butyl ether, PPG-24 butyl ether, PPG-26 butyl ether, PPG-30 butyl ether, PPG-33 butyl ether, PPG-40 butyl ether, PPG-52 butyl ether, PPG-53 butyl ether, PPG-10 cetyl ether, PPG-28 cetyl ether, PPG-30 cetyl ether, PPG-50 cetyl ether, PPG-30 isocetyl ether, PPG-4 lauryl ether, PPG-7 lauryl ether, PPG-2 methyl ether, PPG-3 methyl ether, PPG-3 myristyl ether, PPG-4 myristyl ether, PPG-10 oleyl ether, PPG-20 oleyl ether, PPG-23 oleyl ether, PPG-30 oleyl ether, PPG-37 oleyl ether, PPG-50 oleyl ether, PPG-11 stearyl ether. Preferred PPG alky ethers according to the present invention include PPG-15 stearyl ether (also known as Earlamol E®, Unichema), PPG-2 butyl ether, PPG-9-13 butyl ether and PPG-40 butyl ether. PPG alkyl ethers can be incorporated in the foamable composition in a concentration preferably between about 1% and about 20%, more preferably between about 3% and about 15%.

The sensory properties of foams containing PPG alkyl ethers are favorable, as revealed by consumer panel tests.

Surprisingly, it has been discovered that PPG alkyl ethers also reduce the degree of inflammability of a foam, as demonstrated in a standard inflammability test according to European Standard prEN 14851, titled "Aerosol containers. According to this standard, a product is considered inflammable if a stable flame appears following ignition, which is at least 4 cm high and which is maintained for at least 2 seconds. In an embodiment, the concentration of the PPG alkyl ether is sufficient to reduce the degree of inflammability, of a composition when compared with the same composition without the PPG alkyl ether.

Surface Active Agent

The composition further contains a surface-active agent. Surface-active agents (also termed "surfactants") include any agent linking oil and water in the composition, in the form of emulsion. A surfactant's hydrophilic/lipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average). In many cases a single surfactant may suffice. In other cases a combination of two or more surfactants is desired. Reference to a surfactant in the specification can also apply to a combination of surfactants or a surfactant system. As will be appreciated by a person skilled in the art which surfactant or surfactant system is more appropriate is related to the vehicle and intended purpose. In general terms a combination of surfactants is usually preferable where the vehicle is an emulsion. In an emulsion environment a combination of surfactants can be significant in producing breakable forms of good quality. In a waterless or substantially waterless environment it has been discovered that the presence of a surfactant or combination of surfactants can also be significant in producing breakable forms of good quality. It has been further discovered that the generally thought considerations for HLB values for selecting a surfactant or surfactant combination are not always binding for emulsions and that good quality foams can be produced with a surfactant or surfactant combination both where the HLB values are in or towards the lipophilic side of the scale and where the HLB values are in or towards the hydrophilic side of the scale.

It has been further discovered that the physical nature of the surfactant or combination thereof can affect the quality of foam produced. For example and in very general oversimplified terms the presence of a solid or waxy surfactant may help where the composition is more liquid or less viscous in nature and similarly where a formulation is less liquid and more viscous the presence of a liquid surfactant may help. More particularly a combination of a solid or waxy surfactant with a liquid surfactant may be of significance and the ratio between them may be adjusted to take into account to an extent whether the composition is otherwise more liquid or otherwise more viscous in nature. The position is more complex than this since the presence and interaction of other agents such as foam adjuvants, polymeric agents as well as unctuous additives and hydrophobic agents all have an influence on achieving a breakable foam of quality According to one or more embodiments the composition contains a single surface active agent having an HLB value between about 2 and 9, or more than one surface active agent and the weighted average of their HLB values is between about 2 and about 9. Lower HLB values may in certain embodiments be more applicable.

According to one or more embodiments the composition contains a single surface active agent having an HLB value between about 7 and 14, or more than one surface active agent and the weighted average of their HLB values is between about 7 and about 14. Mid range HLB values may in certain embodiments be more suitable.

According to one or more other embodiments the composition contains a single surface active agent having an HLB value between about 9 and about 19, or more than one surface active agent and the weighted average of their HLB values is between about 9 and about 19. In a waterless or substantially waterless environment a wide range of HLB values may be suitable.

According to one or more embodiments a wide range of HLB values giving about an average mid range can be achieved with combinations of two, three or more surfactants. For example, the following provides an average of 9.36:

| | |
|---|---|
| Behenyl alcohol | 1.9 |
| ceteth 20 | 15.7 |
| steareth 2 | 4.7 |
| GMS | 3.4 |
| Span 80 | 4.3 |
| Tween 20 | 16.7 |

Preferably, the composition contains a non-ionic surfactant. Nonlimiting examples of possible non-ionic surfactants include a polysorbate, polyoxyethylene (20) sorbitan monostearate, sorbitan monostearate, polyoxyethylene (20) sorbitan monooleate, sorbitan laurate; a polyoxyethylene fatty acid ester, Myrj 45, Myrj 49, Myrj 52 and Myrj 59; a polyoxyethylene alkyl ether, polyoxyethylene cetyl ether, polyoxyethylene palmityl ether, polyethylene oxide hexadecyl ether, polyethylene glycol cetyl ether, stearaths such as steareth 2, brij 21, brij 721, brij 38, brij 52, brij 56 and brij W1, behenyl alcohol; a sucrose ester, a partial ester of sorbitol and its anhydrides, sorbitan monolaurate, sorbitan monolaurate, a monoglyceride, a diglyceride, isoceteth-20 and mono-, di- and tri-esters of sucrose with fatty acids. In certain embodiments, suitable sucrose esters include those having high monoester content, which have higher HLB values.

In certain embodiments, surfactants are selected which can provide a close packed surfactant layer. To achieve such objectives combinations of at least two surfactants are selected. Preferably, they should be complex emulgators and more preferably they should both be of a similar molecular type; for example, a pair of ethers, like steareth 2 and steareth 21, or a pair of esters, for example, PEG-40 stearate and polysorbate 80. Ideally, the surfactants can be ethers. In certain circumstances POE esters cannot be used and a combination of sorbitan laurate and sorbitan stearate or a combination of sucrose stearic acid ester mixtures and sodium laurate may be used. All these combinations due to their versatility and strength may also be used satisfactorily and effectively with ether formulations, although the amounts and proportion may be varied according to the formulation and its objectives as will be appreciated by a man of the art.

It has been discovered also that by using a derivatized hydrophilic polymer with hydrophobic alkyl moieties as a polymeric emulsifier such as pemulen it is possible to stabilize the emulsion better about or at the region of phase reversal tension. Other types of derivatized polymers like silicone copolymers, derivatized starch [Aluminum Starch Octenylsuccinate (ASOS)]/[DRY-FLO AF Starch], and derivatized dexrin may also a similar stabilizing effect.

A series of dextrin derivative surfactants prepared by the reaction of the propylene glycol polyglucosides with a hydrophobic oxirane-containing material of the glycidyl ether are highly biodegradable. [Hong-Rong Wang and Keng-Ming Chen, Colloids and Surfaces A: Physicochemical and Engineering Aspects Volume 281, Issues 1-3, 15 Jun. 2006, Pages 190-193].

Non-limiting examples of non-ionic surfactants that have HLB of about 7 to about 12 include steareth 2 (HLB~4.9); glyceryl monostearate/PEG 100 stearate (Av HLB~11.2); stearate Laureth 4 (HLB~9.7) and cetomacrogol ether (e.g., polyethylene glycol 1000 monocetyl ether). More exemplary stabilizing surfactants which may be suitable for use in the present invention are found below.

PEG-Fatty Acid Monoester Surfactants

| Chemical name | Product example name | HLB |
|---|---|---|
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-45 stearate | Nikkol MYS-45 (Nikko) | 18 |
| PEG-50 stearate | Myrj 53 | >10 |
| PEG-100 stearate | Myrj 59, Arlacel 165 (ICI) | 19 |

PEG-Fatty Acid Diester Surfactants:

| Chemical name | Product example name | HLB |
|---|---|---|
| PEG-4 dilaurate | Mapeg .RTM. 200 DL (PPG), Kessco .RTM.PEG 200 DL (Stepan), LIPOPEG 2-DL (Lipo Chem.) | 7 |
| PEG-4 | distearate Kessco .RTM. 200 DS (Stepan.sub) | 5 |
| PEG-32 dioleate | Kessco .RTM. PEG 1540 DO (Stepan) | 15 |
| PEG-400 dioleate | Cithrol 4DO series (Croda) | >10 |
| PEG-400 disterate | Cithrol 4DS series (Croda) | >10 |
| PEG-20 glyceryl oleate | Tagat .RTM. O (Goldschmidt) | >10 |

Transesterification Products of Oils and Alcohols

| Chemical name | Product example name | HLB |
|---|---|---|
| PEG-30 castor oil | Emalex C-30 (Nihon Emulsion) | 11 |
| PEG-40 hydrogenated castor oil | Cremophor RH 40 (BASF), Croduret (Croda), Emulgin HRE 40 (Henkel) | 13 |

Polyglycerized Fatty Acids, such as:

| Chemical name | Product example name | LB |
|---|---|---|
| Polyglyceryl-6 dioleate | Caprol .RTM. 6G20 (ABITEC); PGO-62 (Calgene), PLUROL OLEIQUE CC 497 (Gattefosse)Hodag | 8.5 |

PEG-Sorbitan Fatty Acid Esters

| Chemical name | Product example name | HLB |
|---|---|---|
| PEG-20 sorbitan monopalmitate | Tween 40 (Atlas/ICI), Crillet 2 (Croda) | 16 |
| PEG-20 sorbitan monostearate | Tween-60 (Atlas/ICI), Crillet 3 (Croda) | 15 |
| PEG-20 sorbitan | Tween-80 (Atlas/ICI), Crillet 4 (Croda) | 15 |
| PEG-20 sorbitan | Tween-80 (Atlas/ICI), Crillet 4 (Croda) | 15 |

Polyethylene Glycol Alkyl Ethers

| Chemical name | Product example name | HLB |
|---|---|---|
| PEG-2 oleyl ether | oleth-2 Brij 92/93 (Atlas/ICI) | 4.9 |
| PEG-3 oleyl ether | oleth-3 Volpo 3 (Croda) | <10 |
| PEG-5 oleyl ether | oleth-5 Volpo 5 (Croda) | <10 |
| PEG-10 oleyl ether | oleth-10 Volpo 10 (Croda), Brij 96/97 (Atlas/ICI) | 12 |
| PEG-20 oleyl ether | oleth-20 Volpo 20 (Croda), Brij 98/99 (Atlas/ICI) | 15 |
| PEG-4 lauryl ether | Laureth-4Brij 30 (Atlas/ICI) | 9.7 |
| PEG-23 lauryl ether | Laureth-23Brij 35 (Atlas/ICI) | 17 |
| PEG-10 stearyl ether | Brij 76 (ICI) | 12 |
| PEG-2 cetyl ether | Brij 52 (ICI) | 5.3 |

Sugar Ester Surfactants

| Chemical name | Product example name | HLB |
|---|---|---|
| Sucrose distearate | Sisterna SP50, Surfope 1811 | 11 |

Sorbitan Fatty Acid Ester Surfactants

| Chemical name | Product example name | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |

In one or more embodiments the surface active agent is a complex emulgator in which the combination of two or more surface active agents can be more effective than a single surfactant and provides a more stable emulsion or improved foam quality than a single surfactant. For example and by way of non-limiting explanation it has been found that by choosing say two surfactants, one hydrophobic and the other hydrophilic the combination can produce a more stable emulsion than a single surfactant. Preferably, the complex emulgator comprises a combination of surfactants wherein there is a difference of about 4 or more units between the HLB values of the two surfactants or there is a significant difference in the chemical nature or structure of the two or more surfactants.

Specific non limiting examples of surfactant systems are, combinations of polyoxyethylene alkyl ethers, such as Brij 59/Brij 10; Brij 52/Brij 10; Steareth 2/Steareth 20; Steareth 2/Steareth 21 (Brij 72/Brij 721); combinations of polyoxyethylene stearates such as Myrj 52/Myrj 59; combinations of sucrose esters, such as Surphope 1816/Surphope 1807; combinations of sorbitan esters, such as Span 20/Span 80; Span 20/Span 60; combinations of sucrose esters and sorbitan esters, such as Surphope 1811 and Span 60; combinations of liquid polysorbate detergents and PEG compounds, such as Tween 80/PEG-40 stearate; methyl glucaso sequistearate; polymeric emulsifiers, such as Permulen (TR1 or TR2); liquid crystal systems, such as Arlatone (2121), Stepan (Mild RM1), Nikomulese (41) and Montanov (68) and the like.

In certain embodiments the surfactant is preferably a combination of steareth-2 and steareth-21; in certain other embodiments the surfactant is a combination of polysorbate 80 and PEG-40 stearate. In certain other embodiments the surfactant is a combination of glyceryl monostearate/PEG 100 stearate.

In one or more embodiments the stability of the composition can be improved when a combination of at least one non-ionic surfactant having HLB of less than 9 and at least one non-ionic surfactant having HLB of equal or more than 9 is employed. The ratio between the at least one non-ionic surfactant having HLB of less than 9 and the at least one non-ionic surfactant having HLB of equal or more than 9, is between 1:8 and 8:1, or at a ratio of 4:1 to 1:4. The resultant HLB of such a blend of at least two emulsifiers is preferably between about 9 and about 14.

Thus, in an exemplary embodiment, a combination of at least one non-ionic surfactant having HLB of less than 9 and at least one non-ionic surfactant having HLB of equal or more than 9 is employed, at a ratio of between 1:8 and 8:1, or at a ratio of 4:1 to 1:4, wherein the HLB of the combination of emulsifiers is preferably between about 5 and about 18.

In certain cases, the surface active agent is selected from the group of cationic, zwitterionic, amphoteric and ampholytic surfactants, such as sodium methyl cocoyl taurate, sodium methyl oleoyl taurate, sodium lauryl sulfate, triethanolamine lauryl sulfate and betaines.

Many amphiphilic molecules can show lyotropic liquid-crystalline phase sequences depending on the volume balances between the hydrophilic part and hydrophobic part. These structures are formed through the micro-phase segregation of two incompatible components on a nanometer scale. Soap is an everyday example of a lyotropic liquid crystal. Certain types of surfactants tend to form lyotropic liquid crystals in emulsions interface (oil-in-water) and exert a stabilizing effect. Non limiting examples of surfactants with postulated tendency to form interfacial liquid crystals are: phospholipids, alkyl glucosides, sucrose esters, sorbitan esters. In certain embodiments surfactants which tend to form liquid crystals may improve the quality of foams produced.

In one or more embodiments the surfactant is a surfactant or surfactant combination is capable of or which tends to form liquid crystals.

In one or more embodiments the at least one surface active agent is liquid.

In one or more embodiments the at least one surface active agent is solid, semi solid or waxy.

It should be noted that HLB values may not be so applicable to non ionic surfactants, for example, with liquid crystals or with silicones.

In one or more embodiments the surfactant can be, a surfactant system comprising of a surfactant and a co surfactant, a waxy emulsifier, a liquid crystal emulsifier, an emulsifier which is solid or semi solid at room temperature and pressure, or combinations of two or more agents in an appropriate proportion as will be appreciated a person skilled in the art. Where a solid or semi solid emulsifier combination is used it can also comprise a solid or semi solid emulsifier and a liquid emulsifier.

In one or more embodiments, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. Non-ionic surfactants alone can provide formulations and foams of good or excellent quality in the carriers and compositions described herein.

Thus, in a preferred embodiment, the surface active agent, the composition contains a non-ionic surfactant. In another preferred embodiment the composition includes a mixture of non-ionic surfactants as the sole surface active agent. Yet, in additional embodiments, the foamable composition includes a mixture of at least one non-ionic surfactant and at least one ionic surfactant in a ratio in the range of about 100:1 to 6:1. In one or more embodiments, the non-ionic to ionic surfactant ratio is greater than about 6:1, or greater than about 8:1; or greater than about 14:1, or greater than about 16:1, or greater than about 20:1. In further embodiments, surface active agent comprises a combination of a non-ionic surfactant and an ionic surfactant, at a ratio of between 1:1 and 20:1.

In one or more embodiments, a combination of a non-ionic surfactant and an ionic surfactant (such as sodium lauryl sulphate and cocamidopropylbetaine) is employed, at a ratio of between 1:1 and 20:1, or at a ratio of 4:1 to 10:1; for example, about 1:1, about 4:1, about 8:1, about 12:1, about 16:1 and about 20:1 or at a ratio of 4:1 to 10:1, for example, about 4:1, about 6:1, about 8:1 and about 10:1.

In selecting a suitable surfactant or combination thereof it should be borne in mind that the upper amount of surfactant that may be used may be limited by the shakability of the composition. In general terms, as the amount of non liquid surfactant is increased the shakability of the formulation reduces until a limitation point is reached where the formulation becomes non shakable and unsuitable. Thus in an embodiment any effective amount of surfactant may be used provided the formulation remains shakable. In other certain exceptional embodiments the upper limit may be determined by flowability such as in circumstances where the composition is marginally or apparently non shakable. Thus in an embodiment any effective amount of surfactant may be used provided the formulation remains flowable.

In certain embodiments the amount of surfactant or combination of surfactants is between about 0.05% to about 20%; between about 0.05% to about 15%. or between about 0.05% to about 10%. In a preferred embodiment the concentration of surface active agent is between about 0.2% and about 8%. In a more preferred embodiment the concentration of surface active agent is between about 1% and about 6%.

If the composition as formulated is a substantially non shakable composition it is nevertheless possible as an exception in the scope for the formulation to be flowable to a sufficient degree to be able to flow through an actuator valve and be released and still expand to form a good quality foam. This surprising and unusual exception may be due one or more of a number of factors such as the high viscosity, the softness, the lack of crystals, the pseudoplastic or semi pseudo plastic nature of the composition and the dissolution of the propellant into the petrolatum.

In one or more embodiments, the surface-active agent includes mono-, di- and tri-esters of sucrose with fatty acids (sucrose esters), prepared from sucrose and esters of fatty acids or by extraction from sucro-glycerides. Suitable sucrose esters include those having high monoester content, which have higher HLB values.

Single Phase Compositions and Solvents; Emulsions ((a) w/o; o/w (b) Non-Aqueous)

In one or more embodiments the carrier or composition is non-aqueous or essentially so and comprises a single phase.

In one or more embodiments the carrier or composition comprises a solvent substantially miscible in petrolatum.

In one or more non-aqueous embodiments the carrier or composition comprises a hydrophobic solvent in petrolatum wherein preferably the solvent is an unctuous additive or an oil.

In one or more embodiments the solvent is a PPG alkyl ether, preferably PPG15 stearyl ether.

In one or more embodiments the solvent is a combination of an unctuous additive and or an oil and or a PPG alkyl ether. In a preferred embodiment the combination is of an oil and a PPG alkyl ether. Preferably the oil comprises a light mineral oil and the ether comprises PPG15 stearyl ether.

In one or more embodiments of the present invention the carrier or composition comprises a single phase.

In one or more embodiments of the present invention the carrier or composition comprises an emulsion.

In one or more embodiments of the present invention the carrier or composition comprises a solvent in petrolatum emulsion.

In one or more embodiments of the present invention the carrier or composition comprises a solvent in petrolatum emulsion wherein the solvent is selected from water or a non-aqueous solvent In one or more embodiments of the present invention the carrier or composition comprises water in petrolatum emulsion.

In one or more embodiments of the present invention the carrier or composition comprises a unique solvent in petrolatum emulsion wherein the solvent is a non-aqueous solvent.

In one or more embodiments of the present invention the carrier or composition comprises a unique hydrophillic solvent in petrolatum emulsion.

In one or more embodiments of the present invention non limiting examples of the non-aqueous solvent are solvents such as polyethylene glycol (PEG), isosorbide derivatives, such as dimethyl isosorbide, propylene gycol (PG), hexylene glycol and glycerin, diethylene glycol monoethyl ether, a liquid polyethylene glycol, glycofurol, tetrahydrofurfuryl alcohol, polyethyleneglycol, ether, DMSO, a pyrrolidone, N-methylpyrrolidones, N-Methyl-2-pyrrolidone, 1-Methyl-2-pyrrolidinone, ethyl proxitol, dimethylacetamide, a PEG-type surfactant, an alpha hydroxy acid, lactic acid and glycolic acid, hexylene glycol, benzyl alcohol, DMSO, glycofurol and ethoxydiglycol (transcutol), butylene glycols, glycerol, pentaerythritol, sorbitol, mannitol, oligosaccharides, monooleate of ethoxylated glycerides having about 8 to 10 ethylene oxide units, and cyclodextrins, esters, such as ethyl propionate, tributylcitrate, acetyl triethylcitrate, acetyl tributyl citrate, triethylcitrate, ethyl butyrate, propylene glycol monoacetate, propylene glycol diacetate, .epsilon.-caprolactone and isomers thereof, .delta.-valerolactone and isomers thereof, .beta.-butyrolactone and isomers thereof; and other solubilizers known in the art, such as dimethyl acetamide.

In an embodiment of the present invention the non-aqueous solvent is monooctanoin.

In one or more embodiments of the present invention the carrier or composition comprises a unique hydrophillic solvent in petrolatum emulsion, wherein the hydrophilic solvent is selected from a liquid polyethylene glycol, a propylene glycol or dimethyl isosorbide.

Stabilizing Agent

A stabilizing agent is an agent that may have to some extent one or more of the properties of foam adjuvant, friction ameliorator, gelling agent, look and feel ameliorator, lubricant, stabilizer, anti-destabilizer, surfactant, thickener and viscosity modifier or enhancer.

In one embodiment the stabilizing agent may help to ameliorate, counteract, or overcome undesirable effects and drawbacks of using an petrolatum emollient.

In one or more embodiments, the stabilizing agent can be, a polymer or a polymeric agent; more specifically it can be an alkyl lactate for example a C12-15 alkyl lactate, a metal starch for example ASOS or similar polymeric derivatives; a hydrophobic starch; a microcrystalline cellulose; a cellulose ether and or long chain polysaccharide; a (alpha-tocopheryl polyethylene glycol succinate); polyoxyethylene alkyl ethers and crosslinked polyacrylic acid polymers and the like.

Modulating Agent

The term modulating agent is used to describe an agent which can improve the stability of or stabilize a foamable carrier or composition and or an active agent by modulating the effect of a substance or residue present in the carrier or composition.

In one or more embodiments the modulating agent is used in a water in oil (petrolatum) emulsion. In one or more other embodiments the modulating agent is used in a unique waterless emulsion.

In certain embodiments the substance or residue may for example be acidic or basic and potentially alter pH in an emulsion environment or it may be one or more metal ions which may act as a potential catalyst in an emulsion environment.

In certain other embodiments the substance or residue may for example be acidic or basic and potentially alter an artificial pH in a waterless or low water content environment or it may be one or more metal ions which may act as a potential catalyst in a waterless or low water content environment.

In one or more embodiments the modulating agent is used to describe an agent which can affect pH in an aqueous solution. The agent can be any of the known buffering systems used in pharmaceutical or cosmetic formulations as would be appreciated by a man of the art. It can also be an organic acid, a carboxylic acid, a fatty acid an amino acid, an aromatic acid, an alpha or beta hydroxyl acid an organic base or a nitrogen containing compound. In certain cases the API, can also affect pH.

In one or more further embodiments the modulating agent is used to describe an agent, which is a chelating or sequestering or complexing agent that is sufficiently soluble or functional in the solvent to enable it to "mop up" or "lock" metal ions.

In an embodiment modulating agent is used to describe an agent which can effect pH in an aqueous solution the term modulating agent more particularly means an acid or base or buffer system or combinations thereof, which is introduced into or is present in and acts to modulate the ionic or polar characteristics and any acidity or basesity balance of (i) a waterless or low water content or (ii) an emulsion carrier, composition, foamable carrier or foamable composition or resultant foam described herein.

The substance or residue can be introduced into the formulation from any one or more of the ingredients, some of which themselves may have acidic or basic properties. For example the polymer or solvent may contain basic residues in which case it may be desirable or beneficial to add an acid. Alternatively the surfactant may contain some acid residues in which case the addition of a base may be desirable and beneficial. In some cases more than one ingredient may contain residues which may ameliorate or compound their significance. For example, if one ingredient provided weak acid residues and another ingredient provided stronger acid residues, the pH in an emulsion environment should be lower. In contrast, if one residue was acidic and the other basic the net effect in the formulation maybe significantly reduced. In some circumstances the active ingredient may favor an acidic pH or more significantly may need to be maintained at a certain acidic pH otherwise it may readily isomerize, chemically react or breakdown, in which case introducing acidic components such as an acidic polymer might be of help. In an embodiment of the present invention sufficient modulating agent is added to achieve a pH in which the active agent is preferably stable. In another embodiment of the present invention sufficient modulating agent is added to achieve an artificial pH in which the active agent is preferably stable.

The terms pH, pKa, and pKb, buffers and the like are used in classical measurements of an aqueous solution. Such measurements are artificial in a waterless environment. Nevertheless, reference to and description below of such terms are made for convenience and clarity, since such terms are well defined and understood with reference to aqueous solutions and further due to the lack of an appropriate uniform way of describing and identifying the artificial or virtual pH, pK etc in a waterless environment in relation to the present invention. Although predictions of artificial pH can be made using dilution techniques of measurements of waterless formulations diluted in water they are formulation sensitive and specific and have to be carefully calibrated with complex formulas.

Waterless medium can be polar and protic yet it does not conform to classical ionic behavior.

In one or more embodiments of the present invention the modulating agent comprises an organic compound.

In one or more preferred embodiments of the present invention the chelating agent is selected from the group consisting of ethylenediaminetetraacetic acid (EDTA), diethylenetriaminepentaacetic acid (DTPA), hydroxyethylenediaminetriacetic acid (HEDTA), nitrilotriacetic acid (NTA), O,O'-bis(2-aminoethyl)ethyleneglycol-N,N,N',N'-tetraacetic acid (EGTA), trans-1,2-diaminocyclohexane-N,N,N',N'-tetraacetic acid (CyDTA) or a pharmaceutically acceptable salt thereof (normally as a sodium salt), more preferably EDTA, HEDTA and their salts; most preferably EDTA and its salts.

In one or more embodiments of the present invention a preferred non limiting example of the chelating agent is EDTA. Typically, the chelating and sequestering agent is present in the composition at a level of up to about 5.0%, preferably 1.0 percent, by weight, of the composition.

In one or more embodiments of the present invention the modulating agent may also be a preservative or an antioxidant or an ionization agent. Any preservative, antioxidant or ionization agents suitable for pharmaceutical or cosmetic application may be used. Non limiting examples of antioxidants are tocopherol succinate, propyl galate, butylated hydroxy toluene and butyl hydroxy anisol as well as a whole range of flavanoids such as quercitin and rutin. Ionization agents may be positive or may be negative depending on the environment and the active agent or composition that is to be protected. Ionization agents may for example act to protect or reduce sensitivity of active agents. Non limiting examples of positive ionization agents are benzyl conium chloride, and cetyl pyridium chloride. Non limiting examples of negative ionization agents are sodium lauryl sulphate, sodium lauryl lactylate and phospholipids.

Humectant

A humectant is a substance that helps retain moisture and also prevents rapid evaporation. Non limiting examples are propylene glycol, propylene glycol derivatives, glycerin, hydrogenated starch hydrosylate, hydrogenated lanolin, lanolin wax, D manitol, sorbitol, sodium 2-pyrrolidone-5-carboxylate, sodium lactate, sodium PCA, soluble collagen, dibutyl phthalate, and gelatin. Other examples may be found in the Handbook of Pharmaceutical Additives published by Gower. In the present invention the humectant is preferably a hydrophobic humectant.

Moisturizers

A moisturizer, is a substance that helps retain moisture or add back moisture to the skin. Examples are allantoin, petrolatum, urea, lactic acid, sodium PCV, glycerin, shea butter, caprylic/capric/stearic triglyceride, candelilla wax, propylene glycol, lanolin, hydrogenated oils, squalene, sodium hyaluronate and lysine PCA. Other examples may be found in the *Handbook of Pharmaceutical Additives* published by Gower. In the present invention the moisturizer is preferably a hydrophobic moisturizer.

Pharmaceutical compositions may in one or more embodiments usefully comprise in addition a humectant or a moisturizer or combinations thereof.

Polar Solvent

A "polar solvent" is an organic solvent, typically soluble in both water and oil. Certain polar solvents, for example propylene glycol and glycerin, possess the beneficial property of a humectant.

In one or more embodiments, the polar solvent is a humectant.

In one or more embodiments, the polar solvent is a polyol. Polyols are organic substances that contain at least two hydroxy groups in their molecular structure.

In one or more embodiments, the polar solvent contains an diol (a compound that contains two hydroxy groups in its molecular structure), such as propylene glycol (e.g., 1,2-propylene glycol and 1,3-propylene glycol), butaneediol (e.g., 1,4-butaneediol), butaneediol (e.g., 1,3-butaneediol and 1,4-butenediol), butynediol, pentanediol (e.g., 1,5-pentanediol), hexanediol (e.g., 1,6-hexanediol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the polar solvent contains a triol (a compound that contains three hydroxy groups in its molecular structure), such as glycerin and 1,2,6-Hexanetriol.

Other non-limiting examples of polar solvents include pyrrolidones, (such as N-methyl-2-pyrrolidone and 1-methyl-2-pyrrolidinone), dimethyl isosorbide, 1,2,6-hexapetriol, dimethyl sulfoxide (DMSO), ethyl proxitol, dimethylacetamide (DMAc) and alpha hydroxy acids, such as lactic acid and glycolic acid.

According to still other embodiments, the polar solvent is a polyethylene glycol (PEG) or PEG derivative that is liquid at ambient temperature, including PEG200 (MW (molecular weight) about 190-210 kD), PEG300 (MW about 285-315 kD), PEG400 (MW about 380-420 kD), PEG600 (MW about 570-630 kD) and higher MW PEGs such as PEG 4000, PEG 6000 and PEG 10000 and mixtures thereof.

Polar solvents are known to enhance the penetration of active agent into the skin and through the skin, and therefore, their inclusion in the composition can be desirable, despite their undesirable skin drying and irritation potential. There is at one level a commonality between the different polar solvents and their penetration enhancement properties. Lower molecular weight alcohols can sometimes be more potent as a solvent, for example by extracting lipids from the skin layers more effectively, which characteristic can adversely affect the skin structure and cause dryness and irritation. Therefore the selection of lower molecular weight alcohols is ideally avoided.

Potent Solvent

In one or more embodiments, the foamable composition includes a potent solvent, in addition to or in place of one of the hydrophobic solvents, polar solvents or emollients of the composition. A potent solvent is a solvent other than mineral oil that solubilizes a specific active agent substantially better than a hydrocarbon solvent such as mineral oil or petrolatum. For example, a potent solvent solubilizes the active agent 5 fold better than a hydrocarbon solvent; or even solubilizes the active agent 10-fold better than a hydrocarbon solvent.

In one or more embodiments, the composition includes at least one active agent in a therapeutically effective concentration; and at least one potent solvent in a sufficient amount to substantially solubilize the at least one active agent in the composition. The term "substantially soluble" means that at least 95% of the active agent has been solubilized, i.e., 5% or less of the active agent is present in a solid state. In one or more embodiments, the concentration of the at least one potent solvent is more than about 40% of the at least one solvent of the composition; or even more than about 60%.

Non-limiting examples of pairs of active agent and potent solvent include: Betamethasone valerate: Practically insoluble in mineral oil (<0.01%); soluble more than 1% in glycofurol; Hydrocortisone butyrate: Practically insoluble in mineral oil (<0.01%); soluble more than 1% in glycofurol; Metronidazole: Practically insoluble in mineral oil (<0.01%); soluble more than 1% in dimethyl isosrbide; Ketoconazole: Practically insoluble in mineral oil (<0.01%); soluble more than 1% in glycofurol, propylene glycol and dimethyl isosrbide; Mupirocin: Practically insoluble in mineral oil (<0.01%); soluble more than 1% in glycofurol, hexylene glycol, dimethyl isosorbide, propylene glycol and polyethylene glycol 400 (PEG 400); Meloxicam, a nonsteroidal anti-inflammatory agent: Practically insoluble in mineral oil (<0.001%); soluble in propylene glycol: 0.3 mg/mL; and in PEG 400: 3.7 mg/mL; and Progesterone: Practically insoluble in mineral oil (<0.001%); soluble in PEG 400: 15.3 mg/mL.

A non-limiting exemplary list of solvents that can be considered as potent solvents includes polyethylene glycol, propylene glycol, hexylene glycol, butaneediols and isomers thereof, glycerol, benzyl alcohol, DMSO, ethyl oleate, ethyl caprylate, diisopropyl adipate, dimethylacetamide, N-methylpyrrolidone, N-hydroxyethylpyrrolidone, polyvinylpyrrolidone, isosorbide derivatives, such as dimethyl isosorbide, glycofurol and ethoxydiglycol (transcutol) and laurocapram.

In another aspect, the present invention provides a method of designing a stable petrolatum foamable composition by selecting at least one active agent; and identifying a solvent that solubilizes the active agent substantially better than mineral oil or petrolatum, for example, solubilizes the active agent 5-fold better or even 10-fold better than a hydrocarbon solvent such as mineral oil or petrolatum. The method may further include adjusting the type and concentration of surfactant and gelling agent to provide a foamable composition.

In another aspect, the active agent has a degree of solubility in solvent, in petrolatum, in the emulsion or a phase thereof and a potent solvent is used to increase the solubility, in one or both phases, in the interphase or in the foam.

In another aspect, the active agent has a limited degree of solubility in solvent, in petrolatum, in the emulsion or a phase thereof and a potent solvent is used to increase the solubility, in one or both phases, in the interphase or in the foam.

The use of a potent solvent in a foam composition provides an improved method of delivering poorly soluble therapeutic agents to a target area. It is known that low drug solubility results in poor bioavailability, leading to decreased effectiveness of treatment. Foam compositions, for which the solvent includes a potent solvent, increase the levels of the active agent in solution and thus, provide high delivery and improved therapy.

Potent solvents, as defined herein, are usually liquid. Formulations comprising potent solvents and active agents are generally disadvantageous as therapeutics, since their usage involves unwanted dripping and inconvenient method of application; resulting in inadequate dosing. Surprisingly, the foams, which are drip-free, provide a superior vehicle for such active agents, enabling convenient usage and accurate effective dosing.

In one or more embodiments the present invention the foamable pharmaceutical composition may additionally include a potent solvent or a mixture of two or more of the above solvents selected from the group of hydrophobic solvents, silicone oils, emollients, polar solvents and potent solvents in an appropriate proportion as would be appreciated to a person skilled in the art and preferably in relatively small amounts.

Polymeric Agent

In one or more embodiments, the foamable composition contains a polymeric agent. The polymeric agent serves to stabilize the foam composition and to control drug residence in the target organ.

In one or more specific non limiting embodiments, the polymeric agent is ASOS, carboxymethyl cellulose/microcrystalline cellulose, Arlacel 2121, or methocel and xantham gum.

More exemplary polymeric agents are classified below in a non-limiting manner. In certain cases, a given polymer can belong to more than one of the classes provided below.

In one or more embodiments, the composition includes a gelling agent. A gelling agent controls the residence of a therapeutic composition in the target site of treatment by increasing the viscosity of the composition, thereby limiting the rate of its clearance from the site. Many gelling agents are known in the art to possess mucoadhesive properties.

The gelling agent can be a natural gelling agent, a synthetic gelling agent and an inorganic gelling agent. Exemplary gelling agents that can be used in accordance with one or more embodiments include, for example, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, starch, chemically modified starches and the like, semi-synthetic polymeric materials such as cellulose ethers (e.g. hydroxyethyl cellulose, hydroxypropyl cellulose, methyl cellulose, carboxymethyl cellulose, methylhydroxyethylcellulose, methylhydroxypropylcellulose, hydroxypropylmethyl cellulose, hydroxyethylcarboxymethylcellulose, carboxymethylcellulose and carboxymethylhydroxyethylcellulose), guar gum, hydroxypropyl guar gum, soluble starch, cationic celluloses, cationic guars, and the like, and synthetic polymeric materials, such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like. Mixtures of the above compounds are also contemplated.

Further exemplary gelling agents include the acrylic acid/ethyl acrylate copolymers and the carboxyvinyl polymers. Non-limiting examples include Carbopol® 934, Carbopol® 940, Carbopol® 950, Carbopol® 980, Carbopol® 951 and Carbopol® 981. Such agents can function as stabalisers in one or more embodiments and as delivery enhancers in one or more other embodiments.

Yet, in other embodiments, the gelling agent includes inorganic gelling agents, such as silicone dioxide (fumed silica).

Mucoadhesive/bioadhesion has been defined as the attachment of synthetic or biological macromolecules to a biological tissue. Mucoadhesive agents are a class of polymeric biomaterials that exhibit the basic characteristic of a hydrogel, i.e. swell by absorbing water and interacting by means of adhesion with the mucous that covers epithelia. Compositions may contain a mucoadhesive macromolecule or polymer in an amount sufficient to confer or partially to confer bioadhesive properties, although these substances may by their nature, increase the tackiness of a composition so this will be taken into account in preparing compositions. The bioadhesive macromolecule can enhance delivery of biologically active agents on or through the target surface. The mucoadhesive macromolecule may be selected from acidic synthetic polymers, preferably having an acidic group per four repeating or monomeric subunit moieties, such as poly (acrylic)- and/or poly(methacrylic) acid (e.g., Carbopol®, Carbomer®), poly(methylvinyl ether/maleic anhydride) copolymer, and their mixtures and copolymers; acidic synthetically modified natural polymers, such as carboxymethylcellulose (CMC); neutral synthetically modified natural polymers, such as (hydroxypropyl)methylcellulose; basic amine-bearing polymers such as chitosan; acidic polymers obtainable from natural sources, such as alginic acid, hyaluronic acid, pectin, gum tragacanth, and karaya gum; and neutral synthetic polymers, such as polyvinyl alcohol or their mixtures. An additional group of mucoadhesive polymers includes natural and chemically modified cyclodextrin, especially hydroxypropyl-β-cyclodextrin. Such polymers may be present as free acids, bases, or salts, usually in a final concentration of about 0.01% to about 0.5% by weight. Many mucoadhesive agents are known in the art to also possess gelling properties.

In one or more embodiments, the polymeric agent contains a film-forming component, although these substances may also by their nature, increase the tackiness of a composition so this will be taken into account in preparing compositions. The film-forming component may include a water-insoluble alkyl cellulose or hydroxyalkyl cellulose. Exemplary alkyl cellulose or hydroxyalkyl cellulose polymers include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or a cross-linking agent may be used to modify the polymer's characteristics. For example, esters such as dibutyl or diethyl phthalate, amides such as diethyldiphenyl urea, vegetable oils, fatty acids and alcohols such as oleic and myristyl acid may be used in combination with the cellulose derivative.

In one or more embodiments, the polymeric agent includes a phase change polymer, which alters the composition behavior from fluid-like prior to administration to solid-like upon contact with the target mucosal surface. Such phase change results from external stimuli, such as changes in temperature or pH and exposure to specific ions (e.g., $Ca^{2+}$). Non-limiting examples of phase change polymers include poly(N-isopropylamide) and Poloxamer 407®.

The polymeric agent is present in an amount in the range of about 0.01% to about 5.0% by weight of the foam composition. In one or more embodiments, it is typically less than about 1 wt % of the foamable composition.

Preferably, a therapeutically effective foam adjuvant is included in the foamable compositions to increase the foaming capacity of surfactants and/or to stabilize the foam. In one or more embodiments, the foam adjuvant agent includes fatty alcohols having 15 or more carbons in their carbon chain, such as cetyl alcohol and stearyl alcohol (or mixtures thereof). Other examples of fatty alcohols are myristyl alcohol (C14), arachidyl alcohol (C20), behenyl alcohol (C22), 1-triacontanol (C30), as well as alcohols with longer carbon chains (up to C50). Fatty alcohols, derived from beeswax and including a mixture of alcohols, a majority of which has at least 20 carbon atoms in their carbon chain, are especially well suited as foam adjuvant agents. The amount of the fatty alcohol required to support the foam system is inversely related to the length of its carbon chains. Foam adjuvants, as defined herein are also useful in facilitating improved spreadability and absorption of the composition.

In one or more embodiments, the foam adjuvant agent includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

In one or more embodiments, a combination of a fatty acid and a fatty ester is employed.

Optionally, the carbon atom chain of the fatty alcohol or the fatty acid may have a double bond. A further class of foam adjuvant agent includes a branched fatty alcohol or fatty acid. The carbon chain of the fatty acid or fatty alcohol also can be substituted with a hydroxyl group, such as 12-hydroxy stearic acid.

A property of the fatty alcohols and fatty acids used in context of the composition is related to their therapeutic properties per se. Long chain saturated and mono unsaturated fatty alcohols, e.g., stearyl alcohol, erucyl alcohol, arachidyl alcohol and behenyl alcohol (docosanol) have been reported to possess antiviral, antiinfective, antiproliferative and anti-inflammatory properties (see, U.S. Pat. No. 4,874,794). Longer chain fatty alcohols, e.g., tetracosanol, hexacosanol, heptacosanol, octacosanol, triacontanol, etc., are also known for their metabolism modifying properties and tissue energizing properties. Long chain fatty acids have also been reported to possess anti-infective characteristics.

In one or more embodiments, the active agent is encapsulated in particles, microparticles, nanoparticles, microcapsules, spheres, microspheres, nanocapsules, nanospheres, liposomes, niosomes, polymer matrix, nanocrystals or microsponges.

The composition may further optionally include a variety of formulation excipients, which are added in order to fine-tune the consistency of the formulation, protect the formulation components from degradation and oxidation and modify their consistency. Such excipients may be selected, for example, from stabilizing agents, antioxidants, humectants, moisturizers, preservatives, colorant and odorant agents and other formulation components, used in the art of formulation.

Propellants

Aerosol propellants are used to generate and administer the foamable composition as a foam. The total composition including propellant, foamable compositions and optional ingredients is referred to as the foamable carrier. The propellant makes up about 3% to about 25% (w/w) of the foamable carrier or composition. Examples of suitable propellants include volatile hydrocarbons such as butane, propane, isobutane, and fluorocarbon gases or mixtures thereof. In an embodiment the propellant is 1681, which is a mixture of three gas propellants propane, isobutene and butane. In another embodiment it is AP 70, which is a mixture of propane, isobutene and butane with a higher pressure. In some circumstances the propellant may be up to 35%. The total composition including propellant, foamable compositions and optional ingredients is referred to as the foamable composition. However, for the purposes of calculating the percentage of each component and thereby the amount present in the resultant foam the propellant is not included in the 100% but is instead added to the 100% since the propellant is essentially discharged into the atmosphere upon expulsion of the formulation.

Non-Flammable Stable Foam Compositions

Alcohol and organic solvents render foams inflammable. It has been surprisingly discovered that fluorohydrocarbon propellants, other than chloro-fluoro carbons (CMCs), which are non-ozone-depleting propellants, are particularly useful in the production of a non-flammable foamable composition. A test according to European Standard prEN 14851, titled "Aerosol containers—Aerosol foam flammability test" revealed that compositions containing an organic carrier that contains a hydrophobic organic carrier and/or a polar solvent, which are detected as inflammable when a hydrocarbon propellant is used, become non-flammable, while the propellant is an HFC propellant.

Such propellants include, but are not limited to, hydrofluorocarbon (HFC) propellants, which contain no chlorine atoms, and as such, fall completely outside concerns about stratospheric ozone destruction by chlorofluorocarbons or other chlorinated hydrocarbons. Exemplary non-flammable propellants according to this aspect include propellants made by DuPont under the registered trademark Dymel, such as 1,1,1,2 tetrafluorethane (Dymel 134), and 1,1,1,2,3,3,3 heptafluoropropane (Dymel 227). HFCs possess Ozone Depletion Potential of 0.00 and thus, they are allowed for use as propellant in aerosol products.

Notably, the stability of foamable emulsions including HFC as the propellant can be improved in comparison with the same composition made with a hydrocarbon propellant.

In one or more embodiments foamable compositions comprise a combination of a HFC and a hydrocarbon propellant such as n-butane or mixtures of hydrocarbon propellants such as propane, isobutane and butane.

Additional Components

In an embodiment, a composition includes one or more additional components. Such additional components include but are not limited to anti perspirants, anti-static agents, buffering agents, bulking agents, conservational agents, chelating agents, cleansers, colorants, conditioners, deodorants, diluents, dyes, emollients, fragrances, hair conditioners, humectants, pearlescent aids, perfuming agents, permeation enhancers, pH-adjusting agents, preservatives, protectants, skin penetration enhancers, softeners, solubilizers, sunscreens, sun blocking agents, sunless tanning agents, viscosity modifiers, ionization agents, and antioxidants like flavonoids and phenolics. As is known to one skilled in the art, in some instances a specific additional component may have more than one activity, function or effect.

In an embodiment, the additional component is a pH adjusting agent or a buffering agent. Suitable buffering agents include but are not limited to acetic acid, adipic acid, calcium hydroxide, citric acid, glycine, hydrochloric acid, lactic acid, magnesium aluminometasilicates, phosphoric acid, sodium carbonate, sodium citrate, sodium hydroxide, sorbic acid, succinic acid, tartaric acid, and derivatives, salts and mixtures thereof.

Sodium Metabisulfite (Disodium Metabisulfite) and Derivatives

Sodium metabisulfite is used as an antioxidant in (primarily acidic) pharmaceutical formulations, at concentrations of 0.01-1.0% w/v., preparations and can also be used as a preservative having some antimicrobial activity at though for alkaline preparations, sodium sulfite is usually preferred Active Agents It is to be understood that the active agents useful herein can in some instances provide more than one benefit or operate via more than one mode of action. Therefore, classifications herein are made for the sake of convenience and are not intended to limit the active agent to that particular application or applications listed.

The composition comprises an active agent that provides therapeutic or cosmetic activity.

Non-limiting examples of active agents include an anti-infective, an antibiotic, an antibacterial agent, an antifungal agent, an antiviral agent, an antiparasitic agent, a steroidal anti-inflammatory agent, a nonsteroidal anti-inflammatory agent, an immunosuppressive agent, an immunomodulator, an immunoregulating agent, a hormonal agent, a steroid, a vasoactive agent, a vasoconstrictor, a vasodilator, vitamin A, a vitamin A derivative, a retinoid, vitamin B, a vitamin B derivative, vitamin C, a vitamin C derivative, vitamin D, a vitamin D derivative, vitamin E, a vitamin E derivative, alpha-tocopheryl polyethylene glycol succinate, vitamin F, a vitamin F derivative, vitamin K, a vitamin K derivative, a wound healing agent, a burn healing agent, a disinfectant, an anesthetic, an antiallergic agent, an alpha hydroxyl acid, lactic acid, glycolic acid, a beta-hydroxy acid, a protein, a peptide, a neuropeptide, an allergen, an immunogenic substance, a haptene, an oxidizing agent, an antioxidant, a dicarboxylic acid, azelaic acid, sebacic acid, adipic acid, fumaric acid, an insecticide, an antiproliferative agent, an anticancer agent, a photodynamic therapy agent, an anti-wrinkle agent, a radical scavenger, a metal oxide (e.g., titanium dioxide, zinc oxide, zirconium oxide, iron oxide), silicone oxide, talc, an anti-acne agent, a skin whitening agent, a self tanning agent, an anti-cellulite agent, a skin protective agent, a masking agent, an anti-wart agent, a refatting agent, a lubricating agent and mixtures thereof at any proportion. The concentration of the active agent can be adapted to exert a therapeutic effect on a disease when applied to an afflicted area.

In one or more embodiments the active agent may be vitamin D or a derivative such as calcipotriol or calcitriol. In one or more other embodiments the vitamin D or derivative is used in combination with a steroid. Due to the different environmental requirements of the two types of API's it is very difficult to produce formulations that are both chemically and physically stable. In certain embodiments there are provided chemically and physically stable formulations containing one or both active agents. Nevertheless, in certain other preferred embodiments the active agents are in separate formulations and are delivered by means of a multichamber or dual chamber device. Alternatively they can be expelled manually simultaneously or consecutively from two separate canisters directed to the same target site.

In one or more embodiments the active agent may be an extract or tincture of one or more beneficial agents that have beneficial properties, for example, when applied to the skin, a body surface, a body cavity or a mucosal surface. The extract can be, for example, alcoholic, hydroalcoholic, propelyne glycol, glycerine, dry, press, cold, hot, liquid carbon dioxide, oil or other process known in the art. The extract or tincture may comprise of substances of animal, plant, (such as herb, fruit, vegetable) mineral or other origin. Nonlimiting examples are proteins, polypepeptides, sugars, hyularonic acid, and coal tar. Herbal extracts may be from any known therapeutic herb, as listed for example in Herbal Medicines, London: Pharmaceutical Press Electronic Version 2006 or in the American Herbal Association electronic publication Herbal gram or in German Commission E., such as, angelica, calendula, celery, coltsfoot, comfrey, dandelion, jamaica dogwood, kava, marshmallow, prickly ash, northern prickly ash, southern senna, valerian, agrimony, aloe vera, alfalfa, artichoke, avens, bayberry, bloodroot, blue flag, bogbean, boldo, boneset, broom, buchu, burdock, burnet, calamus, calendula, cascara, centaury, cereus, chamomile, german chamomile, roman chamomile, cinnamon, divers, cohosh, black, cohosh, blue, cola, corn silk, couchgrass, cowslip, damiana, devil's claw, drosera, echinacea, elder, elecampane, euphorbia, eyebright, figwort, frangula, fucus, fumitory, garlic, golden seal, gravel root, ground ivy, guaiacum, hawthorn, holy thistle, hops, horehound black, horehound white, horse chestnut hydrangea, ispaghula, juniper, lady's lipper, liferoot, lime flower, liquorice, lobelia, maté, meadowsweet, mistletoe, motherwort, myrrh, nettle, parsley, parsley piert, passionflower, pennyroyal, pilewort, plantain, pleurisy root, pokeroot, poplar, pulsatilla, queen's delight, raspberry, red clover, rosemary, sage, sarsaparilla, sassafras, scullcap, senega, shepherd's purse, skunk cabbage, slippery elm, squill, St. John's wort, stone root, tansy, thyme, uva-ursi, vervain, wild carrot, wild lettuce, willow, witch hazel, yarrow and yellow dock. The extract may contain, for example, an aqueous, polar, hydrophobic or potent solvent as will be appreciated by a person of ordinary skill in the art.

In one or more embodiments, the active agent is an anti-infective agent, selected from an antibiotic agent, an antibacterial agent, an anti-fungal agent, an anti-viral agent and an anti-parasite agent.

The antibacterial drug can be active against gram positive and gram-negative bacteria, protozoa, aerobic bacteria and anaerobic ones.

In one or more embodiments, the antibiotic agent is selected from the classes consisting of beta-lactam antibiotics, synthetic and semi-synthetic penicillin's, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, fluoroquinolnes, antibiotic steroids, cyclosporines, sulfonamides, tetracycline, chloramphenicol, dicarboxylic acids, such as azelaic acid, salicylates, antibiotic metals, oxidizing agents, substances that release free radicals and/or active oxygen, cationic antimicrobial agents, quaternary ammonium compounds, biguanides, triguanides, bisbiguanides and analogs and polymers thereof and naturally occurring antibiotic compounds.

Additional antibacterial agents, which are non-specific, include strong oxidants and free radical liberating compounds, such as hydrogen peroxide, bleaching agents (e.g., sodium, calcium or magnesium hypochloride and the like), iodine, chlorohexidine and benzoyl peroxide.

The antifungal agent can be an azole compound. Exemplary azole compounds include azoles selected from the group consisting of azoles, diazoles, triazoles, miconazole, ketoconazole, clotrimazole, econazole, mebendazole, bifonazole, butoconazole, fenticonazole, isoconazole, oxiconazole, sertaconazole, sulconazole, thiabendazole, tiaconazole, fluconazole, itraconazole, ravuconazole and posaconazole.

Additional exemplary antifungal agents include griseoulvin, ciclopirox, amorolfine, terbinafine, Amphotericin B, potassium iodide, flucytosine (5FC) and any combination thereof at a therapeutically effective concentration.

In one or more embodiments, the active agent is an antiviral agent. Any known antiviral agent, in a therapeutically effective concentration, can be incorporated in the foam composition. Exemplary antiviral agents include, but not limited to, acyclovir, famciclovir, gancyclovir, valganciclovir and abacavir.

In another embodiment according to the present invention, the active agent is an anti-inflammatory or anti-allergic agent. Anti-inflammatory agents can be selected from the group of corticosteroids, non-steroidal anti-inflammatory drugs (NSAIDs), anti-histamines, immunosuppressant agents, immunomodulators; and any combination thereof at a therapeutically effective concentration.

Non-limiting examples of corticosteroids include hydrocortisone, hydrocortisone acetate, desonide, betamethasone valerate, clobetasone-17-butyrate, flucinonide, fluocinolone acetonide, alcometasone dipropionate, mometasone furoate, prednicarbate, triamcinolone acetonide, betamethasone-17-benzoate, methylprednisolone aceponate, betamethasone dipropionate, halcinonide, triamcinolone acetonide, halobetasol and clobetasol-17-propionate.

A second class of anti-inflammatory agents, which is useful in the foam, includes the nonsteroidal anti-inflammatory agents (NSAIDs). The variety of compounds encompassed by this group is well known to those skilled in the art. Specific non-steroidal anti-inflammatory agents useful in the composition invention include, but are not limited to, oxicams, such as piroxicam, isoxicam, tenoxicam, sudoxicam; salicylates, such as salicylic acid, ethyl salicylate, methyl salyicilate, aspirin, disalcid, benorylate, trilisate, safapryn, solprin, diflunisal, and fendosal; scetic acid derivatives, such as diclofenac, fenclofenac, indomethacin, sulindac, tolmetin, isoxepac, furofenac, tiopinac, zidometacin, acemetacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and pyrazoles, such as phenylbutazone, oxyphenbutazone, feprazone, azapropazone, and trimethazone.

Any further steroidal and nonsteroidal compounds, having the capacity to prevent, alleviate the symptoms of, treat or cure inflammation processes, are generally included, as possible anti-inflammatory agents, according to the present invention.

Antiallergic active agents include antihistamine compounds, including, in a non limiting manner, thylenediamines, such as pyrilamine (mepyramine), antazoline and methapyrilene; tripelennamine phenothiazines, such as promethazine, methdilazine and trimeprazine; ethanolamines, such as diphenhydramine, bromodiphenhydramine, carbinoxamine, clemastine, dimenhydrinate, diphenylpyraline, doxylamine and phenyltoxamine; piperazines, such as cyclizine, buclizine, chlorcyclizine, hydroxyzine, meclizine and thiethylperazine; alkylamines, such as brompheniramine, pyrrobutamin, desbrompheniramine, tripolidine, dexchlorpherniramine, chlorpheniramine; dimethindene and pheniramine; and piperidines, such as cyproheptadine and azatadine. These active agents, as well as additional antihistamines can also be incorporated in the composition.

The composition may also comprise an anti-inflammatory or antiallergic agent, wherein said agent reduces the occurrence of pro-inflammatory cytokines or inhibits the effect of pro-inflammatory cytokines.

Immunosuppressant agents, immunoregulating agents and immunomodulators are chemically or biologically derived agents that modify the immune response or the functioning of the immune system (as by the stimulation of antibody formation or the inhibition of white blood cell activity). Immunosuppressant agents and immunomodulators include, among other options, cyclic peptides, such as cyclosporine, tacrolimus, tresperimus, pimecrolimus, sirolimus (rapamycin), verolimus, laflunimus, laquinimod and imiquimod.

In one or more embodiments, the active agent is a topical anesthetic. Examples of topical anesthetic drugs include, but not limited to, benzocaine, lidocaine, bupivacaine, chlorprocaine, dibucaine, etidocaine, mepivacaine, tetracaine, dyclonine, hexylcaine, procaine, cocaine, ketamine, pramoxine, and phenol. Mixtures of such anesthetic agents may be synergistically beneficial.

In one or more embodiments, the active agent is a "keratolytically active agent." The term "keratolytically active agent" refers herein to a compound, which loosens and removes the stratum corneum of the skin, or alters the structure of the keratin layers of the skin.

Suitable keratolytically active agents include phenol and substituted phenolic compounds. Such compounds are known to dissolve and loosen the intracellular matrix of the hyperkeratinized tissue. Dihydroxy benzene and derivatives thereof have been recognized as potent keratolytic agents. Resorcinol (m-dihydroxybenzene) and derivatives thereof are used in anti-acne preparations. Hydroquinone (p-dihydroxybenzene), besides its anti-pigmentation properties, is also keratolytic.

Vitamin A and its derivatives, such as retinoic acid, isoretinoic acid, retinol and retinal are another preferred class of keratolytically active agents.

Another group of keratolytically active agents include alpha-hydroxy acids, such as lactic acid and glycolic acid and their respective salts and derivatives; and beta-hydroxy acids, such as Salicylic acid (o-hydroxybenzoic acid) and its salts and pharmaceutically acceptable derivatives, which typically possess anti-inflammatory, as well as keratolytic, activity. Yet, another class of preferred keratolytically active agents includes urea and its derivatives.

In one or more embodiments, the active agent is a retinoid. Retinoids include, for example, retinol, retinal, all-trans retinoic acid and derivatives, isomers and analogs thereof. Etretinate, actiretin, isotretinoin, adapalene and tazarotene are further examples of said retinoid isomers and analogs.

In one or more embodiments, the active agent is a vitamin $D_3$ analogue such as calcipotriol, tacalcitol, maxacalcitol, and calcitriol with calcipotriol being especially preferred. Vitamin $D_3$ analogues and derivatives are known to degrade at low pH levels. The waterless compositions can protect against or retard such degredation. In certain embodiments where the active agent is vitamin $D_3$ or an analogue or a derivative thereof, and there is a concern that there are some potential residues which could effect the agent in the composition or following application to the skin or a body cavity could cause breakdown a neutralizing or stabilizing agent might additionally be added which could be a suitable pH adjuster or buffer. Note where calcipotriol and a steroid like betmethasone diprionate are in the same composition the waterless compositions are ideal to protect from degradation. In an aqueous environment they have opposing pH requirements for stability with the steroid favoring an acidic environment and the vitamin favoring a basic environment.

In one or more embodiments, the active agent is an insecticide or an insect repellent agent.

In one or more embodiments, the active agent is an anti cancer agent.

In one or more embodiments, the active agent is a photodynamic therapy (PDT) agent. By way of example, such PDT agents can be modified porphyrins, chlorins, bacteriochlorins, phthalocyanines, naphthalocyanines, pheophorbides, purpurins, m-THPC, mono-L-aspartyl chlorin e6, bacteriochlorins, phthalocyanines, benzoporphyrin derivatives, as well as photosensitizer precursors, such as aminolevulinic acid (ALA).

In one or more embodiments, the active agent is an agent useful in the treatment of burns, wounds, cuts and ulcers. The foam compositions may comprise a combination of anti-infective agents (against bacteria, fungi and/or viruses), anti-inflammatory agents (steroidal and/or NSAIDs) and pain relieving components.

In one or more embodiments, the active agent can also be used as an absorption and bioavailability enhancer for other drugs and vitamins, for example TPGS that forms its own micelles can aid e.g. amprenavir and vitamin D respectively.

In one or more embodiments the active agent has some degree of solubility in water. By the phrase some degree of solubility it is understood to include API's that are described by the US or European Pharmacopoeia as being slightly soluble, sparingly soluble, soluble, freely soluble or very soluble. Both describe the approximate ranges of parts of solvent (volume) required for 1 part (per gram) of solute as less than 1 for very soluble; from 1-10; for freely soluble, from 10-30 for soluble; from 30 to 100 for sparingly soluble; and from 100 to 1000 for slightly soluble. Additionally, the phrase may include the terms partly soluble and miscible. Non limiting examples of substances that have some degree of solubility in water are acyclovir, azelaic acid, allantoin, ammonium lactate, benzoyl peroxide, caffeine, calcipotriol, ciclopirox olamine, clindamycin hydrochloride, clindamycin phosphate, clindamycin palmitate hydrochloride, coal tar, cyanocobalamine, diclofenac sodium, gentamycin sulphate, lactic acid, glycyrrhizinic acid, map (magnesium ascorbyl phosphate), minoxidil, mupirocin, salicylic acid, terbinafine, urea, fusidic acid, a hydrocortisone, hydrocortisone sodium phosphate, hydrocortisone sodium succinate, a clobetasol, a halobetasol, a batamethsone; halobetasol and clobetasol-17-propionate or -17-butyrate; ketoconazole, lidocaine hydrochloride, metronidazole, tetracycline, tetracycline hydrochloride, meclocycline sulfosalicylate, resorcinol, chloramphenicol, erythromycin, acriflavinium monochloride, ethacridine lactate, dibrompropamidine isetionate, chlorhexidine acetate, chlorhexidine gluconate, chlorhexidine hydrochloride, hexamidine isetionate, phenol, povidone-iodine, dequalinium chloride, hydroxyquinoline sulfate, potassium hydroxyquinoline sulphate, benzalkonium chloride, cetrimonium bromide, cetylpyridinium chloride, cetrimide, phenylmercuric acetate, phenylmercuric borate, mercuric chloride, silver nitrate, potassium permanganate, tosylchloramide sodium, prednisolone sodium phosphate, betamethasone sodium phosphate, demeclocycline, demeclocycline hydrochloride, chlortetracycline hydrochloride, oxytetracycline hydrochloride, neomycin sulfate, bacitracin zinc, gentamicin sulphate, amikacin, amikacin sulphate, sulfathiazole sodium, mafenide acetate, idoxuridine, fumaric acid, mepyramine maleate, tripelennamine hydrochloride, promethazine hydrochloride, dimetindene maleate, diphenhydramine hydrochloride, cinchocaine hydrochloride, oxybuprocaine hydrochloride, benzocaine, tetracaine hydrochloride, pramoxine hydrochloride, panthenol, dexpanthenol, calcium pantothenate, hyaluronic acid, trypsin, aminobenzoic acid, methylrosanilinium chloride, sodium butyl hydroxybenzoate, sodium ethyl hydroxybenzoate, sodium methyl hydroxybenzoate, sodium propyl hydroxybenzoate, flucytosine and fluconazole.

In one or more embodiments the active agent has a limited degree of solubility in water. By a limited degree of solubility it is understood to include API's that are described by the US or European Pharmacopoeia as being very slightly soluble. The approximate range of parts of solvent (volume) required for 1 part (per gram) of solute is from 1000 to 10000 for very slightly soluble.

In one or more embodiments the active agent has some degree of solubility in an petrolatum emollient. So any agent that by its nature is hydrophobic may qualify, such as permethrin and tetracaine.

In one or more embodiments the active agent has some degree of solubility in a composition in one or more of the water phase, the oil phase, or the interphase or the foam. For example, beamethasone valerate has been stated to be practically insoluble in water. However, it has been surprisingly found that it is soluble in the water phase of a foamable composition in a pharmaceutically effective amount for topical application.

The foam compositions, with or without further active ingredients, are suitable for the further application as "cosmeceutical" preparation (cosmetic products with therapeutic benefit), to treat "cosmetic" skin disorders, such as aging skin, wrinkles, hyperpigmentation (melasma, chloasma, freckles, etc.), scaly skin and other skin undesirable properties.

Any cosmetically active agent is considered an active agent in the context. The *CTFA Cosmetic Ingredient Handbook* describes a wide variety of non-limiting cosmetic and pharmaceutical ingredients commonly used in the skin care industry, which are suitable for use in the compositions. Examples of these ingredient classes include: abrasives, absorbents, aesthetic components such as fragrances, pigments, colorings/colorants, essential oils, astringents, etc. (e.g., clove oil, menthol, camphor, eucalyptus oil, eugenol, menthyl lactate, witch hazel distillate), anti-acne agents, anti-caking agents, antifoaming agents, anti-microbial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, moisturizers, etc.), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, and vitamins and derivatives thereof.

In one or more embodiments, the active agent is an agent useful in the treatment of acne, wrinkles and scars. Examples of useful anti-acne actives include resorcinol, sulfur, salicylic acid and salicylates, alpha-hydroxy acids, nonsteroidal anti-inflammatory agents, benzoyl peroxide, retinoic acid, isoretinoic acid and other retinoid compounds, adapalene, tazarotene, azelaic acid and azelaic acid derivatives, antibiotic agents, such as erythromycin and clyndamycin, zinc salts and complexes, and combinations thereof, in a therapeutically effective concentration. Exemplary anti-wrinkle/anti-atrophy active agents suitable for use in the compositions include sulfur-containing D and L amino acids and their derivatives and salts, particularly the N-acetyl derivatives; thiols; hydroxy acids (e.g., alpha-hydroxy acids such as lactic acid and glycolic acid and their derivatives and salts; or beta-hydroxy acids such as salicylic acid and salicylic acid salts and derivatives), urea, hyaluronic acid, phytic acid, lipoic acid; lysophosphatidic acid, skin peel agents (e.g., phenol, resorcinol and the like), vitamin B3 compounds (e.g., niacinamide, nicotinic acid and nicotinic acid salts and esters, including non-vasodilating esters of nicotinic acid (such as tocopheryl nicotinate), nicotinyl amino acids, nicotinyl alcohol esters of carboxylic acids, nicotinic acid N-oxide and niacinamide N-oxide), vitamin B5 and retinoids (e.g., retinol, retinal, retinoic acid, retinyl acetate, retinyl palmitate, retinyl ascorbate). In the case of dry, scaly skin (xerosis) and ichthyosis such agents can alleviate the symptoms by temporary relief of itching associated with these conditions.

In one or more embodiments, the active agent is an anti-oxidant or a radical scavenger. Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid, gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lysine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used.

It is further pointed out that polyunsaturated fatty acids, containing omega-3 and omega-6 fatty acids (e.g., linoleic and linolenic acid, gamma-linoleic acid (GLA), eicosapentaenoic acid (EPA) and docosahexaenoic acid (DHA)) are beneficial in the treatment of psoriasis and other skin inflammation conditions. Likewise, emollients and silicone oils exert moisture-retaining and skin protective effects on the skin. Thus, in a preferred embodiment, a skin protective foam is provided, wherein the hydrophobic carrier comprises in full or in part, an organic liquid selected from the group consisting of emollients, silicone oil and oils rich in unsaturated fatty acids.

In one or more embodiments, the active agent is a self-tanning active Agent, such as dihydroxyacetone.

According to another embodiment, the active agent comprises solid matter or particulate matter, i.e., material that is not soluble in the liquid carrier composition of the foamable composition. For definition purposes, solid matter shall mean material that is not soluble in the foamable composition more than 10% of the concentration intended to be included in said foamable composition. By way of example, the following classes of solid matter substances are presented: metallic oxides, such as titanium dioxide, zinc oxide, zirconium oxide, iron oxide; silicon containing materials such as silicone oxide and talc; carbon, for example in the form of amorphous carbon or graphite; insoluble oxidizing agents, such as benzoyl peroxide, calcium and magnesium hypochlorite; metallic Silver; cosmetic scrub materials, including, for example meals of strawberry seeds, raspberry seeds, apricot seeds, sweet almond, cranberry seeds; and pigments.

In an embodiment the solid is substantially uniformly dispersed as a suspension in the composition, wherein the composition is formulated so that the resultant foam when applied topically to a target will form an effective barrier and the composition does not comprise a non propellant organic cosolvent.

According to certain embodiments, the active agent is selected from the group of solvent, surface active agent, foam adjuvant and gelling agent, which are, on a case-by-case basis, known to possess a therapeutic benefit.

In one or more embodiments at least one or at least two active agents are included in the composition.

Whenever there is reference to an active agent and or derivatives the reference includes, derivatives, conjugates, analogues, prodrugs, chelates, complexes, ions, isomers, enantimers, and salts thereof.

Composition and Foam Physical Characteristics and Advantages

A pharmaceutical or cosmetic composition manufactured using the foamable carrier is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foamable composition can be in the state of (1) solutions; (2) a readily dispersible suspension; or (3) an emulsion. It is stable, having an acceptable shelf life of a year, or at least two years at ambient temperature, as revealed in accelerated stability tests. Polar solvents, hydrophobic carriers and propellants, which are a mixture of low molecular weight hydrocarbons, tend to impair the stability of emulsions and to interfere with the formation of a stable foam upon release from a pressurized container. It has been observed, however, that the foamable compositions according to the present invention are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam. Compositions containing semi-solid hydrophobic solvents, e.g., white petrolatum, as the main ingredients of the oil phase of the emulsion, exhibit high viscosity and reduced or poor flowability and are not ideal candidates for a foamable composition. It has been found that despite the aforesaid in the compositions s the produce foams, which are surprisingly soft, or with improved stability.

Where the petrolatum emollient is provided in large quantities sufficient to produce an effective occlusion the foam can act as a barrier to water soluble irritants and air borne bacteria whilst also providing a vehicle for water soluble active agents. However, there is a potential downside of anaerobic bacteria growing under the barrier. Depending on the nature of the emulsion formulation an petrolatum emollient can aid API transport through the skin or retard penetration prolonging thereby its action. Accordingly a pharmaceutical formulation for example with petrolatum can be designed to improve or prolong delivery as is required as will be appreciated by a person skilled in the art.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal. Achieving G or E, where petrolatum a heavy, greasy, tacky substance, is the main or major component is a challenge and achievement. As a consequence of the high levels of petrolatum and its nature, the density of the resultant foams can be significantly higher than with non or low petrolatum foams. With high petrolatum a density of the order of about 0.5 g to about 0.4 g is acceptable. Nevertheless, in certain other embodiments relatively low density petrolatum foams can be achieved having a density below about 0.4 g and preferably with a density of less than about 0.2 g.

A further aspect of the foam is breakability. The breakable foam is thermally stable, yet breaks under shear force. Shear-force breakability of the foam is clearly advantageous over thermally induced breakability. Thermally sensitive foams immediately collapse upon exposure to skin temperature and, therefore, cannot be applied on the hand and afterwards delivered to the afflicted area.

In one or more embodiments there is provided a composition, wherein the foam demonstrates at least eighteen of the following properties:

a) a foam quality of 5-6;
b) a color of white to off-white; or a yellowish color:
c) no odor or faint odor; or substantially masked odor;
d) a foam quality of 5-6 after one freeze-thaw cycle;
e) a foam quality of 5-6 after two freeze-thaw cycles;
f) a foam quality of 5-6 after three freeze-thaw cycles;
g) a foam quality of 5-6 after four freeze-thaw cycles;
h) a foam quality of 5-6 after about 3 weeks' storage at 30° C.;
i) a foam quality of 5-6 after about 3 weeks' storage at 40° C.;
j) a foam quality of 5-6 after about 3 months' storage at 30° C.;
k) a foam quality of 5-6 after about 3 months' storage at 40° C.;
l) a collapse time of more than 50 seconds;
m) a collapse time of more than 120 seconds; and
n) a collapse time of more than 180 seconds;
o) a collapse time of more than 300 seconds;
p) a foam hardness in the range of about 5 g to about 100 g;
q) a foam hardness in the range of about 15 g to about 55 g;
r) a foam hardness in the range of about 30 g to about 85 g;
s) a density of less than 0.5 g;
t) a density of less than 0.3 g;
u) a density of less than 0.2 g;
v) a foam corneometer value of at least 50 after washing a formulation applied to the skin; and
w) an average focus group score of 60 or more.

In a preferred embodiment it demonstrates one or more of the following: nineteen; twenty; twenty one; twenty two properties and in a more preferred embodiment it demonstrates all of the properties.

In one or more embodiments there is provided a composition, wherein the foam provides at least two of the following traits:

a) increased solubility of the active agent;
b) increased delivery of the active agent;

c) the composition provides enhanced skin barrier build up;
d) the composition provides increased penetration of the active agent whilst replenishing the skin;
e) the composition prolongs the delivery of the active agent whilst replenishing the skin.

In one or more embodiments there is provided a composition, wherein the foam provides at least two of the following traits:
a) the composition is able to at least partially solubilize the active agent;
b) the composition is able to substantially solubilize the active agent. c) the active agent is at least partially soluble in petrolatum or mixtures thereof;
d) the active agent is at least partially soluble in a solvent substantially miscible in petrolatum or mixtures thereof
e) the active agent is at least partially soluble in a hydrophilic solvent;
f) the active agent is at least partially soluble in an oil. the active agent is at least partially soluble in a PPG alkyl eth the active agent is insoluble or slightly soluble and is distributed uniformly in the composition.

Dual Chamber

Dual and Multi Chamber devices and heads suitable for use with the formulations described herein where a first formulation is stored in a first canister and a second formulation is stored in a second canister are described in U.S. Pat. No. 6,305,578 entitled DEVICE FOR MIXING, FOAMING AND DISPENSING LIQUIDS FROM SEPARATE COMPRESSED-GAS CONTAINERS and in US Publication 2007-0069046 and entitled APPARATUS AND METHOD FOR RELEASING A MEASURE OF CONTENT FROM A PLUARITY OF CONTAINERS all of which are incorporated herein by reference in their entirety. More particularly any of the devices and uses described are applicable herein and are incorporated by reference.

In an embodiment the dual chamber device is as described in U.S. Pat. No. 6,305,578 for example,
a compressed gas container apparatus, having
  at least two compressed gas containers, disposed side by side, each for one foamable liquid product which contains a liquefied propellant gas, wherein
  both compressed gas containers are each provided with a valve,
  both valves are actuatable in common by a top fitting, and each valve is provided through the top fitting with a connecting conduit,
  the connecting conduits discharge into a mixing chamber, and
  an expansion conduit adjoins the mixing chamber and on its end has a foam dispensing opening, characterized in that
  the connecting conduits and the mixing chamber have such small cross-sectional areas that when a product is dispensed, the products flowing through the connecting conduits) and the mixing chamber remain in a liquid phase.

In an embodiment the dual dispenser head is as described in US Publication 2007-0069046 for example:
a dispenser head for use with a plurality of containers, comprising:
  (a) an actuator, wherein the dispensing head is structured and positioned to be an actuator or comprises an actuator button disposed within the dispensing head to simultaneously actuate the plurality of containers
  (b) a flow guide comprising
    (A) a plurality of flow conduits disposed within the flow guide; and
    (B) for each of the plurality of flow conduits,
      (ii) an inlet through a wall of the flow guide connecting with a flow conduit; and
      (iii) an outlet from a flow conduit through a wall of the flow guide;
    (C) and for each of the plurality of inlets and containers, a linker, each to link an inlet and a container to allow the contents of the container upon actuation to pass through the inlet and through the flow conduit to reach and pass through the outlet;
    (D) and wherein the flow guide is structured and positioned to allow simultaneous flow communication between each of the plurality of flow conduits and wherein the plurality of outlets are structured and positioned to allow substantially contemporaneously dispensing and/or combining of the content from a plurality of containers external to the dispensing head.

In one or more embodiments there is provided a kit comprising a dual chamber device or dual dispenser head, a first canister comprising a first foamable formulation comprising a first API and a second canister comprising a second foamable formulation comprising a second API wherein each canister is connectable to the said device or head. The first foamable formulation may be any of the stable petrolatum formulations described herein and the second foamable formulation may also be any of the stable petrolatum formulations described herein. In an embodiment the first API is a steroid and the second API is a vitamin D derivative and the each formulation is adapted to carry an effective amount of steroid and vitamin D derivative, respectively, such that each formulation and API is sufficiently chemically and physically stable for pharmaceutical use.

Other foamable compositions are described in: U.S. Publication No. 05-0232869, published on Oct. 20, 2005, entitled NONSTEROIDAL IMMUNOMODULATING KIT AND COMPOSITION AND USES THEREOF; U.S. Publication No. 05-0205086, published on Sep. 22, 2005, entitled RETINOID IMMUNOMODULATING KIT AND COMPOSITION AND USES THEREOF; U.S. Publication No. 06-0018937, published on Jan. 26, 2006, entitled STEROID KIT AND FOAMABLE COMPOSITION AND USES THEREOF; U.S. Publication No. 05-0271596, published on Dec. 8, 2005, entitled VASOACTIVE KIT AND COMPOSITION AND USES THEREOF; U.S. Publication No. 06-0269485, published on Nov. 30, 2006, entitled ANTIBIOTIC KIT AND COMPOSITION AND USES THEREOF; U.S. Publication No. 07-0020304, published on Jan. 25, 2007, entitled NON-FLAMMABLE INSECTICIDE COMPOSITION AND USES THEREOF; U.S. Publication No. 06-0193789, published on Aug. 31, 2006, entitled FILM FORMING FOAMABLE COMPOSITION; U.S. patent application Ser. No. 11/732,547, filed on Apr. 4, 2007, entitled ANTI-INFECTION AUGMENTATION OF FOAMABLE COMPOSITIONS AND KIT AND USES THEREOF; U.S. patent application Ser. No. 11/732,547, filed on Apr. 4, 2007, KERATOLYTIC ANTIFUNGAL FOAM; U.S. patent application Ser. No. 11/767,442, filed on Jun. 22, 2007, entitled FOAMABLE COMPOSITIONS AND KITS COMPRISING ONE OR MORE OF A CHANNEL AGENT, A CHOLINERGIC AGENT, A NITRIC OXIDE DONOR, AND RELATED AGENTS AND THEIR USES; U.S. patent application Ser. No. 11/825,406, filed on Jul. 5, 2007, entitled DICARBOXYLIC ACID FOAMABLE VEHICLE AND PHARMACEUTICAL COMPOSITIONS THEREOF; U.S. patent application Ser. No. 11/900,072, filed on Sep. 10, 2006, entitled FOAMABLE VEHICLE AND VITAMIN AND FLAVONOID PHARMACEUTICAL COMPOSITIONS THEREOF; and U.S. patent application Ser. No. 11/947,751, filed Nov. 29, 2007, entitled COMPOSITIONS WITH MODULATING AGENTS, all of which are incorporated herein by reference in their entirety. More particularly any of the active ingredients; the solvents; the surfactants; foam adjuvants; polymeric agents, penetration enhancers; preservatives, humectants; moisturizers; and other excipients as well as the propellants and methods listed therein can be applied herein and are incorporated by reference.

A "stable foam" is defined herein as a composition, which upon release from an aerosol can, creates a foam mass, which is sustained on a surface for at least one minute, more preferably at least two minutes, and yet more preferably for at least 5 minutes. A period of minutes is regarded as a short term, but nevertheless it allows a good and more than sufficient period of time for a subject to receive foam dispensed on a body surface and to spread it or to transfer it to another region and to spread it.

In terms of spreadability and absorption an acceptable foam is one, that does not readily collapse upon dispensing on the skin; spreads easily on a skin surface; at least partially absorbed following rubbing onto the skin, and more preferably, substantially absorbed following rubbing on the skin.

In terms of tactile properties, an acceptable foam is one, that: creates a pleasant feeling after application; leaves minimal oily residue; and leaves minimal shiny residual look.

Skin drying and skin barrier function. Short chain alcohols are known to dry the skin and impair the integrity of the skin barrier. By contrast, including a film forming agent in the composition of the present invention Does not cause unwanted skin barrier damage.

Irritability. Due to the lack of lower alcohols (C1-05) and improvement in skin barrier function, skin irritability is eliminated.

The petrolatum foam described herein has several advantages, when compared with hydroalcoholic foam compositions.

(1) Breakability. The foam is thermally stable or substantially so. Unlike hydroalcoholic foam compositions of the prior art, the foam is not "quick breaking", i.e., it does not readily collapse upon exposure to body temperature environment. Shear-force breakability of the foam is clearly advantageous over thermally induced breakability, since it allows comfortable application and well directed administration to the target area;

(2) Skin drying and skin barrier function. Polar solvents and or potent solvents can dry the skin and impair the integrity of the skin barrier. By contrast, combining a polar solvent and or potent solvent with an petrolatum emollient and or a hydrophobic carrier, unwanted skin barrier damage is reduced; and Irritability. Due to the improvement in skin barrier function, or further through addition of a humectant or a moisturizer skin irritability is corrected or ameliorated.

In terms of usability, the foamable composition is most advantageous, as revealed by clinical trials:

(i) Ease of application.
When foam is released it expands and allows easy spreading on the target area. This advantage is particularly meaningful in regards to the treatment of large skin surfaces.
Upon application, the foam readily spreads and absorbs into the skin.

(ii) The Foam is Drip-Free
The foam is not liquid and therefore does not leak when applied.
This allows precise application, without the product being spread on clothes or other parts of the body.

For the purpose of the specification the external limits of the various ranges given are approximate as will be appreciated by those skilled in the art. Therefore, for the purpose of interpreting the outer limits of the range the limits shall be deemed to include up to a 20% leeway outside the range, and preferably about at least a 10% leeway.

Fields of Applications

According to one or more embodiments, the foamable carrier and the foamable pharmaceutical or cosmetic composition are intended for administration to an animal or a human subject. In one or more embodiments, the composition is intended to treat the skin, a body surface, a body cavity, a deep body cavity, or a mucosal surface, e.g., the mucosa of the nose, mouth, eye, ear, respiratory system, vagina, rectum or colon.

By including an appropriate active agent in the compositions, the composition are useful in treating a patient having any one of a variety of dermatological disorders, which include inflammation as one or their etiological factors (also termed "dermatoses"), such as classified in a non-limiting exemplary manner according to the following groups:

Dermatitis including contact dermatitis, atopic dermatitis, seborrheic dermatitis, nummular dermatitis, chronic dermatitis of the hands and feet, generalized exfoliative dermatitis, stasis dermatitis; lichen simplex chronicus; diaper rash;

Bacterial infections including cellulitis, acute lymphangitis, lymphadenitis, erysipelas, cutaneous abscesses, necrotizing subcutaneous infections, staphylococcal scalded skin syndrome, folliculitis, furuncles, hidradenitis suppurativa, carbuncles, paronychial infections, and erythrasma;

Fungal Infections including dermatophyte infections, yeast Infections; parasitic Infections including scabies, pediculosis, creeping eruption;

Viral Infections;

Disorders of hair follicles and sebaceous glands including acne, rosacea, perioral dermatitis, hypertrichosis (hirsutism), alopecia, including male pattern baldness, alopecia greata, alopecia universalis and alopecia totalis; pseudofolliculitis barbae, keratinous cyst;

Scaling papular diseases including psoriasis, pityriasis rosea, lichen planus, pityriasis rubra pilaris;

Benign tumors including moles, dysplastic nevi, skin tags, lipomas, angiomas, pyogenic granuloma, seborrheic keratoses, dermatofibroma, keratoacanthoma, keloid;

Malignant tumors including basal cell carcinoma, squamous cell carcinoma, malignant melanoma, paget's disease of the nipples, kaposi's sarcoma;

Reactions to sunlight, including sunburn, chronic effects of sunlight, photosensitivity;

Bullous diseases including pemphigus, bullous pemphigoid, dermatitis herpetiformis, linear immunoglobulin A disease;

Pigmentation disorders including hypopigmentation such as vitiligo, albinism and postinflammatory hypopigmentation and hyperpigmentation such as melasma (chloasma), drug-induced hyperpigmentation, postinflammatory hyperpigmentation;

Disorders of cornification including ichthyosis, keratosis pilaris, calluses and corns, actinic keratosis;

Pressure sores, open wounds, chronic wounds, open ulcers and burns;

Disorders of sweating; and

Inflammatory reactions including drug eruptions, toxic epidermal necrolysis, erythema multiforme, erythema nodosum, and granuloma annulare.

The same advantage is expected when the composition is topically applied to a body cavity or mucosal surfaces, including, but not limited to the cranial cavity, the thoratic cavity, the abdominal cavity, the venteral cavity, the vagina, the rectum and penile cavities, the urinary tract, the nasal cavity, the mouth, the eye, the ear the peritoneum, the large and small bowel, the caecum, bladder, and stomach, the cavity between the uterus and the fallopian tubes, the ovaries and other body areas, which may accept topically-applied products. The composition is suitable to treat conditions of a body cavity and a mucosal membrane, such as post-surgical adhesions, chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

According to one or more embodiments, the compositions are also useful in the therapy of non-dermatological disorders by providing transdermal or trans-mucosal delivery of an active agent that is effective against non-dermatological disorders.

In one or more embodiments, the disorder is a health abnormality that responds to treatment with a hormone. A typical example of such abnormality is sexual dysfunction in men and women whereby androgen therapy is successfully used to restore sexual function. Other non-limiting examples of disorders/medical indications that are in the scope of treatment with a hormone according to the present invention are androgen deficiency, estrogen deficiency, growth disorders, hypogonadism, cancer, vasomotor symptoms, menopausal disorders, vulvar and vaginal atrophy, urethritis, hypoestrogenism, osteoarthritis, osteoporosis, uterine bleeding, Hirsutism, Virilization, ovarian tumors, hypothalamic pituitary unit diseases, testicular tumors, prostate cancer, hypopituitarism, Klinefelter's syndrome, testicular feminisation, orchitectomy, vasomotor symptoms (such as "hot flashes") associated with the menopause, metabolic abnormalities and mood disturbances.

Methodology

A general procedure for preparing foamable compositions is set out in WO 2004/037225, which is incorporated herein by reference.

Waterless Foam
1. Dissolve the polymers in the main solvent with heating or cooling as appropriate for specific polymer. Add the all other ingredients and heat to 75° C. to melt and dissolve the various ingredients.
2. Cool to below 40° C. and add sensitive ingredients with mild mixing.
3. Cool to room temperature.

Note ASOS is preferably added at stage 2

Oily Waterless Foam
1. Mix all ingredients excluding polymers and heat to 75° C. to melt and dissolve and obtain homogeneous mixture.
2. Mix well and cool to below 40° C. and add the polymers and sensitive ingredients with moderate mixing.
3. Cool to room temperature.

Emulsion Foam, Method (a)
1. Mix oily phase ingredients and heat to 75° C. to melt all ingredients and obtain homogeneous mixture.
2. Mix polymers in water with heating or cooling as appropriate for specific polymer.
3. Add all other water soluble ingredients to water-polymer solution and heat to 75° C.
4. Add slowly internal phase to external phase at 75° C. under vigorous mixing and homogenize to obtain fine emulsion.
5. Cool to below 40° C. and add sensitive ingredients with mild mixing.
6. Cool to room temperature.

Emulsion Foam, Method (b)
1. Mix oily phase ingredients and heat to 75° C. to melt all ingredients and obtain homogeneous mixture.
2. Mix polymers in water with heating or cooling as appropriate for specific polymer.
3. Add all other water soluble ingredients to water-polymer solution and heat to 75° C.
4. Add slowly external phase to internal phase at 75° C. under vigorous mixing and homogenize to obtain fine emulsion.
5. Cool to below 40° C. and add sensitive ingredients with mild mixing.
6. Cool to room temperature.

Oily Foam with Phospholipids and/or Water
1. Swell the phospholipids in the main oily solvent under mixing for at least 20 minutes until uniform suspension is obtained.
2. Add all other ingredients excluding polymers and heat to 75° C. to melt and dissolve and obtain homogeneous mixture.
3. Mix well and cool to below 40° C. and add the polymers and sensitive ingredients with moderate mixing.
4. Cool to room temperature.
5. In case of polymers dissolved in water or organic solvent, dissolve the polymers in the solvent with heating or cooling as appropriate for specific polymer and add to the oily mixture under vigorous mixing at ~40° C.

Petrolatum Zinc Oxide (Water/Oil) Emulsion

Step 1: Preparation of Water Phase
The water is heated to 70° C.

Step 2: Preparation of Oil Phase
The Oil Phase is prepared by mixing together of all ingredients and heat up to 70° C. Continue mixing until full melting for solid ingredients.

Step 3: PFF Formation

Step 3-a: Emulsification
The Water phase at 70-75° C. is added to the Oil phase in small portions at 70° C. The emulsification is performed in presence of vigorous agitation continues until PFF uniformity is reached for at least 20 min.

Step 4: Addition of Zinc Oxide
Stop heating the PFF and slow addition of Zinc Oxide at 40-50° C. during vigorous mixing. Continue mixing for at lease 30 min.

Petrolatum API (Water/Oil) Emulsion
The procedure is as above with API replacing or in addition to the Zinc oxide. For sensitive ingredients cool to below 40° C. and add them with mild mixing.

Petrolatum Zinc Oxide (Solvent/Oil) Emulsion
The procedure is as above for water in petrolatum emulsion, but, DMI, or PG, or PEG 400 replaces the water.

Petrolatum API (Solvent/Oil) Emulsion

The procedure is as above with API replacing or in addition to the Zinc oxide. For sensitive ingredients cool to below 40° C. and add them with mild mixing.

Petrolatum Zinc Oxide (Waterless)

Step 1: Preparation of Oil Phase

The Oil Phase is prepared by mixing together of all ingredients and heat up to 65° C. Continue mixing until full melting for solid ingredients.

Step 2: Addition of Zinc Oxide

Stop heating the oil phase and slow addition of Zinc Oxide at 40-50° C. during vigorous mixing. Continue mixing for at lease 30 min.

Production Under Vacuum

Optionally, the foamable formulation may be produced under nitrogen and under vacuum. Whilst the whole process can be carried out under an oxygen free environment, it can be sufficient to apply a vacuum after heating and mixing all the ingredients to obtain an emulsion or homogenous liquid. Preferably the production chamber is equipped to apply a vacuum but if not the formulation can be for example placed in a dessicator to remove oxygen prior to filing and crimping.

Loading and Testing of Canisters

An aerosol canister is filled with PFF and crimped with valve using vacuum crimping machine.

Pressurizing is then carried out using a gas mixture comprising n-Butane. Canisters are thereafter filled and preferably warmed for 30 seconds in a warm bath at 50° C. and well shaken immediately thereafter.

Each pressurized canister is subjected to bubble and crimping integrity testing by immersing the canister in a 60° C. water bath for 2 minutes. Canisters are observed for leakage as determined by the generation of bubbles. Canisters releasing bubbles are rejected.

Tests

By way of non limiting example the objectives of hardness, collapse time tests and aging are briefly set out below as would be appreciated by a person of the art.

Hardness

LFRA100 instrument is used to characterize hardness. A probe is inserted into the test material. The resistance of the material to compression is measured by a calibrated load cell and reported in units of grams on the texture analyzer instrument display. Preferably at least three repeat tests are conducted. The textural characteristics of a dispensed foam can effect the degree of dermal penetration, efficacy, spreadability and acceptability to the user. The results can also be looked at as an indicator of softness. Note: the foam sample is dispensed into an aluminum sample holder and filled to the top of the holder.

Collapse Time

Collapse time (CT) is examined by dispensing a given quantity of foam and photographing sequentially its appearance with time during incubation at 36° C. It is useful for evaluating foam products, which maintain structural stability at skin temperature for at least 1 minute. Thus foams which are structurally stable on the skin for at least one minute are termed "short term stable" compositions or foams.

Viscosity

Viscosity is measured with Brookfield LVDV-II+PRO with spindle SC4-25 at ambient temperature and 10, 5 and 1 RPM. Viscosity is usually measured at 10 RPM. However, at about the apparent upper limit for the spindle of ~>50,000 CP, the viscosity at 1 RPM may be measured, although the figures are of a higher magnitude.

FTC

FTC (Freeze Thaw Cycles) To check the foam appearance under extreme conditions of repeated cycles of cooling, heating, (first cycle) cooling, heating (second cycle) etc., commencing with −10° C. (24 hours) followed by +40° C. (24 hours) measuring the appearance and again repeating the cycle for up to three times.

Chemical Stability

The amount of active agent present is analyzed in foam expelled from various pressurized canisters containing foam formulations using HPLC. Analysis is carried out at zero time and at appropriate time intervals thereafter. The canisters are stored in controlled temperature incubators at 5° C., at 25° C., at, 40° C. and sometimes at 50° C. At appropriate time intervals canisters are removed and the amount of active agent in the foam sample is measured.

Focus Group

Five healthy volunteers selected at random were give a sample of foam formulation and applied it to the skin on their forearm and were asked to complete a questionnaire.

Corneometer

Skin hydration is measured using a Corneometer® CM 825 instrument. (Courage+Khazaka, Koln, Germany). The measuring principle of the Corneometer® CM 825 is based on capacitance measurement of dielectric medium. Any change in the dielectric constant due to skin surface hydration alters the capacitance of a measuring capacitor. It can detect even slight changes in the skin hydration level.

Bubble Size

Foams are made of gas bubbles entrapped in liquid. The bubble size and distribution reflects in the visual texture and smoothness of the foam. Foam bubbles size is determined by dispensing a foam sample on a glass slide, taking a picture of the foam surface with a digital camera equipped with a macro lens. The diameter of about 30 bubbles is measured manually relatively to calibration standard template. Statistical parameters such as mean bubble diameter, standard deviation and quartiles are then determined. Measuring diameter may also be undertaken with image analysis software. The camera used was a Nikon D40X Camera (resolution 10 MP) equipped with Sigma Macro Lens (ref: APO MACRO 150 mm F2.8 EX DG HSM). Pictures obtained are cropped to keep a squared region of 400 pixels×400 pixels. The light microscope enables observing and measuring particles from few millimeters down to one micron. Light microscope is limited by the visible light wavelength and therefore is useful to measuring size of particles above 800 nanometers and practically from 1 micron (1,000 nanometers).

"Shakability" represents the degree to which the user is able to feel/hear the presence of the liquid contents when the filled pressurized canister is shaken. Shaking is with normal mild force without vigorous shaking or excessive force. When the user cannot sense the motion of the contents during shaking the product may be considered to be non shakable. This property may be of particular importance in cases where shaking is required for affecting proper dispersion of the contents.

Shakability Scoring:

| | |
|---|---|
| Good shakability (conforms to required quality specification) | 2 |
| Moderate shakability (conforms to required quality specification) | 1 |
| Not shakable (fails to meet required quality specification) but may still be flowable and allow foam formation of quality | 0 |
| Is substantially not able to pass through valve | Block |

Aging by Centrifugation:
1. Principle of test

The centrifugation used in this procedure serves as a stress condition simulating the aging of the liquid formulation under investigation. Under these conditions, the centrifugal force applied facilitates coalescence of dispersed globules or sedimentation of dispersed solids, resulting in loss of the desired properties of the formulation.

2. Procedure
   2.1. Following preparation of the experimental formulation/s, allow to stand at room temperature for ≥24 h.
   2.2. Handle pentane in the chemical hood. Add to each experimental formulation in a 20-mL glass vial a quantity of pentane equivalent to the specified quantity of propellant for that formulation, mix and allow formulation to stand for at least 1 h and not more than 24 h.
   2.3. Transfer each mixture to 1.5 mL microtubes. Tap each microtube on the table surface to remove entrapped air bubbles.
   2.4. Place visually balanced microtubes in the centrifuge rotor and operate the centrifuge at 1,000 rpm for 10 min. The centrifuge can be a BHG HEMLE Z 231M.
   2.5. Centrifugation can also be executed at a higher rpm for a shorter period or a lower rpm for a longer period bearing in mind the G force experienced by the formulations is many fold greater than the one G to which a formulation would be exposed to during its shelf life.

Stock Compositions

Non-limiting examples of how stock solutions are made up with and without API. Other stock solutions may be made using the same methodology by simply varying adding or omitting ingredients as would be appreciated by one of the ordinary skills in the art.

The following examples further exemplify the stable non-alcoholic foamable pharmaceutical carrier, pharmaceutical compositions thereof, methods for preparing the same, and therapeutic uses of the compositions. The invention is described with reference to the following examples. For the purpose of the Examples below it was sufficient to apply a vacuum only at the crimping stage although for long term stability preferably any vacuum should be applied during manufacture as well at a sufficient pressure so that any oxygen remaining in the formulation is virtually negligible. The examples are for the purposes of illustration only and are not intended to be limiting. Many variations may be carried out by one of ordinary skill in the art and are contemplated within the full scope the description herein.

EXAMPLES

Section A

Non-Aqueous Formulations with at Least About 60% to About 91% Petrolatum but Without Oil and Without Silicone Example A1

Two 77% Petrolatum Waterless Foams with Zinc Oxide

| Ingredient | 5 w/w % | 6 w/w % |
| --- | --- | --- |
| Petrolatum (Sofinetic ™ LMP) | 50.00 | 50.00 |
| Petrolatum white (Pionier ® 5464) | 27.00 | 27.00 |
| Glyceryl monostearate | 2.50 | 1.50 |

-continued

| Ingredient | 5 w/w % | 6 w/w % |
| --- | --- | --- |
| Sorbitan laurate | 3.00 | — |
| Myristyl alcohol | — | 2.00 |
| Stearyl alcohol | 2.50 | 2.50 |
| Polysorbate 20 | — | 2.00 |
| Zinc Oxide | 15.00 | 15.00 |
| Total product: | 100.00 | 100.00 |
| Propellant: n-butane | 20.00 | 20.00 |
| Results | | |
| Shakability | yes | yes |
| Foam quality | Good | Excellent |
| Color | White | White |
| Odor | No odor | No odor |
| Film | Good | Good |
| Density (g/mL) | NM* | 0.470 |
| Viscosity (cP) | 266,143 | 353,724 |

*NM—Not Measured

Comments: The formulations of example 2 are waterless ointment foam, without polymers, main hydrophobic petrolatum types are the Sofinetic™ LMP which is characterized in the lowest range of melting point for petroleum jelly USP and Petrolatum white. The ratio of Sofinetic™ and Petrolatum white is balanced to obtain excellent foam yet shakable non washable and heavy occlusive skin cover and greasy skin feeling.

Example A2

90% Petrolatum Based Waterless Foam with Different API's

2a. Stock Waterless

| Ingredient | Stock Waterless w/w % |
| --- | --- |
| Petrolatum (Sofinetic ™ LMP) | 58.82 |
| Petrolatum white (Pionier 5464) | 31.76 |
| Glyceryl monostearate | 1.76 |
| Stearyl alcohol | 2.94 |
| Myristyl alcohol | 2.35 |
| Polysorbate 20 | 2.35 |
| Total product: | 100.00 |
| Propellant: n-butane | 20.00 |
| Results | |
| Shakability | Yes |
| Foam quality | Good |
| Color | Transparent-white |
| Odor | No odor |
| Hardness (g) | 87.88 |
| Collapse Time (sec) | >300 |
| Viscosity (cP) | 118,174 |
| Centrifugation 3000 rpm | Stable |
| Washable | No |

Figure 3:
FIG. 3 is a picture of a waterless carrier composition comprising a propellant, which shows that the propellant is dissolved in the petrolatum of the composition and appears as a single translucent phase.

Comments: This formula was prepared in a pressurized glass bottle and a translucent single phase was observed with the propellant being dissolved in the petrolatum. See FIG. 3. The formula produced good quality foam.

2b. Stock Waterless+API's

| Ingredient | 12 w/w % | 13 w/w % | 14 w/w % | 15 w/w % |
|---|---|---|---|---|
| Stock PFF | 99.00 | 99.00 | 98.00 | 99.00 |
| Clotrimazole | 1.00 | | | |
| Diclofenace sodium | | 1.00 | | |
| Lidocaine base | | | 2.00 | |
| Terbinafine HCl | | | | 1.00 |
| Total product: | 100.00 | 100.00 | 100.00 | 100.00 |
| Propellant: n-butane | 20.00 | 20.00 | 20.00 | 20.00 |
| Results | | | | |
| Shakability | Yes | yes | yes | yes |
| Foam quality | Good | Good | Good | Good |

2c. Stock Waterless+API's

| Ingredient | 16 w/w % | 17 w/w % | 18 w/w % |
|---|---|---|---|
| Stock PFF | 99.88 | 95.00 | 85.00 |
| Betamethasone 17 valerate micronized | 0.12 | | |
| Acyclovir | | 5.00 | |
| Azelaic acid | | | 15.00 |
| Total product: | 100.00 | 100.00 | 100.00 |
| Propellant: n-butane | 20.00 | 20.00 | 20.00 |
| Results | | | |
| Shakability | yes | yes | yes |
| Foam quality | Good | Good+ | Good+ |

Example A3

77% Petrolatum Based Waterless Foam with 15% w/w Zinc Oxide with and without Additional API's

3a. Stock Waterless with Zinc Oxide

| Ingredient | Stock Waterless w/w % |
|---|---|
| Petrolatum (Sofmetic ™ LMP) | 50.00 |
| Petrolatum white (Pionier 5464) | 27.00 |
| Glyceryl monostearate | 1.50 |
| Stearyl alcohol | 2.50 |
| Myristyl alcohol | 2.00 |
| Polysorbate 20 | 2.00 |
| Zinc Oxide | 15.00 |
| Total product: | 100.00 |
| Propellant: n-butane | 20.00 |
| Results | |
| Shakability | Yes |
| Foam quality | Good |
| Color | White |
| Odor | No odor |
| Hardness (g) | 42.74 |
| Collapse Time (sec) | 130 |
| Viscosity (Cp) | 353,724 |
| Centrifugation 3000 rpm | Stable |
| Washable | No |

3b. Stock Waterless with Zinc Oxide+API's

| Ingredient | 29 w/w % | 30 w/w % | 31 w/w % | 32 w/w % |
|---|---|---|---|---|
| Stock PFF | 99.00 | 99.00 | 99.00 | 98.00 |
| Clindamicin phosphate | 1.00 | | | |
| Clotrimazole | | 1.00 | | |
| Diclofenace sodium | | | 1.00 | |
| Lidocaine base | | | | 2.00 |
| Total product: | 100.00 | 100.00 | 100.00 | 100.00 |
| Propellant: n-butane | 20.00 | 20.00 | 20.00 | 20.00 |
| Results | | | | |
| Shakability | yes | yes | yes | Yes |
| Foam quality | Good | Good | Good | Good |

3c. Stock Waterless with Zinc Oxide+API's

| Ingredient | 33 w/w % | 34 w/w % | 35 w/w % | 36 w/w % |
|---|---|---|---|---|
| Stock PFF | 99.00 | 95.00 | 85.00 | 95.00 |
| Terbinafine HCl | 1.00 | | | |
| Acyclovir | | 5.00 | | |
| Azelaic acid | | | 15.00 | |
| Caffeine | | | | 5.00 |
| Total product: | 100.00 | 100.00 | 100.00 | 100.00 |
| Propellant: n-butane | 20.00 | 20.00 | 20.00 | 20.00 |
| Results | | | | |
| Shakability | yes | yes | yes | Yes |
| Foam quality | Good | Good | Good | Good |

Example A4

(Theoretical) 71% Petrolatum Based Waterless Foam with 15% w/w Zinc Oxide and ASOS

| Ingredient | 37 w/w % |
|---|---|
| Petrolatum (Sofmetic ™ LMP) | 45.00 |
| Petrolatum white (Pionier 5464) | 27.00 |
| Glyceryl monostearate | 1.50 |
| Stearyl alcohol | 2.50 |
| Myristyl alcohol | 2.00 |
| Polysorbate 20 | 2.00 |
| Aluminum Starch Octenyl Succinate | 5.00 |
| Zinc Oxide | 15.00 |
| Total product: | 100.00 |
| Propellant: n-butane | 20.00 |

Example A5

(Theoretical) 71% Petrolatum based Waterless Foam with 15% w/w Zinc Oxide and Alkyl Lactate

| Ingredient | 38a w/w % | 38b w/w % | 38c w/w % |
|---|---|---|---|
| Petrolatum (Sofmetic ™ LMP) | 45.00 | 45.00 | 45.00 |
| Petrolatum white (Pionier 5464) | 27.00 | 27.00 | 27.00 |

-continued

| Ingredient | 38a w/w % | 38b w/w % | 38c w/w % |
|---|---|---|---|
| Glyceryl monostearate | 1.50 | 1.50 | 1.50 |
| Stearyl alcohol | 2.50 | 2.50 | 2.50 |
| Myristyl alcohol | 2.00 | 2.00 | 2.00 |
| Polysorbate 20 | 2.00 | 2.00 | 2.00 |
| Alkyl Lactate | 5.00 | 5.00 | 5.00 |
| Zinc Oxide | 15.00 | 15.00 | 15.00 |
| Total product: | 100.00 | 100.00 | 100.00 |
| Propellant: n-butane | 20.00 | | |
| Propellant:: n-butane and iso-butane mixture | | 20 | |
| Propellant: a PIB mixture (Propane, iso-butanee and n-butanee) | | | 20 |

Example A6

Unique 70% Petrolatum Based Non-Aqueous Foam with DMI and Zinc Oxide

| Ingredient | 39 w/w % |
|---|---|
| Petrolatum (Sofmetic ™ LMP) | 20.00 |
| Petrolatum white (Pionier 5464) | 50.00 |
| Steareth 2 | 0.75 |
| Steareth 21 | 1.00 |
| Glyceryl monostearate | 0.50 |
| Dimethyl Isosorbide | 12.75 |
| Zinc Oxide | 15.00 |
| Total product: | 100.00 |
| Propellant: n-butane | 20.00 |
| Results | |
| Shakability | Yes |
| Foam quality | Good |
| Color | White |
| Odor | No odor |
| Washable | No |

Example A7

Unique 70% Petrolatum Based Non-Aqueous Foam with PEG 400 and Zinc Oxide

| Ingredient | 40 w/w % |
|---|---|
| Petrolatum (Sofmetic ™ LMP) | 20.00 |
| Petrolatum white (Pionier 5464) | 50.00 |
| Steareth 2 | 0.75 |
| Steareth 21 | 1.00 |
| Glyceryl monostearate | 0.50 |
| PEG 400 | 12.75 |
| Zinc Oxide | 15.00 |
| Total product: | 100.00 |
| Propellant:n-butane | 20.00 |
| Results | |
| Shakability | Yes |
| Foam quality | Good+ |
| Color | White |

| Ingredient | 40 w/w % |
|---|---|
| Odor | No Odor |
| Washable | No |

Example A8

Unique 70% Petrolatum Based Non-Aqueous Foam with Propylene Glycol and Zinc Oxide

| Ingredient | 41 w/w % |
|---|---|
| Petrolatum (Sofmetic ™ LMP) | 20.00 |
| Petrolatum white (Pionier 5464) | 50.00 |
| Steareth 2 | 0.75 |
| Steareth 21 | 1.00 |
| Glyceryl monostearate | 0.50 |
| Propylene Glycol | 12.75 |
| Zinc Oxide | 15.00 |
| Total product: | 100.00 |
| Propellant: n-butane | 20.00 |
| Results | |
| Shakability | Yes |
| Foam quality | Good |
| Color | White |
| Odor | No odor |
| Washable | No |

Examples 9, 10 and 11 are waterless emulsions of liquid hydrophilic solvents DMI, PEG 400 or Propylene glycol, stabilized in petrolatum base. It has been unexpectedly observed that replacing the water in above water in petrolatum emulsions, yielded high quality foams.

Example A9

Formulations with Petrolatum Combinations

PART A—Minimal Ingredients of 60% Petrolatum a Foam Adjuvant a Polymer and API

| Ingredients | 42 w/w % |
|---|---|
| Petrolatum (Sofmetic ™ LMP) | 33 |
| Petrolatum white (Pionier ® 5464) | 27 |
| Oleyl alcohol | 10 |
| Aluminum Starch Octenyl Succinate | 15 |
| Zinc Oxide | 15 |
| Total product: | 100 |
| Propellant: n-butane | 20 |
| Results | |
| Viscosity (cP) | 249866.7 |
| Viscosity (0.1 RPM cP) | 175642.5 |
| Shakability | 2 |
| Foam quality | Good |
| Color | White |
| Odor | No odor |
| Density (g/mL) | 0.533 |
| collapse | >300/G |

PART B—72% Petrolatum, an Oil, a Surfactant, a Foam Adjuvant, a Polymer and API with Different Propellants

| Ingredient | 43A w/w % | 43B w/w % | 43C w/w % |
|---|---|---|---|
| Petrolatum (Sofmetic ™ LMP) | 45 | 45 | 45 |
| Petrolatum white (Pionier ® 5464) | 27 | 27 | 27 |
| IPM | 4 | 4 | 4 |
| Myristyl alcohol | 2 | 2 | 2 |
| Aluminum Starch Octenyl Succinate | 5 | 5 | 5 |
| Polysorbate 20 | 2 | 2 | 2 |
| Zinc Oxide | 15 | 15 | 15 |
| Total product: | 100 | 100 | 100 |
| Propellant: n-butane | 20 | | |
| Propellant:: n-butane and iso-butane mixture | | 20 | |
| Propellant: a PIB mixture (Propane, iso-butanee and n-butanee) | | | 20 |
| Results | | | |
| Viscosity (cP) | | 210195.1 | |
| Viscosity (0.1 RPM cP) | | 148608.3 | |
| Shakability | 2 | 2 | 2 |
| Foam quality | G | G | G |
| Color | White | white | white |
| Odor | no odor | no odor | no odor |
| Film Density (g/mL) | 0.393 | 0.501 | 0.5 |
| collapse | NR | >300/G | >300/G |
| hardness | 34.08 | >100 g | >100 g |

PART C—61% to 81% Petrolatum Formulations with and without Alkyl Lactate and DMI with API. Formulation 47 is with Different Propellants.

| Ingredient | 44 w/w % | 45 w/w % | 46 w/w % | 47a w/w % | 47b w/w % | 47 c w/w % | 48 w/w % |
|---|---|---|---|---|---|---|---|
| Petrolatum (Sofmetic ™ LMP) | 64 | 35 | 60 | 45 | 45 | 45 | 50 |
| Petrolatum white (Pionier ® 5464) | 27 | 27 | 27 | 27 | 27 | 27 | 27 |
| Glyceryl monostearate | 1.5 | 1.5 | 1.5 | 1.5 | 1.5 | 1.5 | 1.5 |
| Stearyl alcohol | 2.5 | 2.5 | 2.5 | 2.5 | 2.5 | 2.5 | 2.5 |
| Myristyl alcohol | 2 | 2 | 2 | 2 | 2 | 2 | 2 |
| DMI | | | | | | | 5 |
| Polysorbate 20 | 2 | 2 | 2 | 2 | 2 | 2 | 2 |
| Alkyl Lactate | | | | 5 | 5 | 5 | |
| Zinc Oxide | 1 | 30 | 5 | 15 | 15 | 15 | 10 |
| Total product: | 100 | 100 | 100 | 100 | 100 | 100 | 100 |
| Propellant: n-butane | 20 | 20 | 20 | 20 | | | 20 |
| Propellant:: n-butane and iso-butane mixture | | | | | 20 | | |
| Propellant: a PIB mixture (Propane, iso-butane and n-butane) | | | | | | 20 | |
| Results | | | | | | | |
| Viscosity (cP) | | | NR | | 212114.7 | | 231310.6 |
| Viscosity (0.1 RPM cP) | 326330.4 | 1488215.7 | 638903.6 | | 118694.7 | | 163005.2 |
| | (0.3 RPM) | (0.3 RPM) | (0.3 RPM) | | | | |
| Shakability | 1 | 2 | 1 | 2 | 1 | 1 | 2 |
| Foam quality | G | G | G | F | G | G | G |
| Color | white | White | white | white | white | white | white |
| Odor | v.f.o. | no odor | no odor | no odor | no odor | no odor | no odor |
| Density (g/mL) | 0.423 | 0.497 | 0.443 | NR | 0.478 | 0.497 | 0.402 |
| collapse | NR | NR | NR | NR | >300/G | >300/G | NR |
| hardness | 35.57 | 40.64 | 41.75 | NR | 93.33 | NR | 31.04 |

PART D-71% to 77% Petrolatum Formulations with and without Alkyl Lactate and DMI with API. Formulation 49 is with Different Propellants.

| Ingredient | 48 w/w % | 49 A w/w % | 49 B w/w % | 49 C w/w % |
|---|---|---|---|---|
| Petrolatum (Sofmetic ™ LMP) | 50 | 45 | 45 | 45 |
| Petrolatum white (Pionier ® 5464) | 27 | 27 | 27 | 27 |
| Glyceryl monostearate | 1.5 | 1.5 | 1.5 | 1.5 |
| Stearyl alcohol | 2.5 | | | |
| Myristyl alcohol | 2 | 2 | 2 | 2 |
| DMI | 5 | | | |
| Polysorbate 20 | 2 | | | |
| Alkyl Lactate | | 5 | 5 | 5 |
| Zinc Oxide | 10 | 15 | 15 | 15 |
| Total product: | 100 | 100 | 100 | 100 |
| Propellant: n-butane | 20 | 20 | | |
| Propellant:: n-butane and iso-butane mixture | | | 20 | |
| Propellant: a PIB mixture (Propane, iso-butane and n-butane) | | | | 20 |
| Results | | | | |
| Viscosity (cP) | 231310.6 | | 301695.6 | |
| Viscosity (0.1 RPM cP) | 163005.2 | | 171003.5 | |
| Shakability | 2 | 2 | 1 | 1 |
| Foam quality | G | FG | G | G |
| Color | white | White | white | white |
| Odor | no odor | no odor | no odor | no odor |
| Film | | | | |
| Density (g/mL) | 0.402 | NR | 0.452 | 0.473 |
| collapse | NR | NR | >300/G | >300/G |
| hardness | 31.04 | NR | 65.41 | >100 g |

PART E—Focus Group

| | Focus Group (4) | | | |
|---|---|---|---|---|
| Formulation | 45 | 46 | 48 | 49 |
| STICKY | 11 | 13 | 12 | 9 |
| ODOR | 11 | 8 | 13 | 16 |
| SHINY | 11 | 13 | 12 | 9 |
| SATISFACTION | 13 | 14 | 15 | 10 |
| FILM | 14 | 7 | 10 | 18 |
| Total | 60 | 51 | 62 | 62 |

Comments: Each individual applied the foam to their skin and completed a questionnaire when they gave a mark for each foam trait between 1 and 5 for each trait where 5 is excellent and 1 is poor. A preferred formulation is one with an average score eg about 60 or more.

PART F—A Study of Skin-Hydration Effect of Petrolatum Vehicle of Example A9

The study is single blind (study recipient is blinded). Healthy subjects are applied with single dose of formulations as shown in Example A9. Skin hydration is measured using a Corneometer® CM 825 instrument. (Courage+Khazaka, Koln, Germany). The measuring principle of the Corneometer® CM 825 is based on capacitance measurement of dielectric medium. Any change in the dielectric constant due to skin surface hydration alters the capacitance of a measuring capacitor. It can detect even slight changes in the skin hydration level.

Skin hydration level is assessed at baseline with the Corneometer® CM 825. The formulations (about 0.075 g) is applied. Corneometers tested skin hydration after 15 mins following application. The skin was then washed and the hydration again measured.

Four circles of the same size are drawn on the forearms (applying area), two on each side and will be numbered from 1 to 4: The measurements were taken from marked areas only, since those the areas that were exposed to treatment.

| | Corneometer Results | | | |
|---|---|---|---|---|
| Formulation | 45 | 46 | 48 | 49A |
| ZT (Zero Time) av (4) | 37.5 | 40.75 | 34 | 39 |
| BEFORE WASHING | 39.25 | 32 | 36.5 | 30.25 |
| AFTER WASHING | 57.25 | 64 | 56.5 | 60.75 |

Comments: After washing a proective layer was still felt on the skin but the corneometer was able to detect about a 50% improvement in skin hydration as a result of the presence of the occlusive Zinc Oxide formulations even after a short period of 15 mins suggesting utility for example for nappy use.

Example 12

Exemplary Prophetic Foamable Formulations

Exemplary concentrations of active agents in foamable compositions are set out in Table 2. Each active agent is added into, for example, any of the carriers listed in any of the above Examples in a therapeutically effective concentration and amount. The methodology of addition is well known to those of the art. The composition is adjusted in each case so that it is made up to 100% w/w as appropriate by solvent or petrolatum.

TABLE 2

Exemplary Concentrations of Examples of Active Agents

| Class | Concentration | Exemplary Use |
|---|---|---|
| Hydrocortisone acetate | 1% | Steroid responsive inflammation and |
| Betamethasone valerate | 0.12% | psoriasis or atopic dermatitis |
| Clobetasol proprionate | 0.05% | |
| Acyclovir | 5% | Viral infection, herpes |
| Ciclopirox | 1% | Fungal infection, seborrhea, dandruff, |
| Clindamycin | 1-2% | Bacterial infection, acne, rosacea, |

TABLE 2-continued

Exemplary Concentrations of Examples of Active Agents

| Class | Concentration | Exemplary Use |
|---|---|---|
| Azelaic acid | 15% | Acne, rosacea, pigmentation disorder and various dermatoses |
| Metronidazol | 0.25%-2% | Rosacea, bacterial infections and parasite infestations |
| Diclofenac | 1% | Osteoarthritus, joint pain |
| Tacrolimus | 0.2% | Atopic dermatitis, eczema and inflammation |
| Caffeine | 5% | anti-cellulite |
| Clotrimazole | 1% | Fungal infection |
| Lidocaine base | 2% | Local anaesthetic |
| Terbinafine HCL | 1% | Fungal infection |
| Gentamycin | 0.1% | Bacterial skin infections, burns or ulcers |
| Dexpanthenol | 5% | Wounds, ulcers, minor skin infections |
| Urea | 5-10% | Emollient and keratolytic Atopic dermatitis, eczema, ichthyosis and hyperkeratotic skin disorders |
| Ammonium lactate | 12%-17.5% | Dry scaly conditions of the skin including ichthyosis |
| Povidone-iodine | 10% | Antimicrobial - antiseptic |
| Calcitriol | ~0.005% | Psoriasis |
| Calcipotriol | ~0.005% | Psoriasis |

Note, all the above active agents have a degree of solubility in water or petrolatum or the composition other than clobestol proprionate, which is practically insoluble; tacrolimus, which is insoluble in water; and betamethasone valerate which although has very limited solubility is nevertheless, surprisingly soluble at least to a degree in the compositions, in the water phase. Note, for example, calcipotriol solubility in water is 0.6 μg/mL.

The above examples represent different drug classes and it is to be understood that other drugs belonging to each of the classes represented above or described elsewhere in the specification may be included and used in the compositions in a safe and effective amount.

SECTION B—Formulations with in Excess of 50% Petrolatum and Oil, without Silicone and with no Water.

Example B1

High Content Petrolatum Based Non-Aqueous Foam with Mineral Oil and PPG

| Ingredient | 011 w/w % | 011A w/w % |
|---|---|---|
| Petrolatum (Sofmetic ™ LMP) | 75.00 | 77.32 |
| Light Mineral Oil | 3.00 | 3.09 |
| PPG stearyl ether | 5.00 | 5.15 |
| Behenyl alcohol [HLB 1.9] | 1.00 | 1.03 |
| Cetostearyl alcohol | 3.00 | 3.09 |
| ceteth 20 [HLB 15.7] | 3.00 | 3.09 |
| Glyceride Monostearate (GMS) | 1.00 | 1.03 |
| Span ® 80 [HLB 4.3] | 4.00 | 4.12 |
| Tween ® 20 [HLB 16.7] | 2.00 | 2.06 |
| Aluminum starch octenyl succinate (ASOS) | 3.00 | — |
| Total product: | 100.00 | 100.00 |
| Propellant: [propane: iso-butane: n-butane] mixture | 11.50 | 11.50 |

Results

| | | |
|---|---|---|
| Shakability | yes | yes |
| Foam quality | Good[a] | Good[a] |
| Color | white | white |
| Odor | No odor | No odor |
| Density | 0.172 | NM |
| Collapse Time | >300 seconds | NM |

[a]towards excellent

Figure 2A:
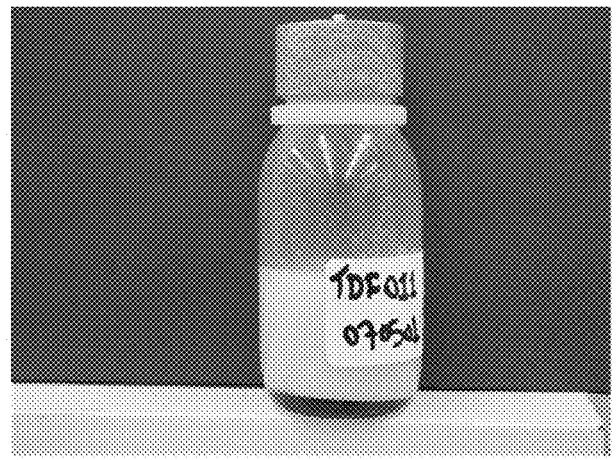
FIGS. 2a and 2b are pictures of two elevations (vertical and horizontal) of a waterless carrier high petrolatum oil carrier composition comprising a propellant, which shows that the formulation is homogeneous and liquid. The formulation is presented in Example 2.
Figure 2B:

Comments: This formula (having an average HLB of 9.36) was prepared in a pressurized glass bottle and a milky homogenous single phase was observed with the propellant being dissolved in the petrolatum (see FIGS. 2a and 2b below). After being subjected to about 10 minutes centrifugation at 1000 rpm, the formulation remained stable. Comparing this foam to the foam prepared according to Example 1, it can be seen that the presence of a large amount of liquid solvent (e.g. PPG) in Example 1 appears to facilitate the reduction or elimination of a liquid surfactant from the formulation when a waxy or solid surfactant is present. ASOS contributed to an improved skin feeling. The formulation produced a good quality foam in the absence of ASOS.

Example B2

Effect of Surfactant on High Content Petrolatum Based Non-Aqueous Foam with Mineral Oil and PPG

| Ingredient | 11-1 w/w % | 11-2 w/w % | 11-3 w/w % |
|---|---|---|---|
| Petrolatum (Sofmetic ™ LMP) | 75.00 | 75.00 | 75.00 |
| Light Mineral oil | 3.00 | 3.00 | 3.00 |
| PPG stearyl ether | 5.00 | 5.00 | 5.00 |
| Tween ® 20 [HLB 16.7] | 14.00 | | 7.00 |
| Span ® 80 [HLB 4.3] | | 14.00 | 7.00 |
| Aluminum starch octenyl succinate | 3.00 | 3.00 | 3.00 |
| Total product: | 100.00 | 100.00 | 100.00 |
| Propellant: propane: iso-butane: n-butane mixtures | 10% | 10% | 10% |
| Average HLB | 16.70 | 4.3 | 10.5 |

-continued

| Ingredient | 11-1 w/w % | 11-2 w/w % | 11-3 w/w % |
|---|---|---|---|
| Results | | | |
| Shakability | Good | Good | Good |
| Foam quality | Fairly Good | Fairly Good[b] | Fairly Good |
| Color | White | White | White |
| Odor | No odor | No odor | No odor |

[b]One sample showed an almost good foam.

Comments: In these experiments formulations containing liquid surfactants of varying HLB values were prepared by modifying the ratio between Tween 20, a liquid surfactant having an HLB of 16.7, and Span 80, a liquid surfactant having an HLB of 4.3. No significant changes were observed between the various formulations and resulting foams. A different mixture of propellant was tried at 11.5%. Foam quality observed in all three cases was fairly good. In addition, two formulations containing no surfactant (one with aluminum starch octenyl succinate and the other without) were prepared but were not able to produce anything like a viable or usable foam.

Example B3

High 75% Content Petrolatum Based Non-Aqueous Foam with Mineral Oil and PPG with Active Ingredients

| Ingredients | w/w |
|---|---|
| White Petrolatum (sofmetic) | 75.00 |
| light Mineral oil | 3.00 |
| PPG 15 stearyl ether | 4.93 |
| Cetostearyl alcohol | 3.00 |
| Behenyl alcohol | 1.00 |
| Ceteth 20 | 3.00 |
| steareth 2 | — |
| Glyceryl mono stearate | 1.00 |
| Sorbitan monooleate 80 | 4.00 |
| polysorbate 20 | 2.00 |
| Aluminum starch octenyl succinate | 3.00 |
| Calcipotriol | 0.005 |
| Betamethasone Dipropionate | 0.064 |
| Total | 100.00 |

| Ingredients | w/w |
|---|---|
| Propellant: propane; iso-butane; n-butane mixtures | 11.5% |
| Results | |
| Shakability | Good |
| Appearance: Quality | Good |
| Odor | No odor |
| Color | White |
| Density | 0.172 |
| Collapse time at 36° C. (sec.) | >300 |
| Hardness | 20.29 |

Comments: High and relatively Low petrolatum formulations appear to be good waterless carriers for active ingredients. The hardness results observed indicates that both the high and relatively low petrolatum concentrations produce soft foams. The results with active ingredients can be readily extrapolated to apply to the carrier without any active ingredient since the amount of active agent is well below 0.1% and therefore any effect on hardness is anticipated to be negligible. The vitamin D derivative may easily be replaced by an effective amount of another such as calcitriol. Likewise the steroid may be replaced by an effective amount of another steroid such as BMV. Although a combination of API's is exemplified the formulation may alternatively contain only one of them.

Example B4

High 79%-85% Petrolatum Based Non-Aqueous Foam with Mineral Oil PPG-15 Stearyl Ether and Cetostearyl Alcohol with Active Ingredients Calcipotriol and Betamethasone Dipropionate (BMD)

| Ingredients | 026 | 027 | 028 | 029 | 030 |
|---|---|---|---|---|---|
| White Petrolatum (sofmetic) | 85.0 | 81.0 | 83.0 | 83.0 | 79.0 |
| light Mineral oil | 3.0 | 3.0 | 3.0 | 3.0 | 3.0 |
| Cetostearyl alcohol | 3.0 | 3.0 | 3.0 | 3.0 | 3.0 |
| Ceteth 20 | 3.0 | 3.0 | 3.0 | 3.0 | 3.0 |
| Glyceryl monostearate | 1.0 | 1.0 | 1.0 | 1.0 | 1.0 |
| Sorbitan monooleate | — | 4.0 | — | — | 4.0 |
| Polysorbate 20 | — | — | 2.0 | — | 2.0 |
| Polysorbate 80 | — | — | — | 2.0 | — |
| Calcipotriol | 0.005 | 0.005 | 0.005 | 0.005 | 0.005 |
| Betamethasone dipropionate | 0.064 | 0.064 | 0.064 | 0.064 | 0.064 |
| PPG-15 stearyl ether | 4.93 | 4.93 | 4.93 | 4.93 | 4.93 |
| Propellant (propane/butane/isobutene) | 8.00 | 8.00 | 8.00 | 8.00 | 8.00 |
| Total: | 100.0 | 100.0 | 100.0 | 100.0 | 100.0 |
| Results at time point zero: | | | | | |
| Shakability | good | moderate | Good | poor | moderate |
| Density [g/mL] | 0.177 | 0.215 | 0.202 | 0.257 | 0.165 |
| Foam Quality | FG | G | G− | G− | G |

-continued

| Ingredients | 026 | 027 | 028 | 029 | 030 |
|---|---|---|---|---|---|
| Foam Color | White | White | White | White | White |
| Foam Odor | no odor | no odor | no odor | no odor | no odor |
| Collapse Time (sec) | — | >300 | — | — | — |
| Assay of Calcipotriol (% w/w) | 0.0050 | 0.0048 | 0.0047 | 0.0047 | 0.0050 |
| Assay of Betamethasone dipropionate (% w/w) | 0.061 | 0.063 | 0.061 | 0.060 | 0.063 |
| Results after 2 months at 40° C.: | | | | | |
| Shakability | good | good | Good | good | good |
| Density [g/mL] | — | 0.158 | — | — | 0.152 |
| Foam Quality | FG | G− | FG | FG | G− |
| Foam Color | off-white | White | off-white | off-white | White |
| Foam Odor | faint odor | faint odor | faint odor | faint odor | faint odor |
| Assay of Calcipotriol (% w/w) | 0.0036 | 0.0046 | 0.0024 | 0.0041 | 0.0044 |
| Assay of Betamethasone dipropionate (% w/w) | 0.052 | 0.060 | 0.038 | 0.055 | 0.059 |
| Results after 3 months at 40° C.: | | | | | |
| Shakability | good | good | Good | good | good |
| Density [g/mL] | — | — | — | — | — |
| Foam Quality | FG | G− | FG | FG | G− |
| Foam Color | off-white | White | off-white | off-white | White |
| Foam Odor | faint odor | faint odor | faint odor | faint odor | faint odor |
| Assay of Calcipotriol (% w/w) | 0.0036 | 0.0046 | 0.0024 | 0.0041 | 0.0044 |
| Assay of Betamethasone dipropionate (% w/w) | 0.052 | 0.060 | 0.038 | 0.055 | 0.059 |

Comments: The addition of sorbitan stearate or of polysorbate surfactants enhanced the foam quality. The formulations without sorbitan stearate were less stable physically and chemically. Vehicles 27 and 30 displayed physical and chemical stability for three months at 40 C. It is possible that the polysorbate surfactant may effect stability. Although combined herein in one carrier the active ingredients may in an alternative embodiment be presented in two separate canisters in the same or different carriers adapted to maximize the stability of the active ingredients. For example, the steroid formulation may have a modulating agent present such that the formulation is at an artificial acid pH. Likewise the vitamin D derivative may have a modulating agent present such that the formulation is at an artificial basic pH. The vitamin D derivative may easily be replaced by an effective amount of another such as calcitriol. Likewise the steroid may be replaced by an effective amount of another steroid such as BMV. Although a combination of API's is exemplified the formulation may alternatively contain only one of them.

Example B5

High 85% Petrolatum Based Non-Aqueous Foam with Mineral Oil PPG-15 Stearyl Ether and Lecithin with Active Steroid Ingredients Betamethasone Valerate (BMV); Betamethasone Dipropionate; Clobetasol Propionate; and Triamcinolone Acetonide A) Betamethasone Valerate

| Ingredients | |
|---|---|
| White Petrolatum (sofmetic) | 85 |
| Light Mineral oil | 3 |
| PPG stearyl ether | 8.48 |
| Lecithin | 1.4 |

-continued

| Ingredients | |
|---|---|
| Sorbitan stearate | 2 |
| Betamethasone valerate | 0.12 |
| Total | 100 |
| Results at time point zero: | |
| Shakability | Good |
| Density [g/mL] | 0.103 |
| Foam Quality | Good |
| Foam Color | White |
| Foam Odor | no odor |
| Collapse Time (sec) | >300 |
| Assay of Betamethasone valerate (% w/w) | 0.116 |
| Results after 2 months at 40° C.: | |
| Shakability | Good |
| Density [g/mL] | 0.112 |
| Foam Quality | Good |
| Foam Color | White |
| Foam Odor | no odor |
| Collapse Time (sec) | 190 |
| Assay of Betamethasone valerate (% w/w) | 0.115 |
| Results after 3 months at 40° C.: | |
| Shakability | Good |
| Density [g/mL] | 0.108 |
| Foam Quality | Good |
| Foam Color | White |
| Foam Odor | faint odor |
| Collapse Time (sec) | 130 |
| Assay of Betamethasone valerate (% w/w) | 0.109 |

B) Betamethasone Dipropionate

| Ingredients | |
|---|---|
| White Petrolatum (sofmetic) | 85 |
| Light Mineral oil | 3 |

-continued

| Ingredients | |
|---|---|
| PPG stearyl ether | 8.54 |
| Lecithin | 1.4 |
| Sorbitan stearate | 2 |
| Betamethasone dipropionate | 0.064 |
| Total | 100.004 |
| Assay of Betamethasone dipropionate (% w/w) | |
| Time point zero | 0.061 |
| after 2 weeks at 40° C. | 0.059 |

C) Clobetasol Propionate

| Ingredients | |
|---|---|
| White Petrolatum (sofmetic) | 85 |
| Light Mineral oil | 3 |
| PPG stearyl ether | 8.55 |
| Lecithin | 1.4 |
| Sorbitan stearate | 2 |
| Clobetasol propionate | 0.05 |
| Total | 100 |
| Assay of Clobetasol propionate (% w/w) | |
| Time point zero | 0.049 |
| after 2 weeks at 40° C. | 0.047 |

D) Triamcinolone Acetonide

| Ingredients | |
|---|---|
| White Petrolatum (sofmetic) | 85 |
| Light Mineral oil | 3 |
| PPG stearyl ether | 8.54 |
| Lecithin | 1.4 |
| Sorbitane stearate | 2 |
| Betamethasone dipropionate | 0.1 |
| Total | 100.04 |
| Assay of Triamcinolone Acetonide (% w/w) | |
| Time point zero | 0.096 |
| after 2 weeks at 40° C. | 0.100 |

Comments: The lecicthin vehicle showed good foam quality and a collapse time in excess of 300 secs and was found to be stable at 40 C for several months with BMV. Preliminary accelerated stability tests for two weeks with other steroids indicated that the vehicle can be stable with other steroids. It is predicted that if the lecithin carrier were to be stability tested with an effective amount of other steroids for example halobetasol propionate or hydrocortisone butyrate, the formulations would also show stability.

Example B6

Petrolatum, Mineral Oil Formulations with and without Lecithin and PPG 15 Stearyl Ether PART A wherein the petrolatum mineral oil combination is about at least 75% and the petrolatum is in excess of 50%.

| Ingredient | 038 % w/w | 039 % w/w | 040 % w/w | 041 % w/w | 042 % w/w |
|---|---|---|---|---|---|
| Zinc oxide | 15 | 15 | 15 | 15 | 15 |
| Petrolatum (sofmetic) | 71 | 58.5 | 58.5 | 71 | 56 |
| Mineral oil, light | 5 | 20 | 20 | 5 | 20 |
| Lecithin | 1 | | | 1 | 1 |
| Ceteth 20 | | | 3 | 3 | 3 |
| Sorbitan stearate | 3 | 3 | | | |
| PPG 15 stearyl ether | 5 | | | 5 | 5 |
| GMS | | 0.5 | 0.5 | | |
| Cetostearyl alcohol | | 3 | 3 | | |
| Control | 100 | 100 | 100 | 100 | 100 |
| Propellant AP70 | 8 | 8 | 8 | 8 | 8 |

PART B wherein the petrolatum mineral oil combination is about at least 65% and the petrolatum is in the majority.

| Ingredient | 043 % w/w | 044 % w/w | 045 % w/w | 046 % w/w | 047 % w/w |
|---|---|---|---|---|---|
| Zinc oxide | 15 | 15 | 15 | 15 | 15 |
| Petrolatum (sofmetic) | 46 | 46 | 56 | 61 | 61 |
| Mineral oil, light | 20 | 20 | 20 | 5 | 5 |
| Lecithin | 1 | 1 | 1 | 1 | 1 |
| Ceteth 20 | 3 | | | 3 | |
| Sorbitan stearate | | 3 | 3 | | 3 |
| PPG 15 stearyl ether | 15 | 15 | 5 | 15 | 15 |
| CMS | | | | | |
| Cetostearyl alcohol | | | | | |
| Control | 100 | 100 | 100 | 100 | 100 |
| Propellant AP70 | 8 | 8 | 8 | 8 | 8 |

PART C wherein the petrolatum mineral oil combination is about at least 78% and the petrolatum is in excess of 50%.

| Ingredient | 048 % w/w | 049 % w/w | 050 % w/w |
|---|---|---|---|
| Zinc oxide | 15 | 15 | 15 |
| Petrolatum (sofmetic) | 73.5 | 58.5 | 73.5 |
| Mineral oil, light | 5 | 20 | 5 |
| Lecithin | | | |
| Ceteth 20 | 3 | | |
| Sorbitan stearate | | 3 | 3 |
| PPG 15 stearyl ether | | | |
| GMS | 0.5 | 0.5 | 0.5 |
| Cetostearyl alcohol | 3 | 3 | 3 |
| Control | 100 | 100 | 100 |
| Propellant AP70 | 8 | 8 | 8 |

PART C—Results at Zero Time, for FTC (4 Cycles), and After Two Weeks at 40 C

038

| Test | T-0 | FTC upr | FTC inv | 40° C., upr | 40° C., inv |
|---|---|---|---|---|---|
| Quality | 5 | 5 | 5 | 5 | 5 |
| Color | 1 | 1 | 1 | 1 | 1 |
| Odor | 2 | 2 | 2 | 2 | 2 |
| Shakability | 2 | 2 | 2 | 2 | 2 |
| Density (g/ml) | 0.115 | 0.118 | 0.115 | 0.117 | 0.113 |
| Collapse time (sec) | >300/G | >300/G | >300/G | >300/G | >300/G |

039

| Test | T-0 | FTC upr | FTC inv | 40° C., upr | 40° C., inv |
|---|---|---|---|---|---|
| Quality | 5 | 5 | 5 | 5 | 5 |
| Color | 1 | 1 | 1 | 1 | 1 |
| Odor | 2 | 2 | 2 | 2 | 2 |
| Shakability | 2 | 2 | 2 | 2 | 2 |
| Density (g/ml) | 0.165 | 0.155 | 0.152 | 0.135 | 0.155 |
| Collapse time (sec) | >300/G | >300/G | >300/G | >300/G | >300/G |

040

| Test | T-0 | FTC upr | FTC inv | 40° C., upr | 40° C., inv |
|---|---|---|---|---|---|
| Quality | 5 | 5 | 5 | 5 | 5 |
| Color | 1 | 1 | 1 | 1 | 1 |
| Odor | 2 | 2 | 2 | 2 | 2 |
| Shakability | 2 | 2 | 2 | 2 | 2 |
| Density (g/ml) | 0.165 | 0.158 | 0.168 | 0.140 | 0.148 |
| Collapse time (sec) | >300/G | 200/F | >300/G | >300/FG | >300/G |

041

| Test | T-0 | FTC upr | FTC inv | 40° C., upr | 40° C., inv |
|---|---|---|---|---|---|
| Quality | 5 | 5 | 5 | 5 | 5 |
| Color | 1 | 1 | 1 | 1 | 1 |
| Odor | 2 | 2 | 2 | 2 | 2 |
| Shakability | 2 | 2 | 2 | 2 | 2 |
| Density (g/ml) | 0.145 | 0.140 | 0.123 | 0.120 | 0.120 |
| Collapse time (sec) | 180/F | >300/F | 140/F | 190/F | 130/F |

042

| Test | T-0 | FTC upr | FTC inv | 40° C., upr | 40° C., inv |
|---|---|---|---|---|---|
| Quality | 5 | 5 | 5 | 5 | 5 |
| Color | 1 | 1 | 1 | 1 | 1 |
| Odor | 2 | 2 | 2 | 2 | 2 |
| Shakability | 2 | 2 | 2 | 2 | 2 |
| Density (g/ml) | 0.155 | 0.140 | 0.128 | 0.145 | 0.140 |
| Collapse time (sec) | 220/F | 130/F | 100/F | 150/F | 130/F |

043

| Test | T-0 | FTC upr | FTC inv | 40° C., upr | 40° C., inv |
|---|---|---|---|---|---|
| Quality | 5 | 5 | 5 | 5– | 5– |
| Color | 1 | 1 | 1 | 1 | 1 |
| Odor | 2 | 2 | 2 | 2 | 2 |
| Shakability | 2 | 2 | 2 | 2 | 2 |
| Density (g/ml) | 0.148 | 0.147 | 0.128 | 0.128 | 0.117 |
| Collapse time (sec) | >300/F | 70/F | 70/F | 80/F | 80/F |

-continued

044

| Test | T-0 | FTC upr | FTC inv | 40° C., upr | 40° C., inv |
|---|---|---|---|---|---|
| Quality | 5 | 5 | 5 | 5 | 5 |
| Color | 1 | 1 | 1 | 1 | 1 |
| Odor | 2 | 2 | 2 | 2 | 2 |
| Shakability | 2 | 2 | 2 | 2 | 2 |
| Density (g/ml) | 0.150 | 0.127 | 0.105 | 0.142 | 0.130 |
| Collapse time (sec) | >300/FG | 280/FG | 300/FG | 90/F | 90/F |

045

| Test | T-0 | FTC upr | FTC inv | 40° C., upr | 40° C., inv |
|---|---|---|---|---|---|
| Quality | 5 | 5 | 5 | 5 | 5 |
| Color | 1 | 1 | 1 | 1 | 1 |
| Odor | 2 | 2 | 2 | 2 | 2 |
| Shakability | 2 | 2 | 2 | 2 | 2 |
| Density (g/ml) | 0.138 | 0.122 | 0.118 | 0.127 | 0.123 |
| Collapse time (sec) | >300/G | 60/FG | 280/FG | 120/F | 80/F |

046

| Test | T-0 | FTC upr | FTC inv | 40° C., upr | 40° C., inv |
|---|---|---|---|---|---|
| Quality | 5 | 5 | 5 | 5 | 5 |
| Color | 1 | 1 | 1 | 1 | 1 |
| Odor | 2 | 2 | 2 | 2 | 2 |
| Shakability | 2 | 2 | 2 | 2 | 2 |
| Density (g/ml) | 0.160 | 0.158 | 0.162 | 0.133 | 0.128 |
| Collapse time (sec) | 180/F | 120/F | 140/F | 100/F | 80/F |

047

| Test | T-0 | FTC upr | FTC inv | 40° C., upr | 40° C., inv |
|---|---|---|---|---|---|
| Quality | 5 | 5 | 5 | 5 | 5 |
| Color | 1 | 1 | 1 | 1 | 1 |
| Odor | 2 | 2 | 2 | 2 | 2 |
| Shakability | 2 | 2 | 2 | 2 | 2 |
| Density (g/ml) | 0.115 | n/r | 0.102 | 0.123 | 0.112 |
| Collapse time (sec) | >300/FG | block | 270/F | 300/FG | 260/FG |

048

| Test | T-0 | FTC upr | FTC inv | 40° C., upr | 40° C., inv |
|---|---|---|---|---|---|
| Quality | 5 | 5 | 5 | 5 | 5 |
| Color | 1 | 1 | 1 | 1 | 1 |
| Odor | 2 | 2 | 2 | 2 | 2 |
| Shakability | 2 | 1 | 1 | 2 | 2 |
| Density (g/ml) | 0.200 | n/r | 0.145 | 0.148 | 0.148 |
| Collapse time (sec) | >300/G | bolck | >300/FG | 170/F | 110/F |

049

| Test | T-0 | FTC upr | FTC inv | 40° C., upr | 40° C., inv |
|---|---|---|---|---|---|
| Quality | 5 | 5 | 5 | 5 | 5 |
| Color | 1 | 1 | 1 | 1 | 1 |
| Odor | 2 | 2 | 2 | 2 | 2 |
| Shakability | 2 | 2 | 2 | 2 | 2 |
| Density (g/ml) | 0.190 | 0.160 | 0.162 | n/r | n/r |
| Collapse time (sec) | >300/FG | >300/G | >300/G | block | block |

050

| Test | T-0 | FTC upr | FTC inv | 40° C., upr | 40° C., inv |
|---|---|---|---|---|---|
| Quality | 5 | 5 | 5 | 5 | 5 |
| Color | 1 | 1 | 1 | 1 | 1 |

-continued

| | | | | | |
|---|---|---|---|---|---|
| Odor | 2 | 2 | 2 | 2 | 2 |
| Shakability | 1 | 1 | 1 | 2 | 2 |
| Density (g/ml) | 0.210 | 0.168 | 0.175 | 0.165 | 0.150 |
| Collapse time (sec) | >300/G | block | >300/G | >300/G | >300/G |

Comments: Formulations 39 and 40 appeared to be the most stable. FTC was four cycles.

Example B7

Exemplary (Prophetic) Foams Containing Pharmaceutical Active Ingredients (API)

Exemplary concentrations of active ingredients in foamable compositions are set out in Table 1. Each active ingredient is added into, for example, any of the carriers listed in any of the above Examples in a therapeutically effective concentration and amount. The methodology of addition is well known to those of the art. The composition is adjusted in each case so that it is made up to 100% w/w by either a solvent or petrolatum.

TABLE 1

Exemplary Concentration ranges of some APIs which are addable to foams

| Class | Concentration | Exemplary Use |
|---|---|---|
| Hydrocortisone acetate | 1% | Steroid responsive inflammation and psoriasis or |
| Betamethasone valerate | 0.12% | atopic dermatitis |
| Clobetasol proprionate | 0.05% | |
| Acyclovir | 5% | Viral infection, herpes |
| Ciclopirox | 1% | Fungal infection, seborrhea, dandruff, |
| Clindamycin | 1-2% | Bacterial infection, acne, *rosacea*, |
| Azelaic acid | 15% | Acne, rosacea, pigmentation disorder and various dermatoses |
| Metronidazol | 0.25%-2% | *Rosacea*, bacterial infections and parasite infestations |
| Diclofenac | 1% | Osteoarthritus, joint pain |
| Tacrolimus | 0.2% | Atopic dermatitis, eczema and inflammation |
| Caffeine | 5% | anti-cellulite |
| Clotrimazole | 1% | Fungal infection |
| Lidocaine base | 2% | Local anaesthetic |
| Terbinafine HCL | 1% | Fungal infection |
| Gentamycin | 0.1% | Bacterial skin infections, burns or ulcers |
| Dexpanthenol | 5% | Wounds, ulcers, minor skin infections |
| Urea | 5-10% | Emollient and keratolytic Atopic dermatitis, eczema, ichthyosis and hyperkeratotic skin disorders |
| Ammonium lactate | 12%-17.5% | Dry scaly conditions of the skin including ichthyosis |
| Povidone-iodine | 10% | Antimicrobial - antiseptic |
| Calcipotriol | ~0.005% | Psoriasis |
| Calcitriol | ~0.005% | Psoriasis |

The above examples represent different drug classes and it is to be understood that other drugs belonging to each of the classes represented above or described elsewhere in the specification may be included and may be used in the compositions in a safe and effective amount.

SECTION C—Formulations with in Excess of 80% Combinations of Petrolatum and Oil, without Silicone and with no Water.

Example C1

30% Petrolatum and in Excess of 50% Oil/PPG 15 Stearyl Ether Based Non-aqueous Foam

| Ingredient | 005 w/w % | 005-A w/w % |
|---|---|---|
| Petrolatum (Sofmetic ™ LMP) | 30.00 | 30.61 |
| Light Mineral Oil | 39.00 | 39.80 |
| PPG stearyl ether | 15.00 | 15.31 |
| Behenyl alcohol [HLB 1.9] | 1.00 | 1.02 |
| Cetostearyl alcohol | 4.00 | 4.08 |
| ceteth 20 [HLB 15.7] | 4.00 | 4.08 |
| Steareth 2 [HLB 4.7] | 3.00 | 3.06 |
| Glyceride Monostearate (GMS) [HLB 3.4] | 2.00 | 2.04 |
| Aluminum starch octenyl succinate (ASOS) | 2.00 | — |
| Total product: | 100.00 | 100.00 |
| Propellant: [propane: iso-butane: n-butane] mixture | 10.00 | 10.00 |

-continued

| Ingredient | 005 w/w % | 005-A w/w % |
|---|---|---|
| Results | | |
| Shakability | Yes | yes |
| Foam quality | Good[a] | Good[a] |
| Color | White | white |
| Odor | No odor | No odor |
| Density | 0.198 | NM |
| Collapse Time | >300 seconds | NM |

[a] towards excellent;
NM: not measured

Figure 1B:

Comments: This formula (having an average HLB of 8.56) was prepared in a pressurized glass bottle and a milky homogenous single phase was observed with the propellant being dissolved in the petrolatum (see FIGS. 1a and 1b below). A foam of similar properties was obtained for the same composition using an n-butane propellant (18%) instead of [propane: iso-butane: n-butane] propellant mixture. ASOS contributed to an improved skin feeling. The Formulation produced a good quality foam in the absence of ASOS.

Example C2

30% Petrolatum and in Excess of 50% Oil/PPG 15 Stearyl Ether Based Non-aqueous Foam with Active Ingredients

| Ingredients | w/w |
|---|---|
| White Petrolatum (sofmetic) | 30.00 |
| light Mineral oil | 39.00 |
| PPG 15 stearyl ether | 14.93 |
| Cetostearyl alcohol | 4.00 |
| Behenyl alcohol | 1.00 |
| Ceteth 20 | 4.00 |
| steareth 2 | 3.00 |
| Glyceryl mono stearate | 2.00 |
| Aluminum starch octenyl succinate | 2.00 |
| Calcipotriol | 0.005 |
| Betamethasone Dipropionate | 0.064 |
| Total | 100.00 |
| Propellant: propane; iso-butane; n-butane mixtures | 10% |
| Results | |
| Shakability | Good |
| Appearance: Quality | Good |
| Odor | No odor |
| Color | White |
| Density | 0.198 |
| Collapse time at 36° C. (sec.) | >300 |
| Hardness | 19.44 |

Comments: The formulation appears to be a good waterless carrier for active ingredients. The hardness results observed indicates that the high oil petrolatum combination concentrations produce soft foams. The results with active ingredients can be readily extrapolated to apply to the carrier without any active ingredient since the amount of active agent is well below 0.1% and therefore any effect on hardness is anticipated to be negligible. The vitamin D derivative may easily be replaced by an effective amount of another such as calcitriol. Likewise the steroid may be replaced by an effective amount of another steroid such as BMV. Although a combination of API's is exemplified the formulation may alternatively contain only one of them.

SECTION D—Formulations with in Excess of 50% Petrolatum without Oil, without Silicone and with up to About 26% Water.

Example D1

Two Petrolatum Water in Oil Emulsion Foams with Zinc Oxide

1a. Formulation Contain Polymer

| Ingredient | 1 w/w % | 2 w/w % |
|---|---|---|
| Petrolatum (Sofmetic ™ LMP) | 55.00 | 70.00 |
| Glyceryl monostearate | 0.50 | 0.50 |
| Sorbitan laurate | 1.00 | 1.00 |

-continued

| Ingredient | 1 w/w % | 2 w/w % |
|---|---|---|
| Cetyl alcohol | 1.00 | 1.00 |
| Water, purified | 26.25 | 11.30 |
| Sodium Carboxymethyl cellulose | 0.25 | 0.20 |
| Polysorbate 20 | 1.00 | 1.00 |
| Zinc Oxide | 15.00 | 15.00 |
| Total product: | 100.00 | 100.00 |
| Propellant: n-butane | 20.00 | 20.00 |
| Results | | |
| Shakability | yes | yes |
| Foam quality | Good+ | Good |
| Color | White | White |
| Odor | No odor | No odor |
| Film | Medium | Medium |
| Density (g/mL) | NM* | NM* |
| Viscosity (cP) | NM* | NM* |

*NM—Not Measured

1b. Formulation Without Polymer

| Ingredient | 3 w/w % | 4 w/w % |
|---|---|---|
| Petrolatum (Sofmetic ™ LMP) | — | 20.00 |
| Petrolatum white (Pionier ® 5464) | 70.00 | 50.00 |
| steareth 2 | — | 0.75 |
| steareth 21 | — | 1.00 |
| Glyceryl monostearate | 0.50 | 0.50 |
| Sorbitan laurate | 1.00 | — |
| Stearyl alcohol | 1.00 | — |
| Water, purified | 11.50 | 12.75 |
| Polysorbate 20 | 1.00 | — |
| Zinc Oxide | 15.00 | 15.00 |
| Total product: | 100.00 | 100.00 |
| Propellant: n-butane | 20.00 | 20.00 |
| Results | | |
| Shakability | yes | Yes |
| Foam quality | Good | Good |
| Color | White | White |
| Odor | No odor | No odor |
| Film | Excellent | Medium |
| Density (g/mL) | NM* | 0.560 |
| Viscosity (cP) | 390,0516 | 186,093 |

*NM—Not Measured

Comments: Example one, table 1a, shows formulations comprising polymers whereas 1b polymer-less foams. It should be noted, that good foams and desired properties are obtained with and without polymers.

Example D2

Petrolatum Water in Oil Emulsion Foam with Different API's

2a. Stock Emulsion

| Ingredient | Stock Emulsion w/w % |
|---|---|
| Petrolatum (Sofmetic ™ LMP) | 23.53 |
| Petrolatum white (Pionier ® 5464) | 58.82 |
| Steareth 2 | 0.88 |
| Steareth 21 | 1.18 |

-continued

| Ingredient | Stock Emulsion w/w % |
|---|---|
| Glyceryl monostearate | 0.59 |
| Water, purified | 15.00 |
| Total product: | 100.00 |
| Propellant: n-butane | 20.00 |
| Results | |
| Shakability | Yes |
| Foam quality | Good+ |
| Color | White |
| Odor | No odor |
| Hardness (g) | 69.62 |
| Collapse Time (sec) | >300 |
| Viscosity (cP) | 218,553 |
| Centrifugation 3000 rpm | Stable |
| Washable | No |

2b. Stock Emulsion+API's

| Ingredient | 7 w/w % | 8 w/w % | 9 w/w % |
|---|---|---|---|
| Stock PFF | 99.00 | 99.00 | 99.00 |
| Clindamicin phosphate | 1.00 | | |
| Clotrimazole | | 1.00 | |
| Diclofenace sodium | | | 1.00 |
| Total product: | 100.00 | 100.00 | 100.00 |
| n-butane | 20.00 | 20.00 | 20.00 |
| Results | | | |
| Shakability | yes | yes | Yes |
| Foam quality | Good+ | Good+ | Good+ |

2c. Stock Emulsion+API's

| Ingredient | 10 w/w % | 11 w/w % |
|---|---|---|
| Stock PFF | 99.88 | 95.00 |
| Betamethasone 17 valerate micronized | 0.12 | |
| Caffeine | | 5.00 |
| Total product: | 100.00 | 100.00 |
| n-butane | 20.00 | 20.00 |
| Results | | |
| Shakability | yes | Yes |
| Foam quality | Good+ | Good+ |

Example D3

Petrolatum Water in Oil Emulsion Foam with 15% w/w Zinc Oxide with and without Additional API's 3a. Stock Emulsion with Zinc Oxide

| Ingredient | Stock Emulsion w/w % |
|---|---|
| Petrolatum (Sofmetic ™ LMP) | 20.00 |
| Petrolatum white (Pionier 5464) | 50.00 |
| Steareth 2 | 0.75 |
| Steareth 21 | 1.00 |
| Glyceryl monostearate | 0.50 |

-continued

| Ingredient | Stock Emulsion w/w % |
|---|---|
| Water, purified | 12.75 |
| Zinc Oxide | 15.00 |
| Total product: | 100.00 |
| Propellant: n-butane | 20.00 |
| Results | |
| Shakability | Yes |
| Foam quality | Good+ |
| Color | White |
| Odor | No odor |
| Hardness (g) | 79.60 |
| Collapse Time (sec) | >300 |
| Viscosity (cP) | 186,093 |
| Centrifugation 3000 rpm | Stable |
| Washable | No |

Zinc oxide is uniformly dispersed in the formula, no aggregation or flocculation of zinc oxide was observed. The emulsion is non washable and enable tick occlusive persistent layer on the applied skin.

3b. Stock Emulsion with Zinc Oxide+API's

| Ingredient | 19 w/w % | 20 w/w % | 21 w/w % | 22 w/w % | 23 w/w % |
|---|---|---|---|---|---|
| Stock PFF | 99.00 | 99.00 | 99.00 | 98.00 | 99.00 |
| Clindamicin phosphate | 1.00 | | | | |
| Clotrimazole | | 1.00 | | | |
| Diclofenace sodium | | | 1.00 | | |
| Lidocaine base | | | | 2.00 | |
| Terbinafine HCl | | | | | 1.00 |
| Total product: | 100.00 | 100.00 | 100.00 | 100.00 | 100.00 |
| Propellant: n-butane | 20.00 | 20.00 | 20.00 | 20.00 | 20.00 |
| Results | | | | | |
| Shakability | yes | yes | yes | Yes | yes |
| Foam quality | Good | Good+ | Good+ | Good+ | Good |

3c. Stock Emulsion with Zinc Oxide+API's

| Ingredient | 24 w/w % | 25 w/w % | 26 w/w % | 27 w/w % | 28 w/w % |
|---|---|---|---|---|---|
| Stock PFF | 99.88 | 95.00 | 85.00 | 95.00 | 99.75 |
| Betamethasone 17 valerate micronized | 0.12 | | | | |
| Acyclovir | | 5.00 | | | |
| Azelaic acid | | | 15.00 | | |
| Caffeine | | | | 5.00 | |
| Miconazole nitrate | | | | | 0.25 |
| Total product: | 100.00 | 100.00 | 100.00 | 100.00 | 100.00 |
| Propellant: n-butane | 20.00 | 20.00 | 20.00 | 20.00 | 20.00 |
| Results | | | | | |
| Shakability | yes | yes | yes | yes | yes |
| Foam quality | Good+ | Good+ | Good | Good+ | Good+ |

What is claimed is:

1. A non-aqueous, substantially non-alcoholic foamable composition comprising: a foamable carrier and at least one liquefied or compressed gas propellant, the foamable carrier comprising:
   (1) a petrolatum or mixtures thereof at a concentration of about 25% to about 95% by weight of the foamable carrier;

(2) a hydrophobic solvent at a concentration of about 1% to about 70% by weight of the foamable carrier; and (3) at least one foam agent selected from the group consisting of a surfactant, a surfactant system, a foam adjuvant and combinations thereof; at a concentration of about 0.1% to about 20% by weight of the foamable carrier;

wherein the amount of petrolatum is about the same as or in excess of the hydrophobic solvent and, together, the hydrophobic solvent and petrolatum are present in the foamable carrier at a concentration of at least about 80% by weight of the foamable carrier;

wherein the composition is substantially free of silicone oil;

wherein the composition is substantially free of short chain alcohols having up to 5 carbon atoms in their carbon chain skeleton and one hydroxyl group; and wherein the composition is stored in a pressurized container and upon release expands to form a breakable foam which breaks upon application of shear force.

2. The composition of claim 1, wherein the foamable carrier further comprises at least one active pharmaceutical agent.

3. The composition of claim 2, wherein the composition is flowable or flowable to a degree and or is shakable or substantially so when stored in a pressurized container and upon release expands to form a breakable foam having no substantial or sustained cooling affect and having a foam hardness in the range of about 5 g to about 100 g.

4. The composition of claim 3, wherein the hydrophobic solvent is selected from the group consisting of an unctuous additive, an oil, a therapeutic oil, a PPG alkyl ether, and mixtures thereof.

5. The composition of claim 4, wherein the hydrophobic solvent comprises PPG-15 stearyl ether.

6. The composition of claim 4, wherein the hydrophobic solvent comprises a mineral oil.

7. The composition of claim 4, wherein the hydrophobic solvent comprises medium chain triglyceride oil.

8. The composition of claim 4, wherein the hydrophobic solvent is a combination of a mineral oil, medium chain triglyceride oil and a PPG alkyl ether.

9. The composition of claim 1, wherein the carrier has a viscosity from about 12,000 cP to about 500,000 cP.

10. The composition of claim 4, wherein the propellant dissolves in the composition.

11. The composition of claim 10, wherein the propellant is selected from the group consisting of a propellant comprising n-butane, a propellant comprising a mixture of n-butane, isobutane and propane; and a propellant comprising a hydrofluorocarbon.

12. The composition of claim 1, wherein the surfactant or surfactant system is selected from the group consisting of a polysorbate, polyoxyethylene (20) sorbitan monostearate, sorbitan monooleate, polyoxyethylene (20) sorbitan monooleate, a polyoxyethylene fatty acid ester, polyoxyethylene (8) stearate, polyoxyethylene (20) stearate, polyoxyethylene (40) stearate, polyoxyethylene (100) stearate, a polyoxyethylene alkyl ether, polyoxyethylene cetyl ether, polyoxyethylene (23) cetyl ether, polyoxyethylene (2) cetyl ether, polyoxyethylene (10) cetyl ether, a sucrose ester, a partial ester of sorbitol, sorbitan monolaurate, a monoglyceride, a diglyceride, isoceteth-20, ceteth 20, steareth 2, steareth 20, steareth 21, glyceryl monostearate, glucose methyl stearate, methyl glucose sesquistearate, span 20, tween 20, a mono fatty acid sucrose ester, a di fatty acid sucrose ester, a tri fatty acid sucrose ester, laureth-4, poyglyceryl 10 laurate, span 60, a sucrose stearic acid ester, isosteareth 20, and sodium stearyl phthalamate.

13. The composition of claim 12, wherein the surfactant or surfactant system comprises a combination of ceteth 20 and steareth-2 and the amount of surfactant or surfactant system is at a concentration of about 0.1% to about 10% by weight of the foamable carrier.

14. The composition of claim 1, wherein the foam adjuvant is selected from one or more of the group consisting of cetyl alcohol, stearyl alcohol, myristyl alcohol, oleyl alcohol, behenyl alcohol, and cetostearyl alcohol.

15. The composition of claim 2, wherein the foamable carrier further comprises at least one modulating agent selected from the group consisting of a pH adjuster, a buffering agent, a chelator, an antioxidant, an ionization agent, a stabilizing agent, a preservative and mixtures thereof.

16. The composition of claim 1, wherein the foamable carrier further comprises 0.01% to 5% by weight of the foamable carrier of a polymeric agent selected from the group consisting of a bioadhesive agent, a gelling agent, a film forming agent, and a phase change agent.

17. A non-aqueous, substantially non-alcoholic foamable composition comprising: a foamable carrier and at least one liquefied or compressed gas propellant, the foamable carrier comprising:

(1) a petrolatum or mixtures thereof at a concentration of about 46% to about 95% by weight of the foamable carrier;

(2) a hydrophobic solvent at a concentration of about 1% to about 45% by weight of the foamable carrier;

(3) at least one foam agent selected from the group consisting of a surfactant, a surfactant system; a foam adjuvant and combinations thereof at a concentration of about 0.1% to about 15% by weight of the foamable carrier; and (4) an effective amount of an active pharmaceutical agent;

wherein the ratio of the foamable carrier to the propellant ranges from about 100:5 to about 100:30;

wherein the composition is substantially free of silicone oil;

wherein the composition is substantially free of short chain alcohols having up to 5 carbon atoms in their carbon chain skeleton and one hydroxyl group; and wherein the composition is flowable or flowable to a degree and or is shakable or substantially so when stored in a pressurized container and upon release expands to form a breakable foam which breaks upon application of shear force, and having no substantial or sustained cooling affect and having a foam hardness in the range of about 5 g to about 100 g.

18. The composition of claim 3, wherein the active agent is selected from the group consisting of an anti-infective agent, an antibiotic agent, an antibacterial agent, an antifungal agent, an antiviral agent, an antiparasitic agent, a steroidal anti-inflammatory agent, a nonsteroidal anti-inflammatory agent, an immunosuppressive agent, an immunomodulator, an immunoregulating agent, a hormonal agent, a steroid, a vasoactive agent, a vasoconstructor, a vasodilator, vitamin A, a vitamin A derivative, a retinoid, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a burn healing agent, a disinfectant, an anesthetic, an antiallergic agent, an alpha hydroxyl acid, lactic acid, glycolic acid, a beta-hydroxy acid, a protein, a peptide, a neuropeptide, an allergen, an immunogenic substance, a haptene, an oxidizing agent, an antioxidant, a dicarboxylic acid, azelaic acid, sebacic acid, adipic acid, fumaric acid, an insecticide, a retinoid, an antiproliferative agent, an anticancer agent, a photodynamic therapy agent, an anti-wrinkle agent, a radical scavenger, a metal oxide, titanium dioxide, zinc oxide, zirconium oxide, iron oxide, silicone oxide, talc, an anti-acne agent, a skin whitening agent, a self tanning agent, an anti-cellulite agent, a skin protective agent, a masking agent, an anti-wart agent, a refatting agent, a lubricating agent and mixtures of any two or more thereof at any proportion or wherein the active agent is selected from the group consisting of acyclovir, azelaic acid, allantoin, ammonium lactate, benzoyl peroxide, caffeine, calcipotriol, calcitriol, nicotinamide, ciclopirox olamine, clindamycin hydrochloride, clindamycin phosphate, clindamycin palmitate hydrochloride, coal tar, cyanocobalamine, diclofenac sodium, gentamycin sulphate, lactic acid, glycyrrhizinic acid, magnesium ascorbyl phosphate, minoxidil, mupirocin, salicylic acid, terbinafine, urea, fusidic acid, a hydrocortisone, hydrocortisone sodium phosphate, hydrocortisone sodium succinate, a clobetasol, a halobetasol, a betamethasone, halobetasol, clobetasol-17-propionate, clobetasol-17-butyrate, ketoconazole, lidocaine hydrochloride, metronidazole, tetracycline, tetracycline hydrochloride, meclocycline sulfosalicylate, resorcinol, chloramphenicol, erythromycin, acriflavinium monochloride, ethacridine lactate, dibrompropamidine isetionate, chlorhexidine acetate, chlorhexidine gluconate, chlorhexidine hydrochloride, hexamidine isetionate, phenol, povidone-iodine, dequalinium chloride, hydroxyquinoline sulfate, potassium hydroxyquinoline sulphate, benzalkonium chloride, cetrimonium bromide, cetylpyridinium chloride, cetrimide, phenylmercuric acetate, phenylmercuric borate, mercuric chloride, silver nitrate, potassium permanganate, tosylchloramide sodium, prednisolone sodium phosphate, betamethasone sodium phosphate, betamethasone 17-valerate, betamethasone dipropionate, demeclocycline, demeclocycline hydrochloride, chlortetracycline hydrochloride, oxytetracycline hydrochloride, neomycin sulfate, bacitracin zinc, gentamicin sulphate, amikacin, amikacin sulphate, sulfathiazole sodium, mafenide acetate, idoxuridine, fumaric acid, mepyramine maleate, tripelennamine hydrochloride, promethazine hydrochloride, dimetindene maleate, diphenhydramine hydrochloride, cinchocaine hydrochloride, oxybuprocaine hydrochloride, benzocaine, tetracaine hydrochloride, pramoxine hydrochloride, panthenol, dexpanthenol, calcium pantothenate, hyaluronic acid, trypsin, aminobenzoic acid, methylrosanilinium chloride, sodium butyl hydroxybenzoate, sodium ethyl hydroxybenzoate, sodium methyl hydroxybenzoate, sodium propyl hydroxybenzoate, flucytosine, fluconazole and mixtures of any two or more thereof.

19. The composition of claim 18, wherein the active agent is selected from the group consisting of vitamin D, a vitamin D derivative, vitamin E, and a vitamin E derivative.

20. The composition of claim 18, wherein the active agent is a combination of calcitriol and alpha tocopherol.

21. The composition of claim 17, wherein the ratio of hydrophobic solvent to petrolatum is between about 1:1 to about 1:10.

22. The composition of claim 17, wherein the foam agent comprises a surfactant comprising ceteth-20- or steareth-2 or both ceteth-20 and steareth-2, and a foam agent comprising behenyl alcohol or cetostearyl alcohol or both behenyl alcohol and cetostearyl alcohol.

23. A method of treating or alleviating acne in a mammalian subject, the method comprising administering a therapeutically effective amount of a foam produced from the composition of claim 2 to a target site of said mammalian subject having acne, wherein said active ingredient is a tetracycline antibiotic.

24. The composition of claim 1, wherein the at least one foam agent comprises one or more of the following three combinations:
  i. ceteareth-6 and stearyl alcohol;
  ii. cetearyl alcohol and cetearyl glucoside; and
  iii. polyglyceryl-10 pentastearate and behenyl alcohol and sodium stearoyl lactylate.

25. The composition of claim 1, wherein the surfactant or surfactant system is a combination of at least two surfactants selected from the group consisting of at least two polyoxyethylene alkyl ethers, steareth 2 and steareth 20, steareth 2 and steareth 21, polyoxyethylene (40) stearate and polyoxyethylene (100) stearate, a combination of sucrose esters, sucrose stearate and sucrose distearate, a combination of sorbitan esters, sorbitan monolaurate and sorbitan monooleate, sorbitan monolaurate and sorbitan monostearate, a combination of sucrose esters and sorbitan esters, sucrose stearate and sorbitan monostearate, a combination of a liquid polysorbate and a PEG compound, polyoxyethylene (20) sorbitan monooleate and PEG-40 stearate and methyl glucose sesquistearate, glyceryl stearate and PEG-100 stearate, sorbitan stearate and sucrose cocoate, and polysorbate 80 and PEG-40 stearate.

26. The composition of claim 1, wherein the surfactant or surfactant system comprises a polymeric emulsifier or an acrylates/C10-30 alkyl acrylate crosspolymer.

* * * * *